(12) United States Patent
Takada et al.

(10) Patent No.: US 9,954,190 B2
(45) Date of Patent: Apr. 24, 2018

(54) ORGANIC ELECTRIC-FIELD LIGHT-EMITTING ELEMENT, LIGHT-EMITTING MATERIAL FOR ORGANIC ELECTRIC-FIELD LIGHT-EMITTING ELEMENT, AND LIGHT-EMITTING DEVICE, DISPLAY DEVICE, AND ILLUMINATION DEVICE USING SAME ELEMENT

(75) Inventors: Saki Takada, Kanagawa (JP); Yasunori Yonekuta, Kanagawa (JP); Toshihiro Ise, Kanagawa (JP); Tetsu Kitamura, Kanagawa (JP); Toru Watanabe, Kanagawa (JP); Wataru Sotoyama, Kanagawa (JP); Koji Takaku, Kanagawa (JP); Katsuyuki Youfu, Kanagawa (JP)

(73) Assignee: UDC IRELAND LIMITED, Dublin (IE)

( * ) Notice: Subject to any disclaimer, the term of this patent is extended or adjusted under 35 U.S.C. 154(b) by 1122 days.

(21) Appl. No.: 14/124,945

(22) PCT Filed: Jun. 5, 2012

(86) PCT No.: PCT/JP2012/064430
§ 371 (c)(1),
(2), (4) Date: Feb. 26, 2014

(87) PCT Pub. No.: WO2012/173011
PCT Pub. Date: Dec. 20, 2012

(65) Prior Publication Data
US 2014/0159024 A1    Jun. 12, 2014

(30) Foreign Application Priority Data

Jun. 16, 2011  (JP) ................... 2011-134146
Sep. 28, 2011  (JP) ................... 2011-212619

(51) Int. Cl.
*H01L 51/00* (2006.01)
*C07D 401/04* (2006.01)
(Continued)

(52) U.S. Cl.
CPC ........ *H01L 51/0094* (2013.01); *C07C 43/267* (2013.01); *C07C 211/61* (2013.01);
(Continued)

(58) Field of Classification Search
None
See application file for complete search history.

(56) References Cited

U.S. PATENT DOCUMENTS

2004/0076853 A1 *  4/2004  Jarikov ............... C09K 11/06
                                                           428/690

FOREIGN PATENT DOCUMENTS

JP    2006512395    4/2006
JP    2009182033    8/2009
(Continued)

OTHER PUBLICATIONS

Xiao, Jinchong et al. "Synthesis, Characterization, Self-Assembly, and Physical Properties of 11-Methylbenzo [d] pyreno [4, 5-b] furan". Organic Letters, May 19, 2011, 2011. vol. 13, No. 12, pp. 3004-3007.

*Primary Examiner* — Nathan T Leong
(74) *Attorney, Agent, or Firm* — Riverside Law LLP

(57) ABSTRACT

An organic electroluminescent element that uses a compound expressed by the following general formula emits dark blue light and exhibits little change in chromaticity during brightness modulation. (n1 is an integer from 0 to 8; the $R^1$ [groups] are each independently a substituent substituted for a hydrogen atom of the pyrene skeleton; X is $CR^aR^b$ ($R^a$ and $R^b$ are each independently a hydrogen atom or a substituent), O, S, or $SiR^dR^e$ ($R^d$ and $R^e$ are each (Continued)

independently a hydrogen atom or a substituent); and $A^1$ to $A^4$ represent each independently either N or $CR^f$ ($R^f$ represents a hydrogen atom or a substituent, and two adjacent $R^f$ [groups] may jointly form a saturated or unsaturated ring, but no more than two rings may be formed jointly by two or more of the $R^f$ [groups]).)

20 Claims, 5 Drawing Sheets

(51) Int. Cl.
| | |
|---|---|
| *C07D 235/18* | (2006.01) |
| *C07D 235/20* | (2006.01) |
| *C07D 209/56* | (2006.01) |
| *C07D 307/77* | (2006.01) |
| *C09K 11/06* | (2006.01) |
| *H01J 29/20* | (2006.01) |
| *H01L 51/50* | (2006.01) |
| *C07C 211/61* | (2006.01) |
| *C07C 217/94* | (2006.01) |
| *C07C 323/38* | (2006.01) |
| *C07D 495/04* | (2006.01) |
| *C07F 7/08* | (2006.01) |
| *C07D 213/38* | (2006.01) |
| *C07C 43/267* | (2006.01) |
| *C09B 57/00* | (2006.01) |
| *C09B 69/00* | (2006.01) |

(52) U.S. Cl.
CPC .......... *C07C 217/94* (2013.01); *C07C 323/38* (2013.01); *C07D 209/56* (2013.01); *C07D 213/38* (2013.01); *C07D 235/18* (2013.01); *C07D 235/20* (2013.01); *C07D 307/77* (2013.01); *C07D 401/04* (2013.01); *C07D 495/04* (2013.01); *C07F 7/0807* (2013.01); *C07F 7/0809* (2013.01); *C09B 57/001* (2013.01); *C09B 57/008* (2013.01); *C09B 69/008* (2013.01); *C09K 11/06* (2013.01); *H01J 29/20* (2013.01); *H01L 51/006* (2013.01); *H01L 51/0061* (2013.01); *H01L 51/5012* (2013.01); *C07C 2601/14* (2017.05); *C07C 2603/54* (2017.05); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *H01L 51/0056* (2013.01); *H01L 51/0073* (2013.01)

(56) References Cited

FOREIGN PATENT DOCUMENTS

| | | |
|---|---|---|
| KR | 20100118700 A | 11/2010 |
| KR | 20110034103 A | 4/2011 |
| WO | 2010012323 | 2/2010 |
| WO | 2010126234 A1 | 11/2010 |
| WO | 2011037429 A2 | 3/2011 |

* cited by examiner

FIG. 4(A) LUMO
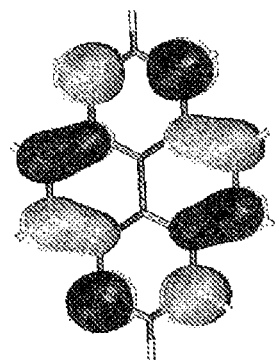
FIG. 4(B) HOMO
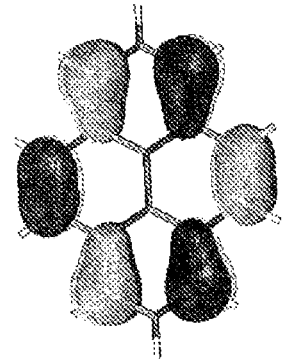

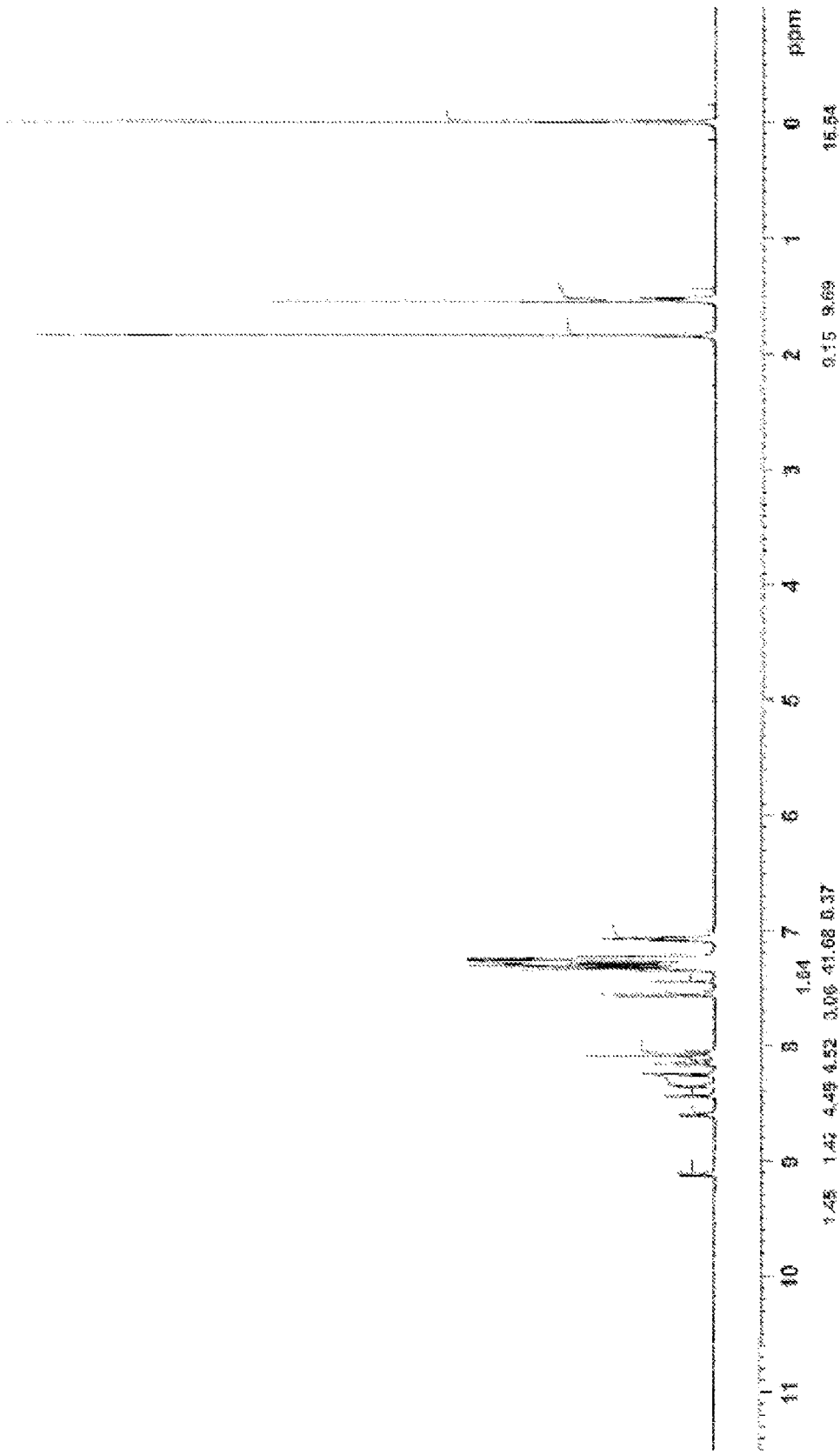

ORGANIC ELECTRIC-FIELD LIGHT-EMITTING ELEMENT, LIGHT-EMITTING MATERIAL FOR ORGANIC ELECTRIC-FIELD LIGHT-EMITTING ELEMENT, AND LIGHT-EMITTING DEVICE, DISPLAY DEVICE, AND ILLUMINATION DEVICE USING SAME ELEMENT

REFERENCE TO RELATED APPLICATIONS

This application is a national stage entry of the international patent application no. PCT/JP2012/064430, filed 5 Jun. 2012, which in turn claims priority benefit from Japanese patent application nos. 2011-134146, filed 16 Jun. 2011, and 2011-212619, filed 28 Sep. 2011, all of which are incorporated by reference herein in their entireties.

TECHNICAL FIELD

The present invention relates to an organic electroluminescent element and an organic electroluminescent element-use material compound used therein. Furthermore, the present invention also relates to a light-emitting device, display device, or illumination device which uses the aforementioned organic electroluminescent element.

BACKGROUND ART

Organic electroluminescent elements (hereinafter also referred to as "elements" or "organic EL elements") emit light at a high brightness and at a low drive voltage and have therefore been the subject of active research and development. An organic electroluminescent element has an organic layer between a pair of electrodes, electrons injected from the cathode and holes injected from the anode are rebonded at the organic layer, and the energy of the excitons thus produced is utilized to emit light. Organic electroluminescent elements can be provided as elements having a variety of emission wavelengths and are expected to find use in a wide range of applications because they have high response speed and are relatively thin and lightweight. In particular, the development of an organic electroluminescent element with high color purity and high luminous efficiency is important in applications to full-color displays and so on, and various research and development results have been reported up to now.

It is described in Patent Document 1 that the use of materials in which rings are formed from pyrene or other condensed ring structures by single bonds or methylene chains or the like as the fluorescent material makes it possible for the element to emit light in the blue region and to have a long service life. In a working example in this literature, three kinds of compounds are used as blue dopants, and Table 6 indicates that the chromaticity is approximately (0.14, 0.16) and that the maximum efficiency is approximately 7.8 cd/A.

Moreover, it is described in publicly known document 2 that the use of a molecule formed by the expansion of condensed rings of benzofluorene as a light-emitting material makes it possible to obtain a high-efficiency element with a wide gap (that is, blue light emission may also be conceivable). The spectrum of a produced element is disclosed in a working example of this literature, showing that the wavelength was also long, it had a broad waveform, and its maximum emission wavelength was an average of approximately 462 nm.

RELATED ART DOCUMENTS

Patent Documents

Patent Document 1: WO 2010/012323
Patent Document 2: Japanese Translation of PCT International Application 2006-512395

SUMMARY OF THE INVENTION

Problems to be Solved by the Invention

However, investigation by the present inventors has revealed that the chromaticity of the organic electroluminescent elements described in the aforementioned Patent Documents 1 and 2 still cannot said to be adequate as a dark blue color for applications in displays and the like, and that light emission of a darker blue color must be realized. In addition, it has also become clear that when these organic electroluminescent elements are used by modulating their brightness, their chromaticity ends up changing accompanying modulation of the emission intensity during driving.

The object of the preset invention is to solve the problems described above. That is, the problem to be solved by the present invention is to provide an organic electroluminescent element which emits dark blue light and in which there is little change in chromaticity during brightness modulation.

Means for Solving the Problems

In view of this, the present inventors conducted diligent investigation aimed at providing an organic electroluminescent element which emits dark blue light and which exhibits little change in chromaticity during brightness modulation.

Here, Patent Document 1 mentions at which position in the pyrene skeleton the ring condensation of a non-aromatic ring is performed, and while it is stated in this document that ring condensation is preferably performed in the direction of the pyrene major axis (positions 1, 2, 3, 6, 7, 8), there is no particular explanation of the reason or the detailed mechanism thereof. Meanwhile, in Patent Document 2, as can be seen by the example compound with a structure in which ring condensation of non-aromatic rings is performed so as to link two molecules in the pyrene's major-axis direction and minor-axis (positions 4, 5, 9, 10) direction being used in [paragraph] [0119], there is no recitation of what position is good as the ring-condensation position with respect to the pyrene skeleton.

In such a situation, the present inventors found the computed structure of the unsubstituted pyrene molecule in terms of the layout of the highest occupied molecular orbital (HOMO) and lowest unoccupied molecular orbital (LUMO) of pyrene. The results thereof are shown in FIG. 4 below. It can be seen from FIG. 4 that there is no difference between the major-axis direction and minor-axis direction of pyrene, and from this as well, the actual situation was that it was inconceivable that the electronic properties would be changed by changing the ring-condensation position on the pyrene skeleton.

For this reason, the reality of the situation was that it was completely impossible to predict from conventional knowledge whether or not an organic electroluminescent element which emits dark blue light and which exhibits little change in chromaticity during brightness modulation can be obtained by changing the structure of pyrene-based compounds. In particular, as recited in Patent Document 1, compounds in which ring condensation is performed in the major-axis direction have been widely used in the past as the ring-condensed pyrene-based compounds, and because it is stated in Patent Document 1 that performing ring condensation in the major-axis direction is preferable, no investigations had been done regarding significantly changing the pyrene ring-condensation position.

Contrary to this, the present inventors have discovered that it is possible to obtain an organic electroluminescent element which emits dark blue light and which exhibits little change in chromaticity during brightness modulation, which could not be achieved in the past, as a result of a pyrene-based compound with a specific structure which is ring-condensed in the minor-axis direction being used as the emission dopant for the element. Furthermore, it was found that the skeleton of the compound with such a structure is such that the skeleton itself emits short-wavelength light, so there is also no need for shifting to a short wavelength by additionally introducing substituents with specific structures into the skeleton, as is done with the conventionally known fluorescent light-emitting materials.

To wit, it was discovered that the use of a pyrene derivative having a specific structure makes it possible to solve the aforementioned problems, which has led to providing the present invention as recited below.

(1) An organic electroluminescent element having a substrate, a pair of electrodes disposed on this substrate and including an anode and a cathode, and a single or a plurality of organic layers disposed between these electrodes, wherein the organic layer(s) include a light-emitting layer, and this light-emitting layer contains a host material and at least one light-emitting material expressed by General Formula 1[1] below:

[First Chemical Formula]

General Formula 1

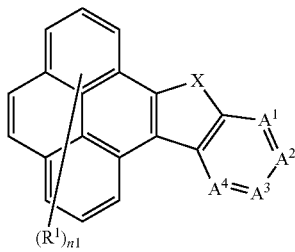

(In General Formula 1, n1 represents an integer from 0 to 8; the $R^1$ [groups] represent each independently a substituent substituted for a hydrogen atom of the pyrene skeleton (however, if n1 is 2 or greater, a case is excluded in which adjacent $R^1$ [groups] are linked to each other to form a saturated or unsaturated ring); X represents $CR^aR^b$ ($R^a$ and $R^b$ represent each independently a hydrogen atom or a substituent, and $R^a$ and $R^b$ may jointly form a five- or six-membered ring), $NR^c$ ($R^c$ represents a hydrogen atom or a substituent), O, S, or $SiR^dR^e$ ($R^d$ and $R^e$ represent each independently a hydrogen atom or a substituent, and $R^d$ and $R^e$ may jointly form a five- or six-membered ring); and $A^1$ to $A^4$ represent each independently either N or $CR^f$ ($R^f$ resents a hydrogen atom or a substituent, and two adjacent $R^f$ [groups] may jointly form a saturated or unsaturated ring, but no more than two rings may be formed jointly by two or more of the $R^f$ [groups]).)

[1] Translator's note: In the Japanese original document, the labeling number for each of the general formulas is indicated in parentheses, but we have omitted the parentheses in the translation to avoid confusion with other parenthetical notations.

(2) The organic electroluminescent element according to (1), wherein $R^a$, $R^b$, $R^d$, and $R^e$ represent each independently an alkyl group, an aryl group, or a heteroaryl group in General Formula 1 above.

(3) The organic electroluminescent element according to (1) or (2), wherein $R^e$ represents a substituent in General Formula 1 above.

(4) The organic electroluminescent element according to any one of (1) to (3), wherein X represents $CR^{a'}R^{b'}$ ($R^{a'}$ and $R^{b'}$ represent each independently an alkyl group, an aryl group, or a heteroaryl group, and $R^{a'}$ and $R^{b'}$ may jointly form a five- or six-membered ring) or $NR^{c'}$ ($R^{c'}$ represents a substituent) in General Formula 1 above.

(5) The organic electroluminescent element according to any one of (1) to (4), wherein $R^1$ has at least one N,N-diarylamino group or an aryl group substituted with an N,N-diarylamino group in General Formula 1 above.

(6) The organic electroluminescent element according to any one of (1) to (5), wherein the light-emitting material expressed by General Formula 1 above is expressed by General Formula 2 below:

[Second Chemical Formula]

General Formula 2

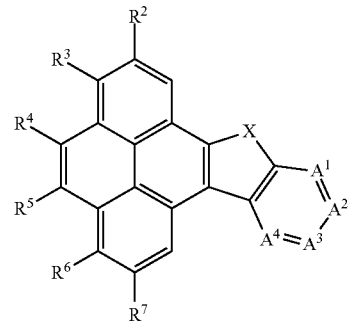

(In General Formula 2, $R^2$ to $R^7$ represent each independently a hydrogen atom or a substituent (however, a case is excluded in which adjacent ones of the $R^2$ to $R^7$ [groups] are linked to each other to form a saturated or unsaturated ring); X represents $CR^aR^b$ ($R^a$ and $R^b$ represent each independently a hydrogen atom or a substituent, and $R^a$ and $R^b$ may jointly form a five- or six-membered ring), $NR^c$ ($R^c$ represents a hydrogen atom or a substituent), O, S, or $SiR^dR^e$ ($R^d$ and $R^e$ represent each independently a hydrogen atom or a substituent, and $R^d$ and $R^e$ may jointly form a five- or six-membered ring); and $A^1$ to $A^4$ represent each independently either N or $CR^f$ ($R^f$ represents a hydrogen atom or a substituent, and two adjacent $R^f$ [groups] may jointly form a saturated or unsaturated ring, but no more than two rings may be formed jointly by two or more of the $R^f$ [groups]).)

(7) The organic electroluminescent element according to any one of (1) to (5), wherein the light-emitting material expressed by General Formula 1 above is expressed by General Formula 3 below:

[Third Chemical Formula]

General Formula 3

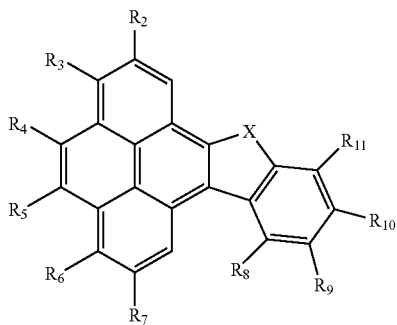

(In General Formula 3, $R^2$ to $R^7$ represent each independently a hydrogen atom or a substituent; however, a case is excluded in which adjacent ones of the $R^2$ to $R^7$ [groups] are linked to each other to form a saturated or unsaturated ring;

X represents $CR^aR^b$ ($R^a$ and $R^b$ represent each independently a hydrogen atom or a substituent, and $R^a$ and $R^b$ may jointly form a five- or six-membered ring), $NR^c$ ($R^c$ represents a hydrogen atom or a substituent), O, S, or $SiR^dR^e$ ($R^d$ and $R^e$ represent each independently a hydrogen atom or a substituent, and $R^d$ and $R^e$ may jointly form a five- or six-membered ring); and $R^8$ to $R^{11}$ represent each independently a hydrogen atom or a substituent, and adjacent two of the $R^8$ to $R^{11}$ [groups] may jointly form a saturated or unsaturated ring, but no more than two rings may be formed jointly by two or more of the $R^8$ to $R^{11}$ [groups].)

(8) The organic electroluminescent element according to any one of (1) to (5), wherein the light-emitting material expressed by General Formula 1 above is expressed by General Formula 4 below:

[Fourth Chemical Formula]

General Formula 4

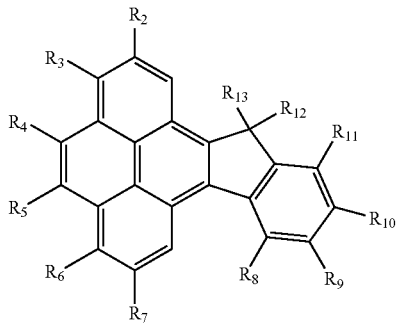

(In General Formula 4, $R^2$ to $R^7$ represent each independently a hydrogen atom or a substituent; however, a case is excluded in which adjacent ones of the $R^2$ to $R^7$ [groups] are linked to each other to form a saturated or unsaturated ring;

$R^8$ to $R^{11}$ represent each independently a hydrogen atom or a substituent, and adjacent two of the $R^8$ to $R^{11}$ [groups] may jointly form a saturated or unsaturated ring, but no more than two rings may be formed jointly by two or more of the $R^8$ to $R^{11}$ [groups]; and $R^{12}$ and $R^{13}$ represent each independently a hydrogen atom or a substituent, and $R^{12}$ and $R^{13}$ may jointly form a five- or six-membered ring.)

(9) The organic electroluminescent element according to any one of (8) [sic][2], wherein at least one of $R^2$ to $R^{11}$ represents a substituent in General Formula 4 above.

[2] Translator's note: apparent error in the original; "according to any one of (8)" should be "according to (8)."

(10) The organic electroluminescent element according to (8), wherein $R^5$ and/or $R^{10}$ represents a substituent in General Formula 4 above.

(11) The organic electroluminescent element according to any one of (1) to (10), wherein the molecular weight of the compound expressed by General Formula 1 above is 800 or less.

(12) The organic electroluminescent element according to any one of (1) to (11), wherein the aforementioned host material contained in the aforementioned light-emitting layer has a hydrocarbon condensed ring structure with a carbon number of 10 to 50.

(13) The organic electroluminescent element according to (12), wherein the aforementioned hydrocarbon condensed ring structure with a carbon number of 10 to 50 of the aforementioned host material is an anthracene skeleton.

(14) The organic electroluminescent element according to any one of (1) to (13), wherein the aforementioned light-emitting layer is formed by a vacuum vapor deposition process.

(15) The organic electroluminescent element according to any one of (1) to (13), wherein the aforementioned light-emitting layer is formed by a wet process.

(16) A light-emitting device which makes use of the organic electroluminescent element according to any one of (1) to (15).

(17) A display device which makes use of the organic electroluminescent element according to any one of (1) to (15).

(18) An illumination device which makes use of the organic electroluminescent element according to any one of (1) to (15).

(19) A light-emitting material for an organic electroluminescent element expressed by General Formula 1 below:

[Fifth Chemical Formula]

General Formula 1

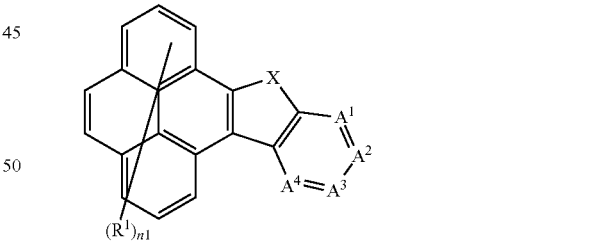

(In General Formula 1, n1 represents an integer from 0 to 8; the $R^1$ [groups] represent each independently a substituent substituted for a hydrogen atom of the pyrene skeleton (however, if n1 is 2 or greater, a case is excluded in which adjacent $R^1$ [groups] are linked to each other to form a saturated or unsaturated ring); X represents $CR^aR^b$ ($R^a$ and $R^b$ represent each independently a hydrogen atom or a substituent, and $R^a$ and $R^b$ may jointly form a five- or six-membered ring), $NR^c$ ($R^c$ represents a hydrogen atom or a substituent), O, S, or $SiR^dR^e$ ($R^d$ and $R^e$ represent each independently a hydrogen atom or a substituent, and $R^d$ and $R^e$ may jointly form a five- or six-membered ring); and $A^1$ to $A^4$ represent each independently either N or $CR^f$ ($R^f$ represents a hydrogen atom or a substituent, and two adjacent R$^f$ [groups] may jointly form a saturated or unsaturated ring, but no more than two rings may be formed jointly by two or more of the R$^f$ [groups]).)

Effects of the Invention

The organic electroluminescent element of the present invention has the advantageous effect of emitting dark blue light and exhibiting little change in chromaticity during brightness modulation. Moreover, the use of the material for the organic electroluminescent element of the present invention makes it possible to easily manufacture such a superior organic electroluminescent element. In addition, the light-emitting device, display device, and illumination device of the present invention have the advantageous effect of low power consumption, excellent chromaticity, and resistance to change in chromaticity during brightness modulation even when used in devices requiring brightness modulation, so they are particularly suitable for application in displays in which light emission at various degrees of brightness is required.

BRIEF DESCRIPTION OF THE DRAWINGS

FIG. 4 is a schematic diagram illustrating the computed structure of unsubstituted pyrene in teens of the layout of (A) the LUMO and (B) the HOMO [molecular] orbitals, respectively.

FIG. 5 is a diagram showing an NMR chart of a compound used in the light-emitting material for use in the organic electroluminescent element of the present invention.

DETAILED DESCRIPTION OF EMBODIMENTS

Figure 1:
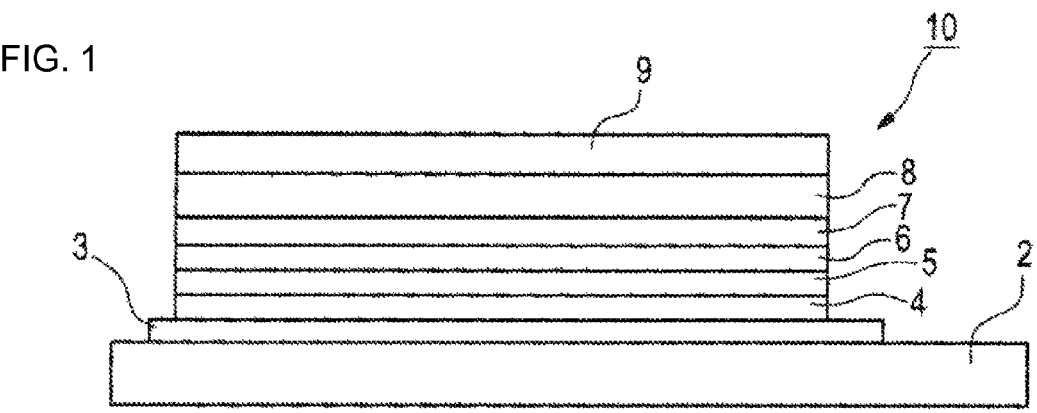
FIG. 1 is a schematic diagram illustrating one example of the configuration of the organic electroluminescent element according to the present invention.

The content of the present invention will be described in detail below. The description of the constituent elements mentioned below may be based on typical embodiments and concrete examples of the present invention, but the present invention is in no way limited to such embodiments or concrete examples. Note that the range of numerical values expressed with the use of [the phrase] "from . . . to . . . " in this Specification means a range which is such that the numerical values given are included as the minimum value and maximum value, respectively.

Light-Emitting Material for an Organic Electroluminescent Element Expressed by General Formula 1

The organic electroluminescent element of the present invention is characterized in that the organic layer(s) constituting the organic electroluminescent element include a light-emitting layer and that this light-emitting layer contains a host material and at least one light-emitting material expressed by General Formula 1 below:

[Sixth Chemical Formula]

General Formula 1

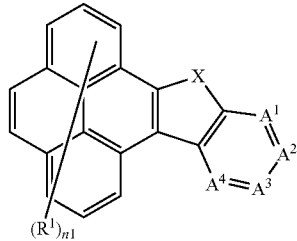

In General Formula 1, n1 represents an integer from 0 to 8, and R$^1$ represents a substituent substituted for a hydrogen atom of the pyrene skeleton (however, if n1 is 2 or greater, a case is excluded in which adjacent R$^1$ [groups] are linked to each other to form a saturated or unsaturated ring). X represents CR$^a$R$^b$ (R$^a$ and R$^b$ represent each independently a hydrogen atom or a substituent, and R$^a$ and R$^b$ may jointly form a five- or six-membered ring), NR$^c$ (R$^c$ represents a hydrogen atom or a substituent), O, S, or SiR$^d$R$^e$ (R$^d$ and R$^e$ represent each independently a hydrogen atom or a substituent, and R$^d$ and R$^e$ may jointly form a five- or six-membered ring). A$^1$ to A$^4$ represent each independently either N or CR$^f$ (R$^f$ represents a hydrogen atom or a substituent, and two adjacent R$^f$ [groups] may jointly form a saturated or unsaturated ring, but no more than two rings may be formed jointly by two or more of the R$^f$ [groups]).

The organic electroluminescent element of the present invention uses a light-emitting material for an organic electroluminescent element expressed by General Formula 1 above (hereinafter also referred to as "light-emitting material expressed by General Formula 1," "light-emitting material of the present invention," or "compound of the present invention") as a light-emitting material.

Here, when the organic electroluminescent element is driven, the voltage applied is different depending on whether the brightness is low or the brightness is high. In an electroluminescent element using an organic layer, it is common for the voltage dependence of the speed of transport of electrons to be different from the voltage dependence of the speed of transport of holes. It is thought that, for this reason, if the applied voltage is different, the relative difference between the electron transport speed and the hole transport speed changes, and the positions at which rebinding occurs within the light-emitting layer become different. An organic electroluminescent element is a laminated body of a plurality of organic layers, so if the positions of light emission are different, the effects of interference between light emissions that are reflected from the interfaces between the various layers are also different. Here, it is thought that if the spectrum is broad or if peaks other than the main peak are present, the components on the long-wave side are strengthened by interference, which makes the chromaticity not constant.

In contrast, an organic electroluminescent element using the compound of the present invention as the light-emitting material gives light emission with a purer blue color than those that use conventionally known similar compounds. Although no particular theory holds sway, the reason for this, in addition to the shift to shorter wavelengths which was unpredictable from molecular orbital calculations, may be the fact that the spectral shape became sharper. It was found that the spectral shape being sharp (a shape in which the half-value width is narrow, and the peaks other than the main peak are small) and other factors further reduce the change in chromaticity between when driven at low brightness and when driven at high brightness to extremely small change.

Furthermore, a shift to shorter wavelength due to substituents is synonymous with instability of the compound, giving rise to a decrease in durability due to the rupture of substituents in many cases. For this reason, a shift to shorter wavelength of the parent skeleton or a change to a narrow spectrum has been desired.

With respect to this, with the light-emitting material for an organic electroluminescent element expressed by General Formula 1 above, its parent skeleton itself contributes to a shift to shorter wavelength and suppression of the change in chromaticity during brightness modulation. For this reason, with the light-emitting material expressed by General Formula 1 above, the aforementioned effects can be obtained with virtually no limitation on the substituents of its parent skeleton. However, in a preferred mode of the present invention, specific substituents may be used to further improve a shift to lower wavelengths and suppression of the change in chromaticity when brightness is modulated.

The light-emitting material expressed by General Formula 1 will be described in detail below.

In the present invention, a hydrogen atom in the description of General Formula 1 above also includes an isotope [of hydrogen] (such as a deuterium atom), and atoms further constituting a substituent also encompass isotopes thereof.

In the present invention, when the term "substituent" is used, that substituent may be further substituted. For example, when "alkyl group" is referred to in the present invention, it encompasses alkyl groups that have been substituted with a fluorine atom (such as a trifluoromethyl group), alkyl groups that have been substituted with an aryl group (such as a triphenylmethyl group), and so forth, and when the term "$C_1$ to $C_6$ alkyl group" is used, this indicates that the carbon number is from 1 to 6 for the entire group, including one that has been substituted.

In General Formula 1, X represents $CR^aR^b$, $NR^c$, O, S, or $SiR^dR^e$.

In $CR^aR^b$, its carbon atom is a constituent atom of a ring of the compound expressed by General Formula 1, and $R^a$ and $R^b$ [each] represent a hydrogen atom or a substituent bonded to this carbon atom. $R^a$ and $R^b$ may be the same or different. Moreover, $R^a$ and $R^b$ may jointly form a five- or six-membered ring.

In $NR^c$, its nitrogen atom is a constituent atom of a ring of the compound expressed by General Formula 1, and $R^c$ represents a hydrogen atom or a substituent bonded to this nitrogen atom. $R^c$ is preferably a substituent.

In $SiR^dR^e$, its silicon atom is a constituent atom of a ring of the compound expressed by General Formula 1, and $R^d$ and $R^e$ [each] represent a hydrogen atom or a substituent bonded to this silicon atom. $R^d$ and $R^e$ may be the same or different. In addition, $R^d$ and $R^e$ may jointly form a five- or six-membered ring.

[Examples of] $R^a$, $R^b$, $R^d$, and $R^e$ (a substituent on a carbon atom and a substituent on a silicon atom) include [the substituents in] Substituent Group A below:

<<Substituent Group A>>

Examples [of Substituent Group A] include alkyl groups (preferably with a carbon number of 1 to 30, more preferably with a carbon number of 1 to 20, and especially preferably with a carbon number of 1 to 10, such as methyl, ethyl, isopropyl, t-butyl, n-octyl, n-decyl, n-hexadecyl, cyclopropyl, cyclopentyl, and cyclohexyl); alkenyl groups (preferably with a carbon number of 2 to 30, more preferably with a carbon number of 2 to 20, and especially preferably with a carbon number of 2 to 10, such as vinyl, allyl, 2-butenyl, and 3-pentenyl); alkynyl groups (preferably with a carbon number of 2 to 30, more preferably with a carbon number of 2 to 20, and especially preferably with a carbon number of 2 to 10, such as propargyl and 3-pentynyl); aryl groups (preferably with a carbon number of 6 to 30, more preferably with a carbon number of 6 to 20, and especially preferably with a carbon number of 6 to 12, such as phenyl, p-methylphenyl, naphthyl, and anthranil); amino groups (preferably with a carbon number of 0 to 30, more preferably with a carbon number of 0 to 20, and especially preferably with a carbon number of 0 to 10, such as amino, methylamino, dimethylamino, diethylamino, dibenzylamino, diphenylamino, and ditolylamino); alkoxy groups (preferably with a carbon number of 1 to 30, more preferably with a carbon number of 1 to 20, and especially preferably with a carbon number of 1 to 10, such as methoxy, ethoxy, butoxy, and 2-ethylhexyloxy); aryloxy groups (preferably with a carbon number of 6 to 30, more preferably with a carbon number of 6 to 20, and especially preferably with a carbon number of 6 to 12, such as phenyloxy, 1-naphthyloxy, and 2-naphthyloxy); heterocyclic oxy groups (preferably with a carbon number of 1 to 30, more preferably with a carbon number of 1 to 20, and especially preferably with a carbon number of 1 to 12, such as pyridyloxy, pyrazyloxy, pyrimidyloxy, and quinolyloxy); acyl groups (preferably with a carbon number of 2 to 30, more preferably with a carbon number of 2 to 20, and especially preferably with a carbon number of 2 to 12, such as acetyl, benzoyl, formyl, and pivaloyl); alkoxycarbonyl groups (preferably with a carbon number of 2 to 30, more preferably with a carbon number of 2 to 20, and especially preferably with a carbon number of 2 to 12, such as methoxycarbonyl and ethoxycarbonyl); aryloxycarbonyl groups (preferably with a carbon number of 7 to 30, more preferably with a carbon number of 7 to 20, and especially preferably with a carbon number of 7 to 12, such as phenyloxycarbonyl); acyloxy groups (preferably with a carbon number of 2 to 30, more preferably with a carbon number of 2 to 20, and especially preferably with a carbon number of 2 to 10, such as acetoxy and benzoyloxy); acylamino groups (preferably with a carbon number of 2 to 30, more preferably with a carbon number of 2 to 20, and especially preferably with a carbon number of 2 to 10, such as acetylamino and benzoylamino); alkoxycarbonylamino groups (preferably with a carbon number of 2 to 30, more preferably with a carbon number of 2 to 20, and especially preferably with a carbon number of 2 to 12, such as methoxycarbonylamino); aryloxycarbonylamino groups (preferably with a carbon number of 7 to 30, more preferably with a carbon number of 7 to 20, and especially preferably with a carbon number of 7 to 12, such as phenyloxycarbonylamino); sulfonyl amino groups (preferably with a carbon number of 1 to 30, more preferably with a carbon number of 1 to 20, and especially preferably with a carbon number of 1 to 12, such as methanesulfonyl amino and benzenesulfonyl amino); sulfamoyl groups (preferably with a carbon number of 0 to 30, more preferably with a carbon number of 0 to 20, and especially preferably with a carbon number of 0 to 12, such as sulfamoyl, methylsulfamoyl, dimethylsulfamoyl, and phenylsulfamoyl); carbamoyl groups (preferably with a carbon number of 1 to 30, more preferably with a carbon number of 1 to 20, and especially preferably with a carbon number of 1 to 12, such as carbamoyl, methylcarbamoyl, diethylcarbamoyl, and phenylcarbamoyl); alkylthio groups (preferably with a carbon number of 1 to 30, more preferably with a carbon number of 1 to 20, and especially preferably with a carbon number of 1 to 12, such as methylthio and ethylthio); arylthio groups (preferably with a carbon number of 6 to 30, more preferably with a carbon number of 6 to 20, and especially preferably with a carbon number of 6 to 12, such as phenylthio); heterocyclic thio groups (preferably with a carbon number of 1 to 30, more preferably with a carbon number of 1 to 20, and especially preferably with a carbon number of 1 to 12, such as pyridylthio, 2-benzimizolylthio, 2-benzoxazolylthio, and 2-benzothiazolylthio); sulfonyl groups (preferably with a carbon number of 1 to 30, more preferably with a carbon number of 1 to 20, and especially preferably with a carbon number of 1 to 12, such as mesyl and tosyl); sulfinyl groups (preferably with a carbon number of 1 to 30, more preferably with a carbon number of 1 to 20, and especially preferably with a carbon number of 1 to 12, such as methanesulfinyl and benzenesulfinyl); ureido groups (preferably with a carbon number of 1 to 30, more preferably with a carbon number of 1 to 20, and especially preferably with a carbon number of 1 to 12, such as ureido, methylureido, and phenylureido); phosphoric amide groups (preferably with a carbon number of 1 to 30, more preferably with a carbon number of 1 to 20, and especially preferably with a carbon number of 1 to 12, such as diethylphosphoramide and phenylphosphoramide); a hydroxy group; a mercapto group; halogen atoms (such as a fluorine atom, chlorine atom, bromine atom, and iodine atom); a cyano group; a sulfo group; a carboxyl group; a nitro group; a hydroxamic acid group; a sulfino group; a hydrazino group; an imino group; heterocyclic groups (also including aromatic heterocyclic groups, preferably with a carbon number of 1 to 30 and more preferably with a carbon number of 1 to 12, with examples of the hetero atom including a nitrogen atom, an oxygen atom, a sulfur atom, a phosphorus atom, a silicon atom, a selenium atom, and a tellurium atom, and with concrete examples including pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, azepinyl group, and silolyl group); silyl groups (preferably with a carbon number of 3 to 40, more preferably with a carbon number of 3 to 30, and especially preferably with a carbon number of 3 to 24, such as trimethylsilyl and triphenylsilyl); silyloxy groups (preferably with a carbon number of 3 to 40, more preferably with a carbon number of 3 to 30, and especially preferably with a carbon number of 3 to 24, such as trimethylsilyloxy and triphenylsilyloxy); and phosphoryl groups (such as a diphenylphosphoryl group and a dimethylphosphoryl group). These substituents may be further substituted, and examples of the further substituent include groups selected from the Substituent Group A described above. Furthermore, the substituents that have been substituted with a substituent may be further substituted, and examples of the further substituents include groups selected from the Substituent Group A described above. Moreover, the substituents that substitute for substituents that substitute for substituents may be further substituted, and examples of the further substituents include groups selected from the aforementioned Substituent Group A.

It is preferable for $R^a$, $R^b$, $R^d$, and $R^e$ to be each independently an alkyl group, an aryl group, a heteroaryl group, a perfluoroalkyl group, an alkoxy group, or a fluorine atom, with an alkyl group, an aryl group, or a heteroaryl group being more preferable. It is especially preferable for $R^a$, $R^b$, $R^d$, and $R^e$ to be each independently a $C_1$ to $C_{10}$ linear, branched, or cyclic alkyl group, a $C_6$ to $C_{14}$ aryl group, or a $C_5$ to $C_{20}$ heteroaryl group that includes at least one of N, O, and S as a hetero atom, with a $C_1$ to $C_6$ linear or branched alkyl group being even more especially preferable. In addition, from the standpoint of ease of synthesis, it is preferable for $R^a$ and $R^b$ to be the same substituent. Furthermore, it is preferable for $R^d$ and $R^e$ to be the same substituent from the same standpoint.

[Examples of] $R^c$ (a substituent on a nitrogen atom) include [the substituents in] Substituent Group B below:

<<Substituent Group B>>

[Examples of Substituent Group B include]alkyl groups (preferably with a carbon number of 1 to 30, more preferably with a carbon number of 1 to 20, and especially preferably with a carbon number of 1 to 10, such as methyl, ethyl, isopropyl, t-butyl, n-octyl, n-decyl, n-hexadecyl, cyclopropyl, cyclopentyl, and cyclohexyl); alkenyl groups (preferably with a carbon number of 2 to 30, more preferably with a carbon number of 2 to 20, and especially preferably with a carbon number of 2 to 10, such as vinyl, allyl, 2-butenyl, and 3-pentenyl); alkynyl groups (preferably with a carbon number of 2 to 30, more preferably with a carbon number of 2 to 20, and especially preferably with a carbon number of 2 to 10, such as propargyl and 3-pentynyl); aryl groups (preferably with a carbon number of 6 to 30, more preferably with a carbon number of 6 to 20, and especially preferably with a carbon number of 6 to 12, such as phenyl, p-methylphenyl, naphthyl, and anthranil); a cyano group; heterocyclic groups (also including aromatic heterocyclic groups, preferably with a carbon number of 1 to 30 and more preferably with a carbon number of 1 to 12, with examples of the hetero atom including a nitrogen atom, an oxygen atom, a sulfur atom, a phosphorus atom, a silicon atom, a selenium atom, and a tellurium atom, and with concrete examples including pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, azepinyl group, and silolyl group). These substituents may be further substituted, and examples of the further substituent include groups selected from the Substituent Group B described above. Moreover, the substituents that have been substituted with a substituent may be further substituted, and examples of the further substituents include groups selected from the Substituent Group B described above. In addition, the substituents that substitute for substituents that substitute for substituents may be further substituted, and examples of the further substituents include groups selected from the aforementioned Substituent Group B.

$R^c$ is preferably an alkyl group, a perfluoroalkyl group, an aryl group, or a fluorine atom. $R^c$ is preferably a $C_1$ to $C_{10}$ linear, branched, or cyclic alkyl group, a $C_6$ to $C_{50}$ aryl group, or a $C_5$ to $C_{20}$ heteroaryl group that includes at least one of N, O, and S as a hetero atom. $R^c$ is more preferably a $C_6$ to $C_{14}$ aryl group or a $C_5$ to $C_{20}$ heteroaryl group that includes at least one of N, O, and S as a hetero atom.

[Each pair of] $R^a$ and $R^b$, and $R^d$ and $R^e$ may jointly form a five- or six-membered ring. The five- or six-membered ring that is formed may be a cycloalkyl ring, a cycloalkenyl ring, or a heterocycle. A ring that includes one to three hetero atoms selected from a group comprising a nitrogen atom, an oxygen atom, and a sulfur atom in the atoms constituting the ring can be cited as an example of hetero rings. The five- or six-membered ring that is formed may have a substituent, and [those listed in] the aforementioned Substituent Group A can be cited as examples of substituents on a carbon atom, while [those listed in] the aforementioned Substituent Group B can be cited as examples of substituents on a nitrogen atom.

In the present invention, X in General Formula 1 above is preferably $CR^aR^b$, $NR^c$, or O, with either $CR^aR^b$ or $NR^c$ being more preferable from the standpoint of emission color. If X is either $CR^aR^b$ or $NR^c$, as seen in General Formula 2 (described later), General Formula 1 above is especially preferably such that the position adjacent to $R^2$ on the side opposite from $R^3$ is a hydrogen atom in a ring that has $R^2$ and $R^3$ of the pyrene skeleton. By adopting such a structure, the hydrogen atom in the vicinity of X on the pyrene skeleton and the substituent $R^a$, $R^b$, or $R^c$ represented by X repel [each other], causing the planarity to be decreased, thus making it possible to shift the emission wavelength to a shorter wavelength.

In the present invention, furthermore, it is especially preferable if X is $CR^{a'}R^{b'}$ ($R^{a'}$ and $R^{b'}$ represent each independently an alkyl group, an aryl group, or a heteroaryl group, and $R^{a'}$ and $R^{b'}$ may jointly form a five- or six-membered ring) or $NR^{c'}$ ($R^{c'}$ represents a substituent), with $CR^{a'}R^{b'}$ being even more especially favorable.

$A^1$ to $A^4$ in General Formula 1 represent each independently either $CR^f$ or N. The number of N in $A^1$ to $A^4$ is preferably from 0 to 2, [more] preferably 0 or 1, and especially preferably 0. That is, a case in which $A^1$ to $A^4$ are all $CR^f$ can be cited as a preferred example.

$CR^f$ is such that its carbon atom is a constituent atom of a ring of the light-emitting material expressed by General Formula 1, while $R^f$ represents a hydrogen atom or a substituent bonded to this carbon atom. Examples of $R^f$ include [those listed in] the aforementioned Substituent Group A. $R^f$ represents an alkyl group (more preferably a $C_1$ to $C_{10}$ linear, branched, or cyclic alkyl group), an aryl group (more preferably a $C_6$ to $C_{14}$ aryl group), a heteroaryl group (preferably a $C_5$ to $C_{20}$ heteroaryl group that includes N, O, or S as a hetero atom), a di-substituted amino group (more preferably a dialkylamino group or diarylamino group, with the preferred ranges of the alkyl group and aryl group in this case being the same as the preferred ranges of the alkyl group and aryl group in $R^1$), a halogeno group (preferably a fluoro group), a cyano group, or a nitro group.

Moreover, $R^f$ may be substituted with any one or more substituents, and the preferred ranges of the substituent(s) in this case are the same as those for $R^1$.

At least one $R^f$ [group] is more preferably a substituent having a substituted or unsubstituted alkyl group, a substituted or unsubstituted aryl group, or a di-substituted amino group, especially preferably a substituent having a substituted aryl group or a di-substituted amino group, and even more especially preferably a substituent having an N,N-diarylamino group or an aryl group substituted with an N,N-diarylamino group or alkyl group. To wit, it is even more especially preferable if at least one $R^f$ [group] is a group expressed by General Formula Hp-1, Hp-2, or Hp-3 below:

[Seventh Chemical Formula]

General Formula Hp-1

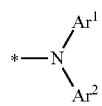

(In General Formula Hp-1, $Ar^1$ and $Ar^2$ represent each independently an aryl group.)

[Eight Chemical Formula]

General Formula Hp-2

(In General Formula Hp-2, $Ar^3$ represents an arylene group, and $Ar^4$ and $Ar^5$ represent each independently an aryl group.)

[Ninth Chemical Formula]

General Formula Hp-3

(In General Formula Hp-3, $Ar^6$ represents an aryl group, $R^h$ represents a $C_1$ to $C_6$ alkyl group, and $n^h$ represents an integer from 1 to 4.)

In General Formulas Hp-1 and Hp-2, $Ar^1$, $Ar^2$, $Ar^4$, and $Ar^5$ are preferably each independently a substituted or unsubstituted phenyl group or a substituted or unsubstituted naphthyl group, with a substituted or unsubstituted phenyl group being more preferable.

In General Formula Hp-2, $Ar^3$ is preferably a substituted or unsubstituted phenylene group or a substituted or unsubstituted naphthylene group, with substituted or unsubstituted phenylene being more preferable, and substituted or unsubstituted p-phenylene being especially preferable.

In General Formula Hp-3, $Ar^6$ is preferably a substituted or unsubstituted phenylene group or a substituted or unsubstituted naphthylene group, with a substituted or unsubstituted phenylene group being more preferable. $R^h$ is preferably methyl, isopropyl, n-butyl, isobutyl, t-butyl, isopentyl, or neopentyl, with methyl, isopropyl, or t-butyl being more preferable.

When two or more of $A^1$ to $A^4$ in General Formula 1 represent $CR^f$, two adjacent $CR^f$ [groups] of these may jointly form a saturated or unsaturated ring, but no more than two rings may be formed jointly by two or more of the $R^f$ [groups]. When two or more $R^f$ [groups] jointly form a ring, the ring that is formed is preferably a substituted or unsubstituted benzene ring and [more] preferably an unsubstituted benzene ring.

The following partial structures can be cited as examples of the case of $R^f$ [groups] forming a ring, but the present invention is not limited to or by the following examples of partial structures. Furthermore, the description and preferred ranges of $R^2$ to $R^7$ in the following partial structures are the same as the description and preferred ranges of $R^2$ to $R^7$ in General Formula 2 (described later), and the description and preferred ranges of X in the following partial structures are the same as the description and preferred ranges of X in General Formula 1 above.

[Tenth Chemical Formula]

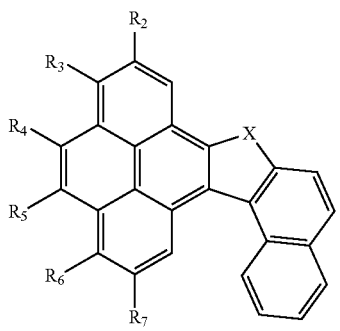

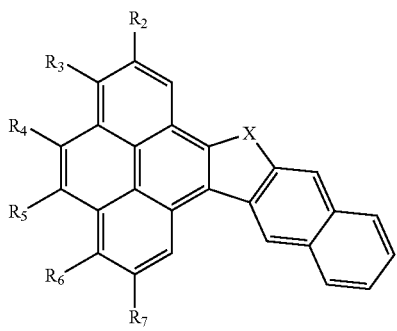

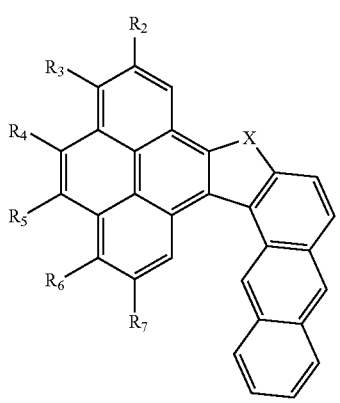

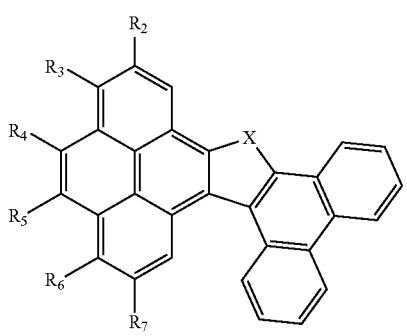

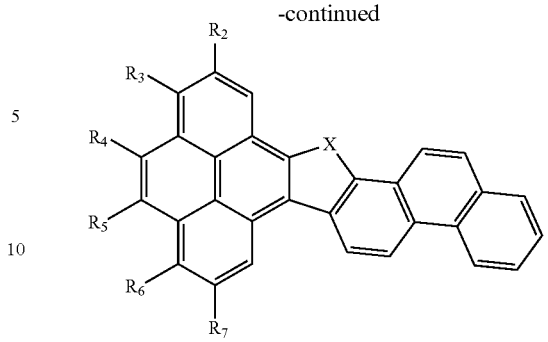

-continued n1 in General Formula 1 represents an integer from 0 to 8, preferably from 0 to 7, more preferably from 0 to 6, especially preferably from 1 to 4, even more especially preferably 1 or 2, and yet more preferably 2.

The $R^1$ [groups] in General Formula 1 represent each independently a substituent substituted for a hydrogen atom of the pyrene skeleton (however, if n1 is 2 or greater, a case is excluded in which adjacent $R^1$ [groups] are linked to each other to form a saturated or unsaturated ring). Examples of substituents include [those listed in] the aforementioned Substituent Group A. Of those, [$R^1$] represents an alkyl group (more preferably a $C_1$ to $C_{10}$ linear, branched, or cyclic alkyl group), an aryl group (more preferably a $C_6$ to $C_{14}$ aryl group), a heteroaryl group (preferably a $C_5$ to $C_{20}$ heteroaryl group that includes N, O, or S as a hetero atom), a di-substituted amino group (more preferably a dialkylamino group or diarylamino group, with the preferred ranges of the alkyl group and aryl group in this case being the same as the preferred ranges of the alkyl group and aryl group in $R^1$), a halogeno group (preferably a fluoro group), a cyano group, or a nitro group.

Moreover, $R^1$ may be substituted with any one or more substituents, and the preferred ranges of the substituent(s) in this case are the same as those for $R^1$. If n1 is 2 or greater, adjacent $R^1$ [groups] will not be linked to each other to form a ring. The "ring" referred to here include both a case in which an aromatic ring or a heterocycle is newly condensed and a case in which a non-aromatic ring such as the following group (Het) is formed.

Group (Het)

[Eleventh Chemical Formula]

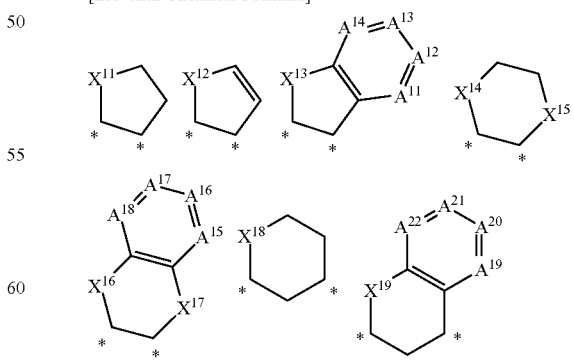

In the group (Het) above, the description and preferred ranges of $X^{11}$ to $X^{19}$ are the same as the description and preferred ranges of X in General Formula 1 above, and the description and preferred ranges of $A^{11}$ to $A^{22}$ are the same as the description and preferred ranges of $A^1$ to $A^4$ in General Formula 1 above.

It is more preferable for at least one $R^1$ [group] to be a substituent having a substituted or unsubstituted alkyl group, a substituted or unsubstituted aryl group, or a di-substituted amino group; having a substituted aryl group or a di-substituted amino group is especially preferable, and having an N,N-diarylamino group or an aryl group substituted with an N,N-diarylamino group is even more especially preferable. To wit, it is even more especially preferable for at least one $R^1$ [group] to be a group expressed by General Formula Hp-1 above or General Formula Hp-2 above.

The light-emitting material expressed by General Formula 1 above is preferably a compound expressed by General Formula 2 below:

[Twelfth Chemical Formula]

General Formula 2

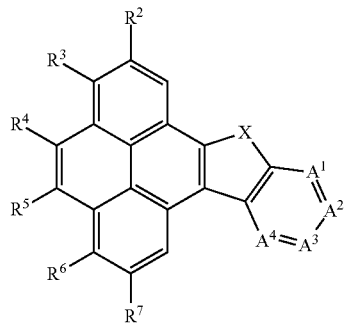

In General Formula 2, $R^2$ to $R^7$ represent each independently a hydrogen atom or a substituent (however, a case is excluded in which adjacent ones of the $R^2$ to $R^7$ [groups] are linked to each other to form a saturated or unsaturated ring). X represents $CR^aR^b$ ($R^a$ and $R^b$ represent each independently a hydrogen atom or a substituent, and $R^a$ and $R^b$ may jointly form a five- or six-membered ring), $NR^c$ ($R^c$ represents a hydrogen atom or a substituent), O, S, or $SiR^dR^e$ ($R^d$ and $R^e$ represent each independently a hydrogen atom or a substituent, and $R^d$ and $R^e$ may jointly form a five- or six-membered ring). $A^1$ to $A^4$ represent each independently either N or $CR^f$ ($R^f$ represents a hydrogen atom or a substituent, and adjacent two $R^f$ [groups] may jointly form a saturated or unsaturated ring, but no more than two rings may be formed jointly by two or more of the $R^f$ [groups]).

The description and preferred ranges of $R^2$ to $R^7$ in General Formula 2 are the same as the description and preferred ranges of $R^1$ in General Formula 1. The description and preferred ranges of X in General Formula 2 are the same as the description and preferred ranges of X in the description of General Formula 1. The description and preferred ranges of $A^1$ to $A^4$ in General Formula 2 are the same as the description and preferred ranges of $A^1$ to $A^4$ in the description of General Formula 1.

The light-emitting material expressed by General Formula 1 above is preferably a compound expressed by General Formula 3 below:

[Thirteenth Chemical Formula]

General Formula 3

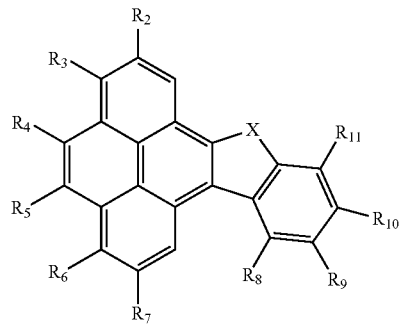

In General Formula 3, $R^2$ to $R^7$ represent each independently a hydrogen atom or a substituent. However, a case is excluded in which adjacent ones of the $R^2$ to $R^7$ [groups] are linked to each other to form a saturated or unsaturated ring.

X represents $CR^aR^b$ ($R^a$ and $R^b$ represent each independently a hydrogen atom or a substituent, and $R^a$ and $R^b$ may jointly form a five- or six-membered ring), $NR^c$ ($R^c$ represents a hydrogen atom or a substituent), O, S, or $SiR^dR^e$ ($R^d$ and $R^e$ represent each independently a hydrogen atom or a substituent, and $R^d$ and $R^e$ may jointly form a five- or six-membered ring).

$R^8$ to $R^{11}$ represent each independently a hydrogen atom or a substituent, and adjacent two of the $R^8$ to $R^{11}$ [groups] may jointly form a saturated or unsaturated ring, but no more than two rings may be formed jointly by two or more of the $R^8$ to $R^{11}$ [groups].

The description and preferred ranges of $R^2$ to $R^7$ in General Formula 3 are the same as the description and preferred ranges of $R^1$ in General Formula 1. The description and preferred ranges of X in General Formula 3 are the same as the description and preferred ranges of X in the description of General Formula 1. The description and preferred ranges of $R^8$ to $R^{11}$ in General Formula 3 are the same as the description and preferred ranges of $R^f$ in the description of General Formula 1.

The light-emitting material expressed by General Formula 1 above is preferably a compound expressed by General Formula 4 below:

[Fourteenth Chemical Formula]

General Formula 4

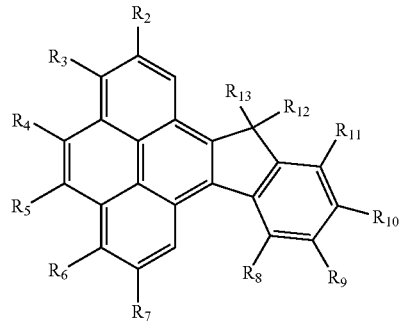

In General Formula 4, $R^2$ to $R^7$ represent each independently a hydrogen atom or a substituent. However, a case is excluded in which adjacent ones of the $R^2$ to $R^7$ [groups] are linked to each other to form a saturated or unsaturated ring.

$R^8$ to $R^{11}$ represent each independently a hydrogen atom or a substituent, and adjacent two of the $R^8$ to $R^{11}$ [groups] may jointly form a saturated or unsaturated ring, but no more than two rings may be formed jointly by two or more of the $R^8$ to $R^{11}$ [groups].

$R^{12}$ and $R^{13}$ represent each independently a hydrogen atom or a substituent, and $R^{12}$ and $R^{13}$ may jointly form a five- or six-membered ring.

With the light-emitting material of the present invention, it is preferable for at least one of $R^2$ to $R^{11}$ in General Formula 4 above to represent a substituent (other than a hydrogen atom or a deuterium atom), it is especially preferable for at least one of $R^3$, $R^5$, $R^6$, and $R^{10}$ to represent a substituent, and it is especially preferable for $R^5$ and/or $R^{10}$ to represent a substituent. In addition, the description and preferred ranges of $R^2$ to $R^7$ in General Formula 4 are the same as the description and preferred ranges of $R^1$ in General Formula 1. The description and preferred ranges of $R^8$ to $R^{11}$ in General Formula 4 are the same as the description and preferred ranges of $R^f$ in the description of General Formula 1. The description and preferred ranges of $R^{12}$ and $R^{13}$ in General Formula 4 are the same as the description and preferred ranges of $R^a$ and $R^b$ in the description of General Formula 1.

The maximum emission wavelength of the organic electroluminescent element in which the light-emitting material expressed by General Formula 1 is used is generally from 400 to 480 nm, preferably from 420 to 470 nm, and more preferably from 430 to 460 nm. In the present invention, it is preferable to use a compound expressed by [any of] General Formulas 2 to 4, in particular, as the compound expressed by General Formula 1 because the maximum emission wavelength of the organic electroluminescent element is from 430 to 460 nm, and blue light with particularly high color purity can be emitted. The maximum emission wavelength of an organic electroluminescent element in which the light-emitting material expressed by General Formula 1 is used is most preferably at least 440 nm and less than 455 nm from the standpoint of obtaining blue light emission of high color purity.

The light-emitting material expressed by General Formula 1 preferably has a molecular weight of 800 or less, more preferably 700 or less, and even more preferably 600 or less. Lowering the molecular weight allows the sublimation temperature to be lowered, so pyrolysis of the compound in vapor deposition can be prevented. Furthermore, this makes it possible to shorten the vapor deposition time and to suppress energy required for vapor deposition.

Concrete examples of the light-emitting material expressed by General Formula 1 will be given below, but it should not be construed that the light-emitting material expressed by General Formula 1 that can be used in the present invention are limited to or by these concrete examples:

[Fifteenth Chemical Formula]

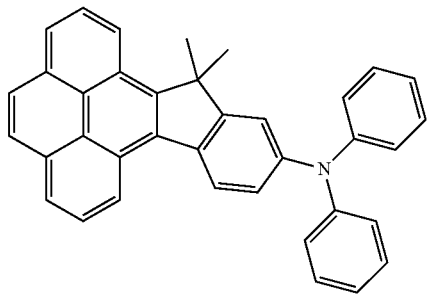

[Sixteenth Chemical Formula]

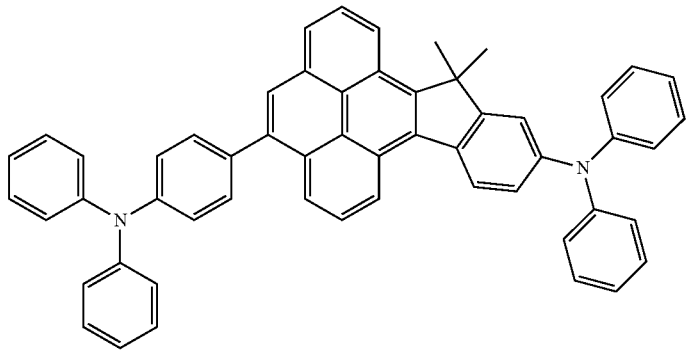

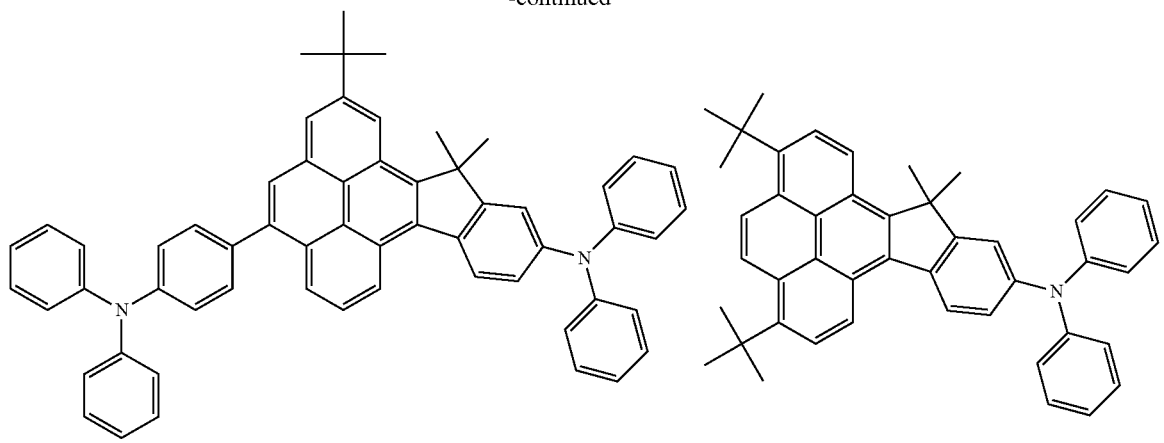
[Seventeenth Chemical Formula]
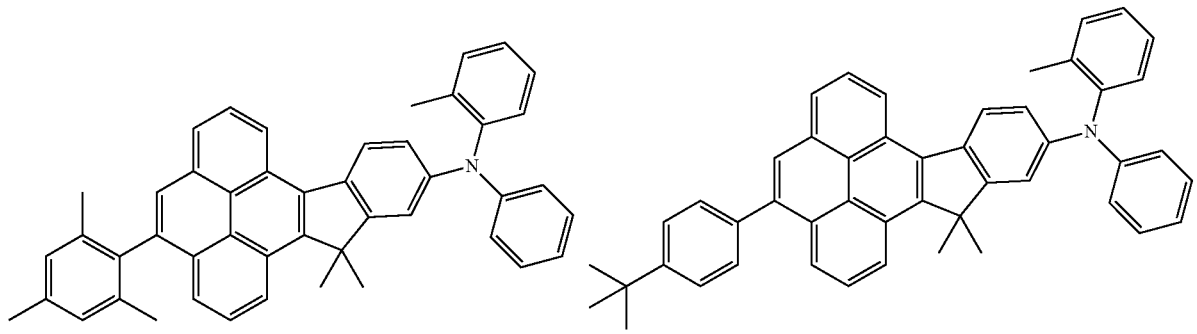
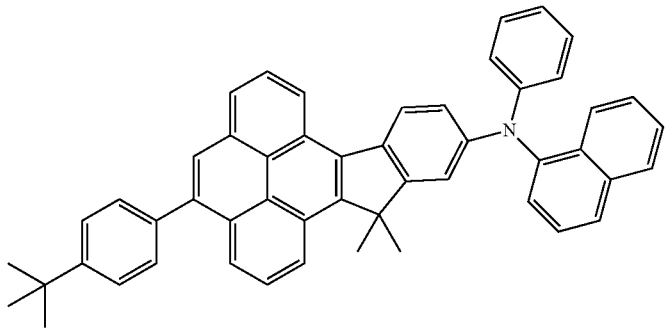
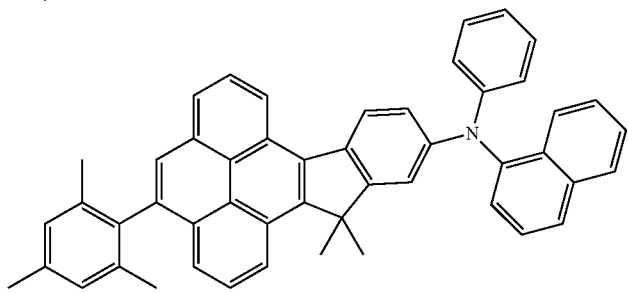
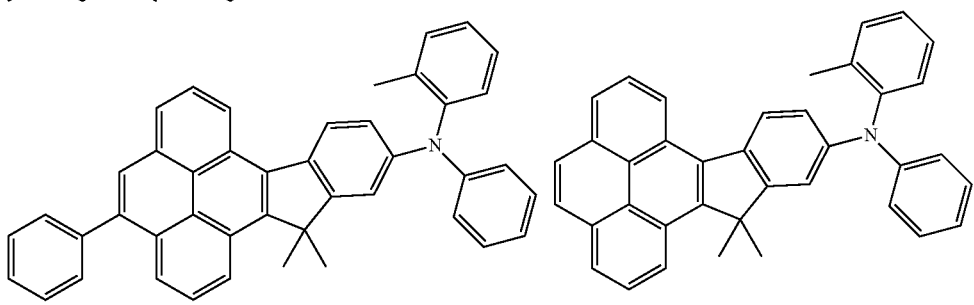

-continued
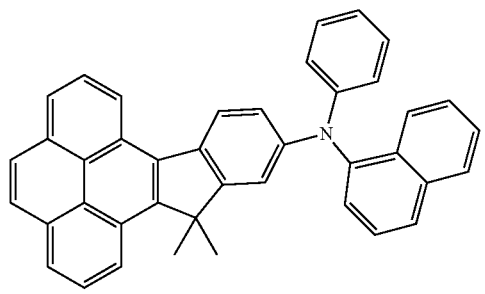
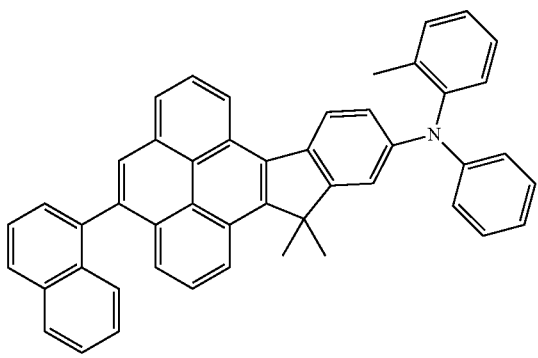
[Eighteenth Chemical Formula]
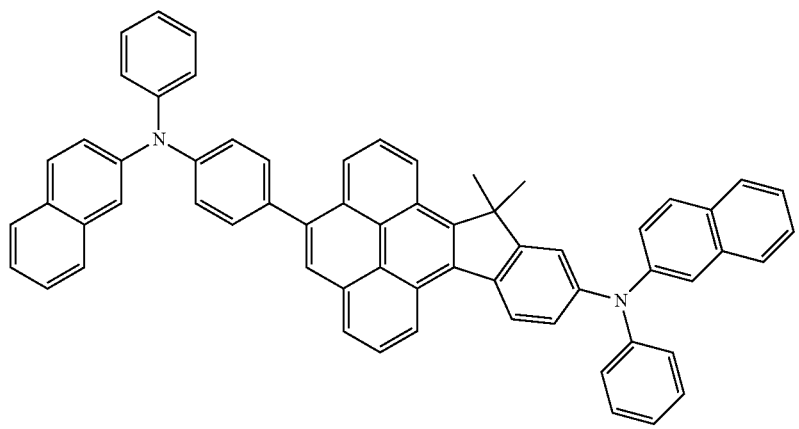
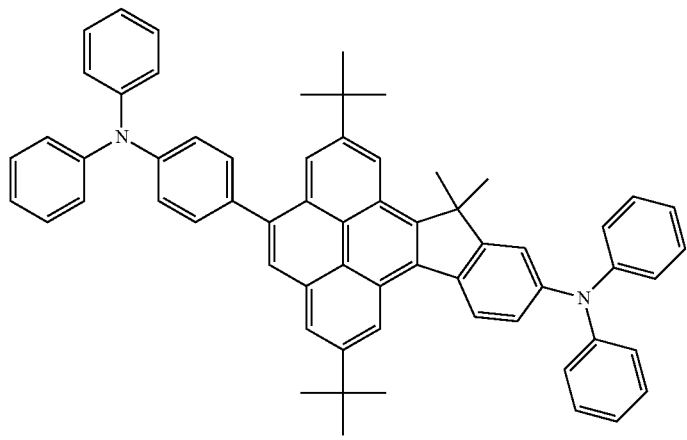
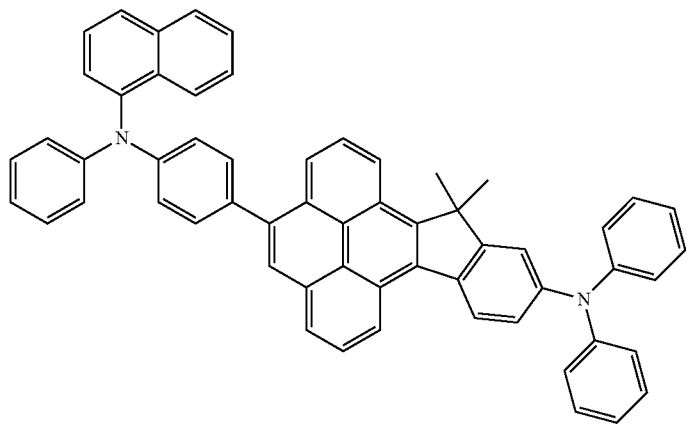

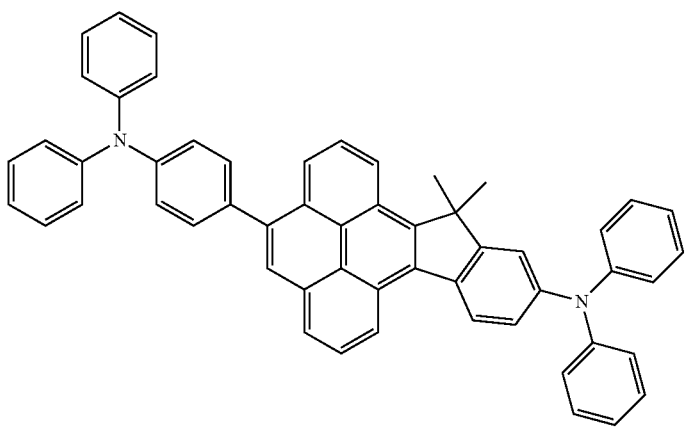
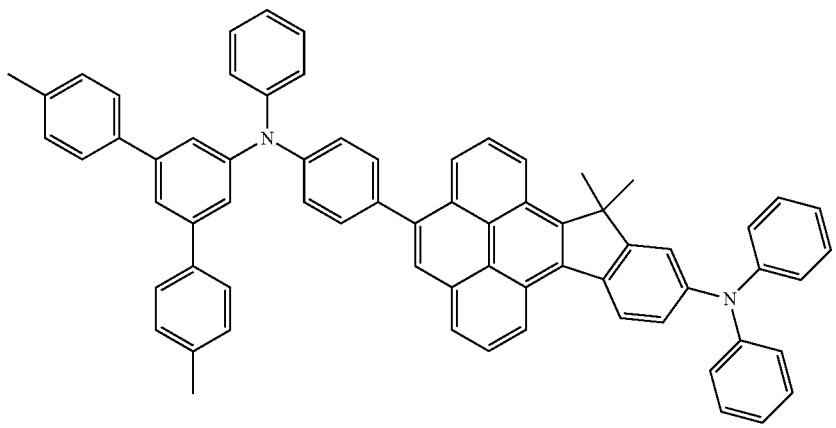
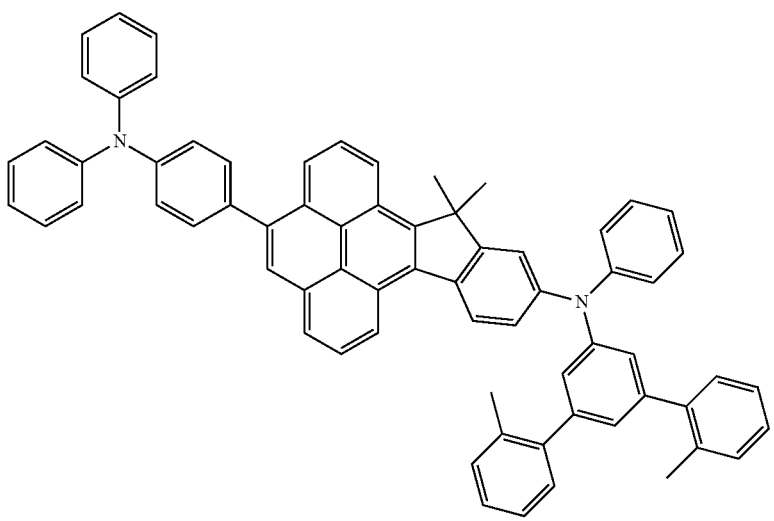

-continued
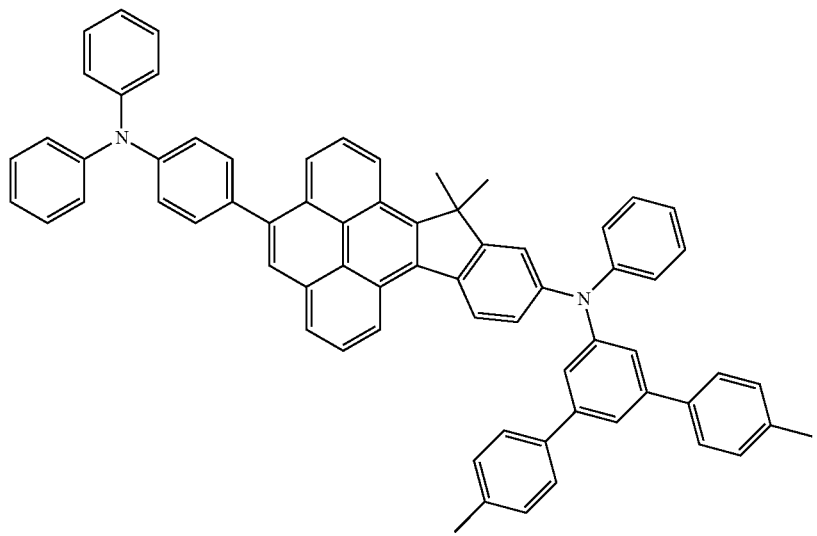
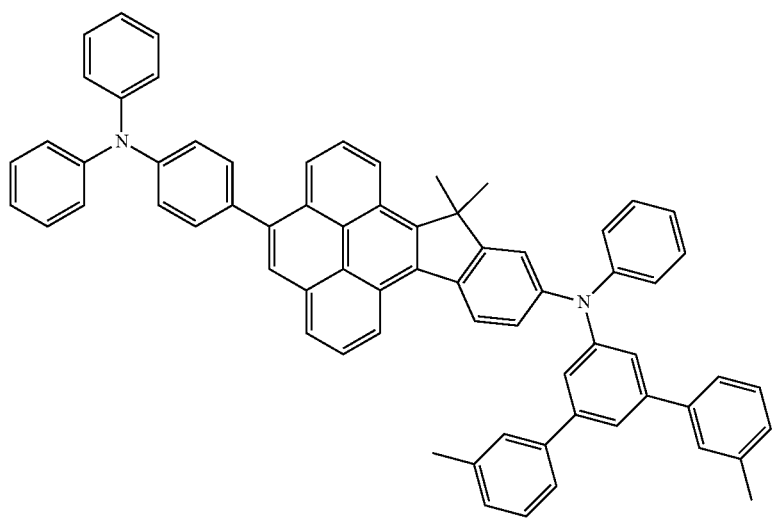
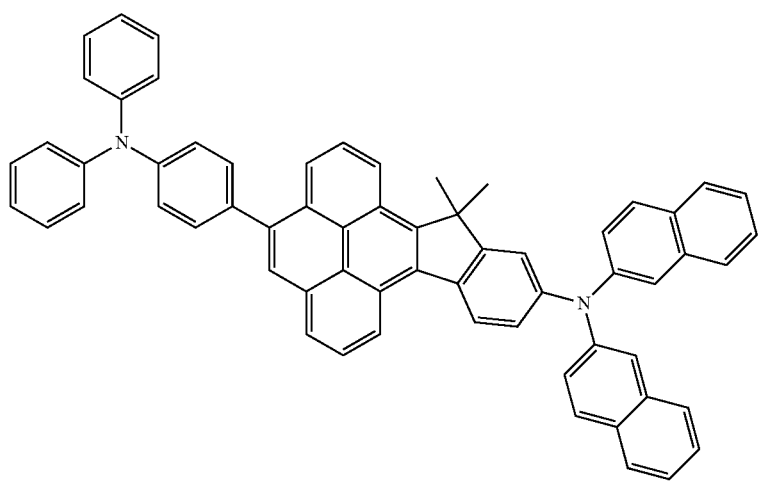

-continued
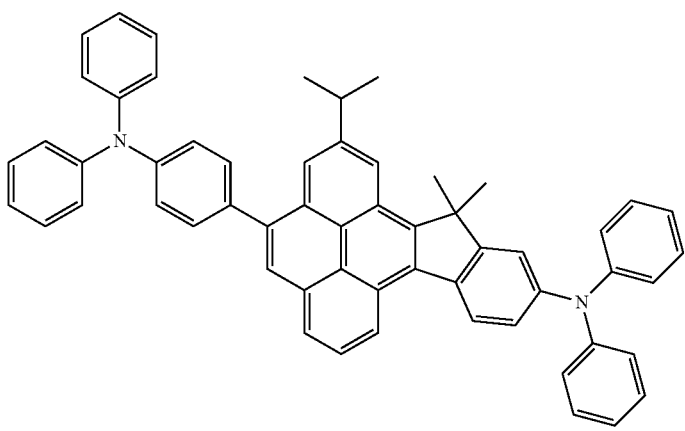
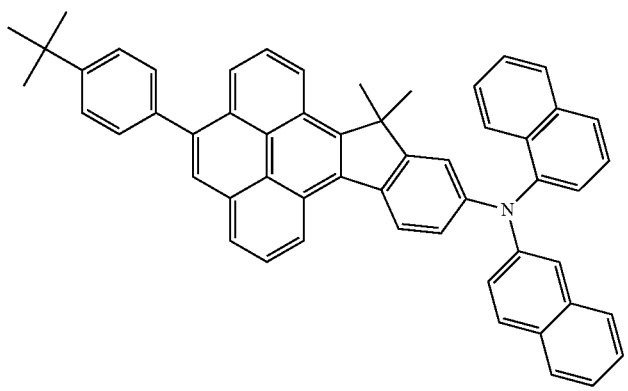
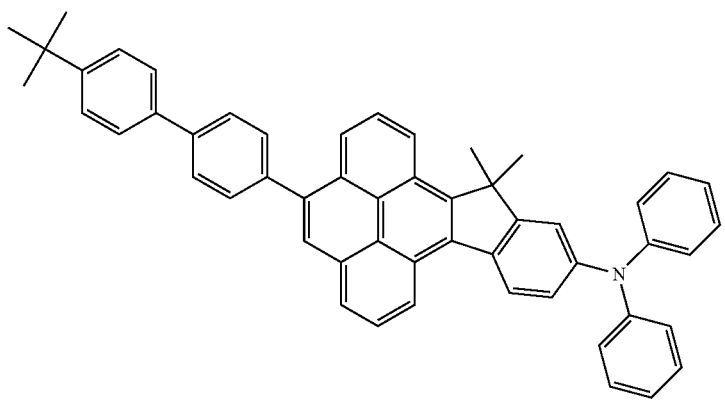
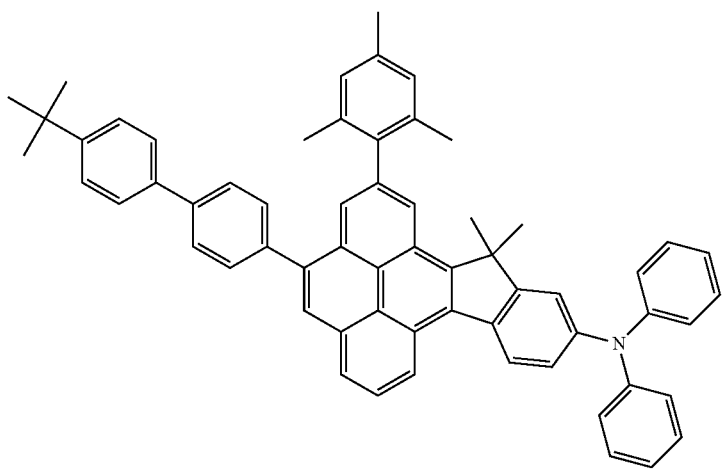

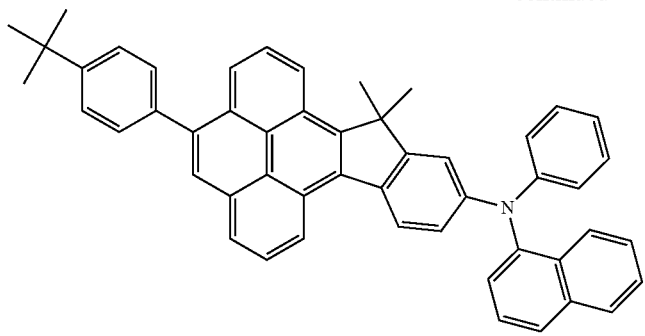
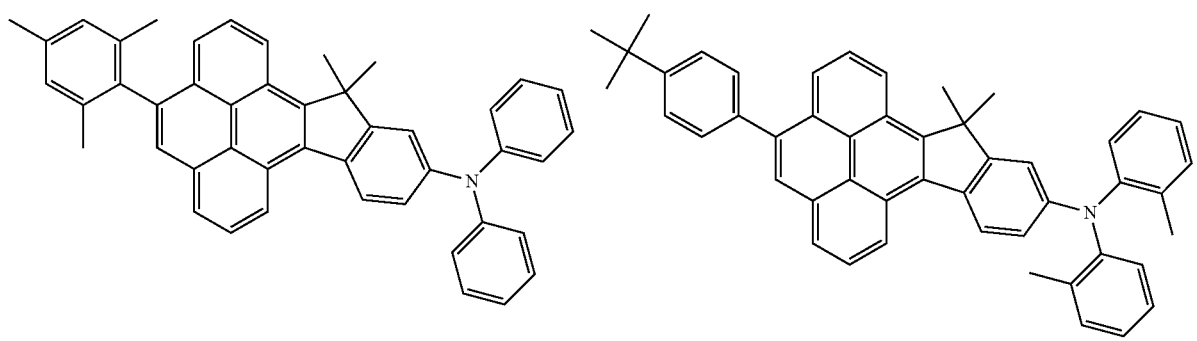
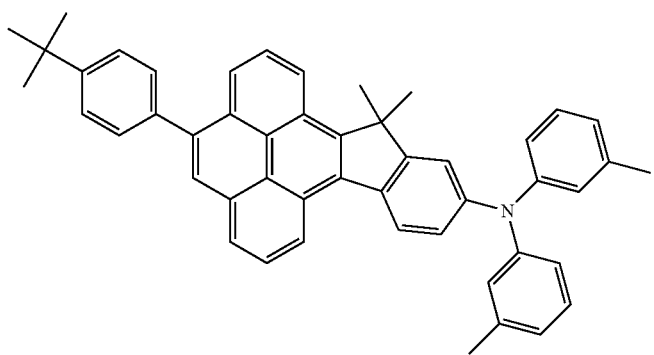
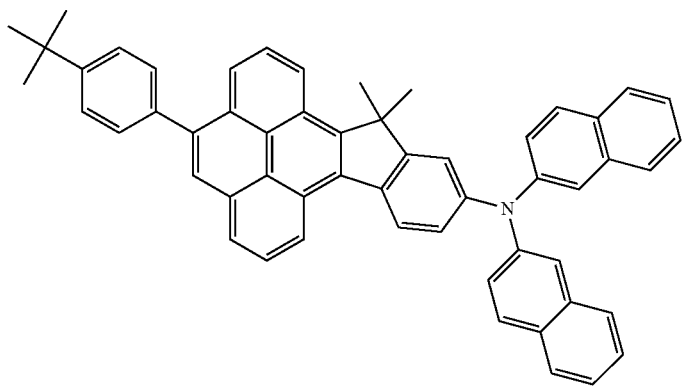

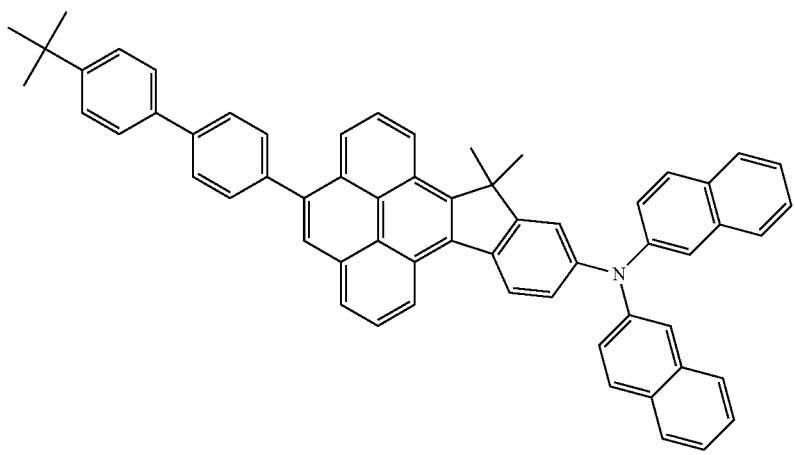
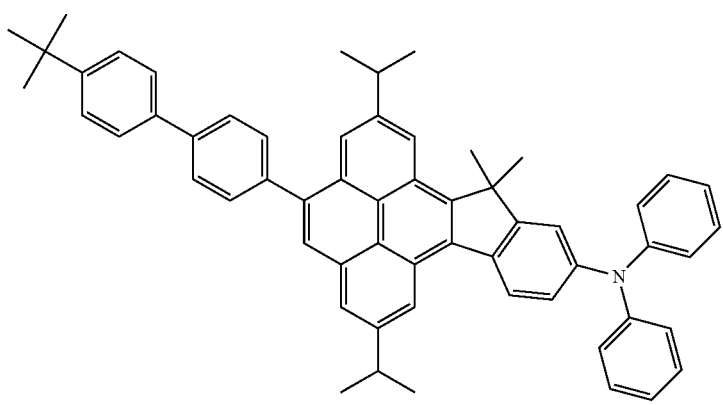
[Nineteenth Chemical Formula]
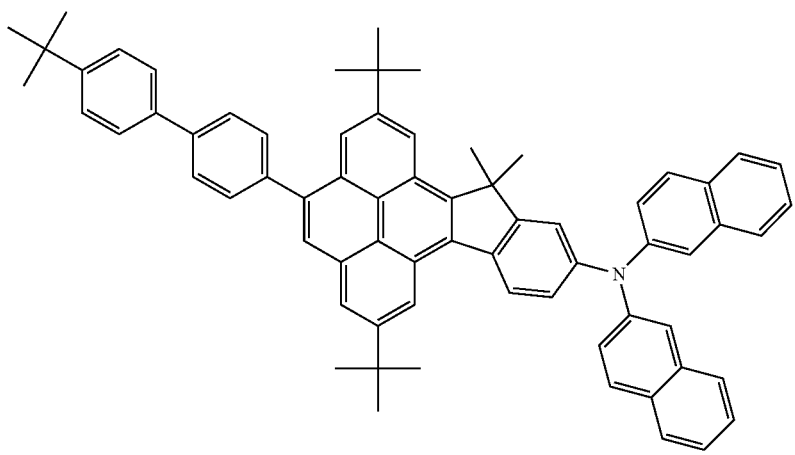

-continued
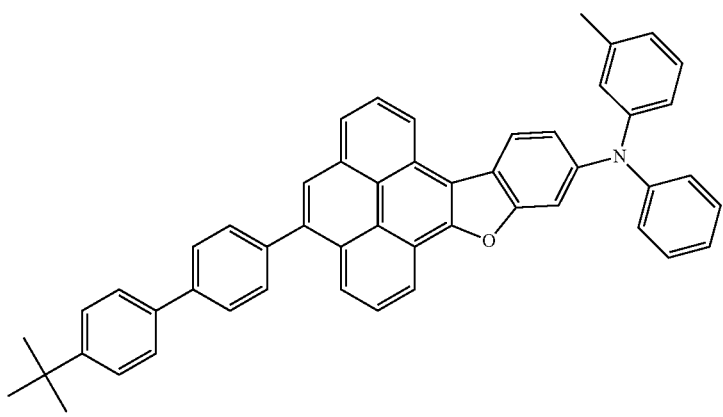
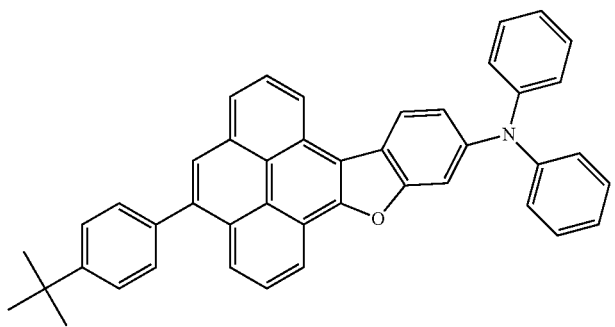
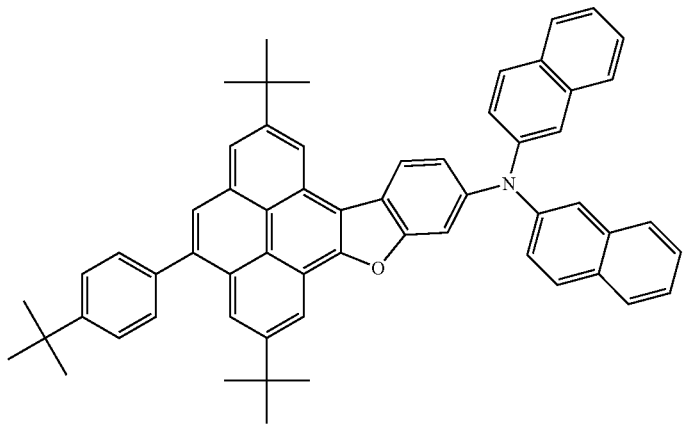
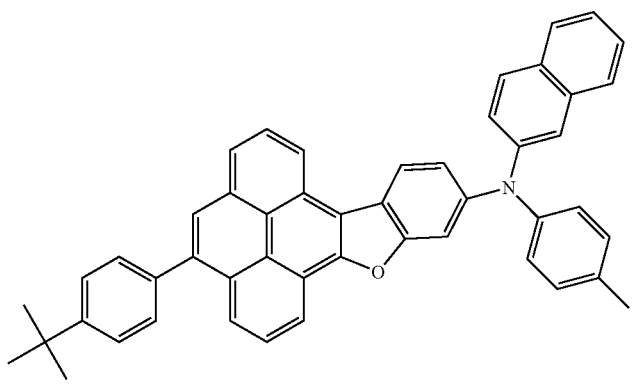

-continued
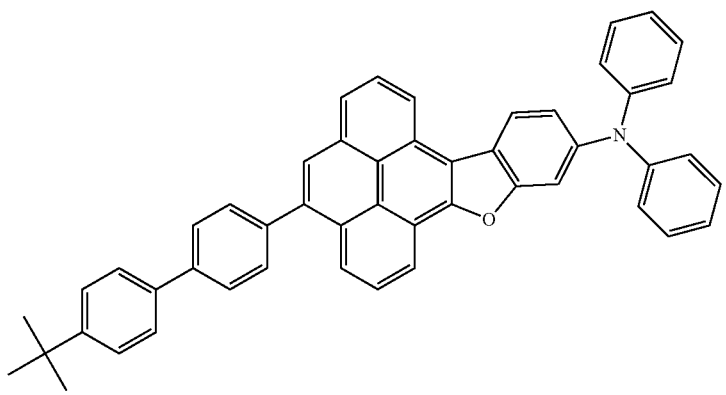
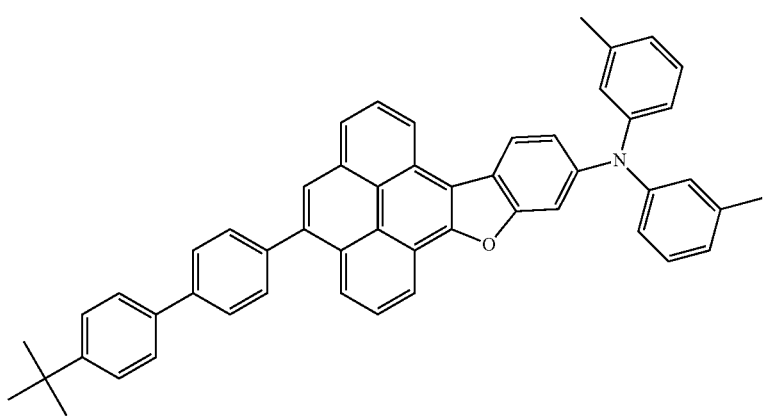
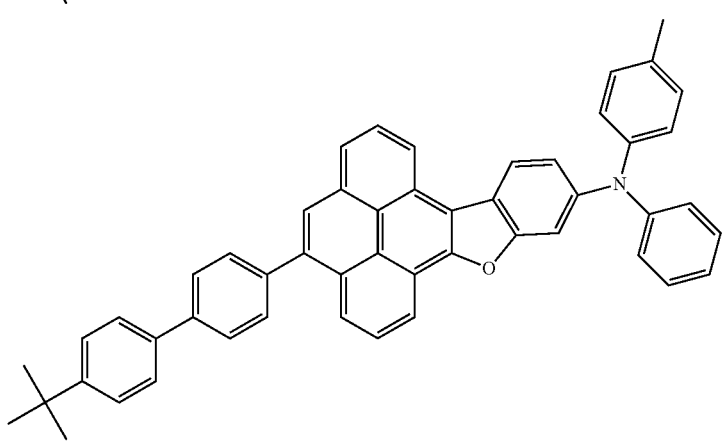
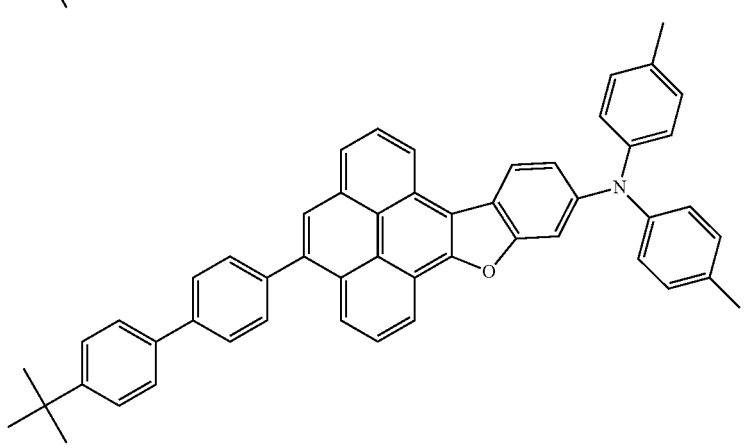

-continued
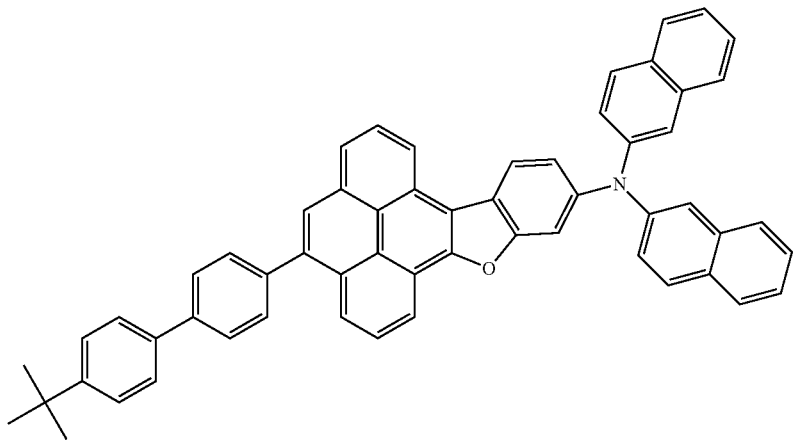
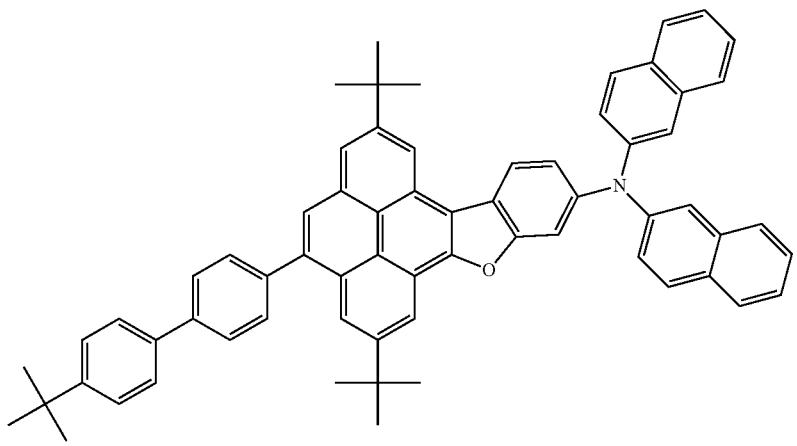
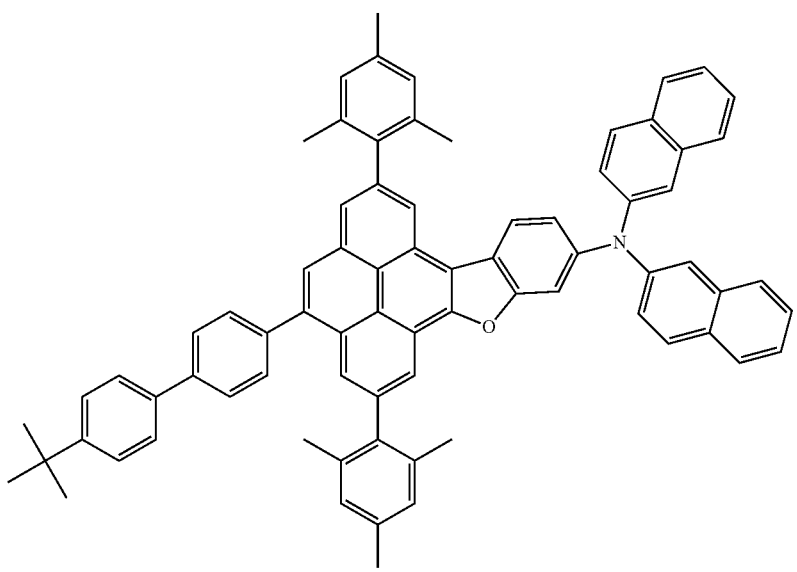

-continued
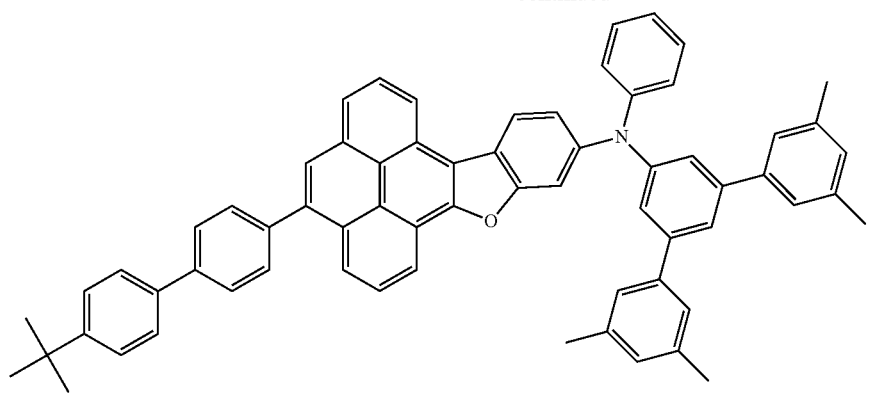
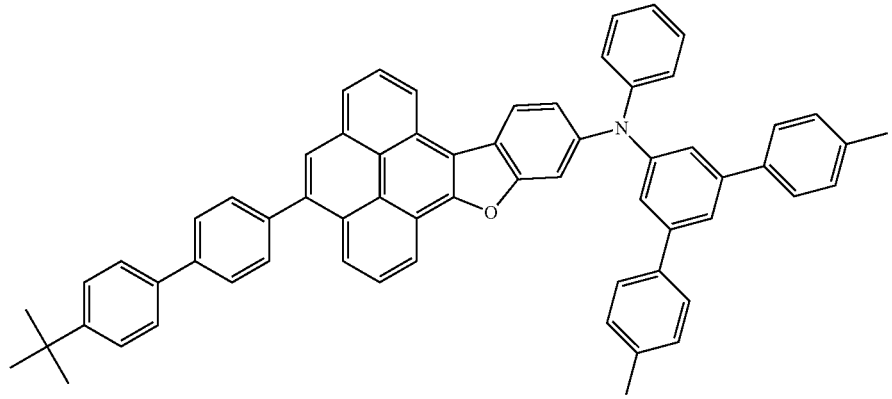
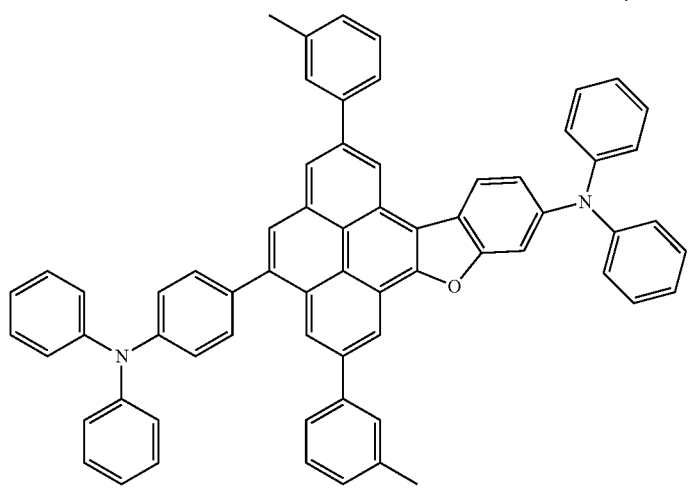
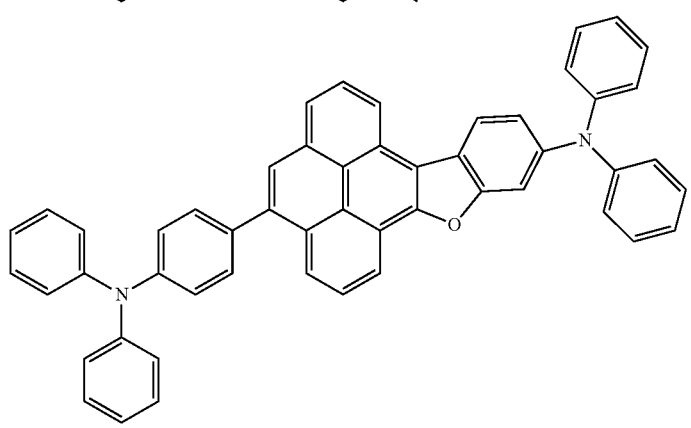

[Twentieth Chemical Formula]
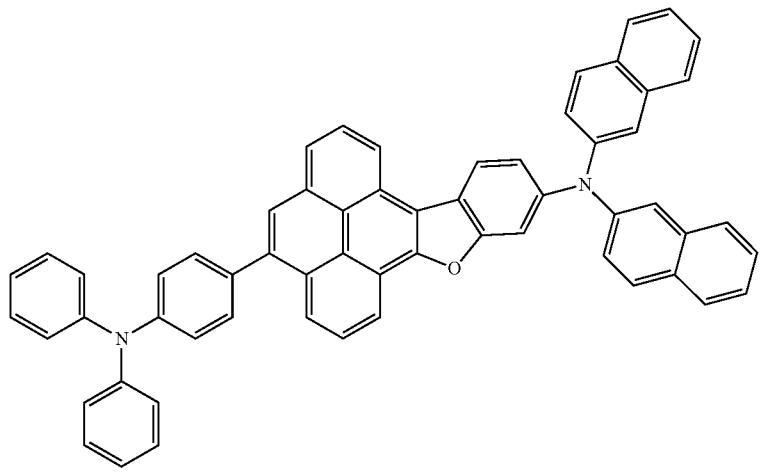
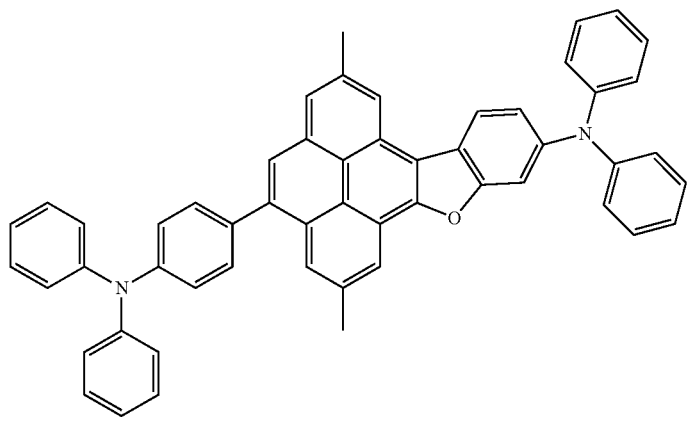
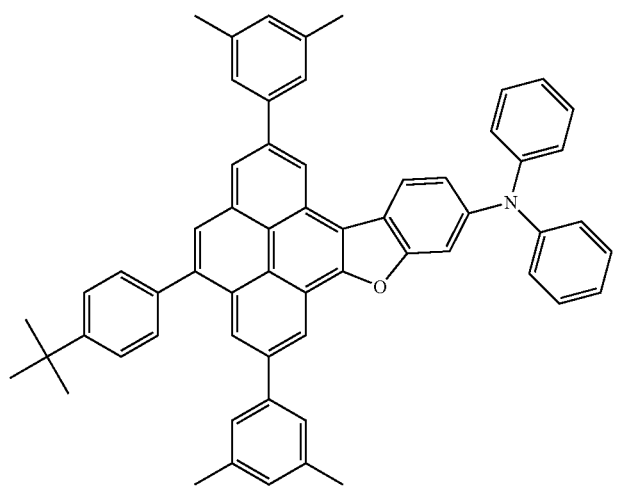

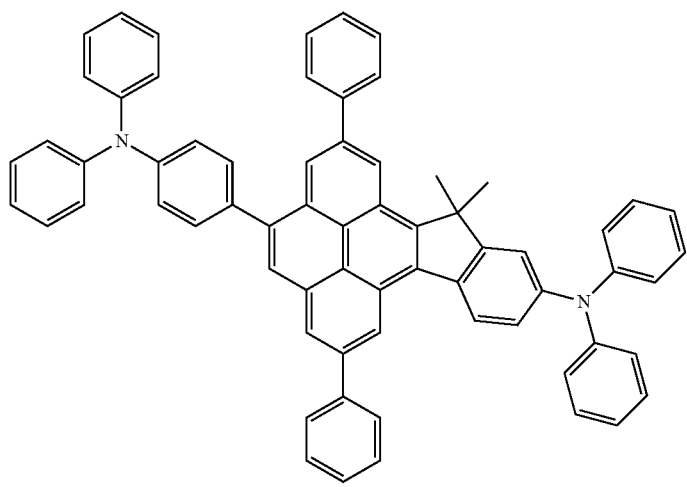
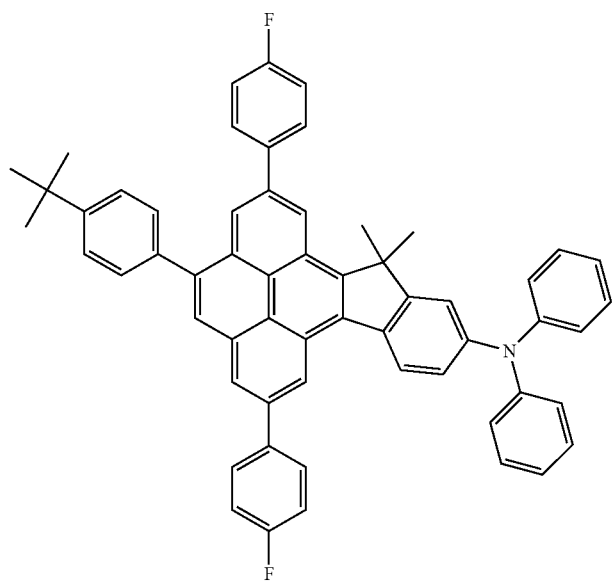
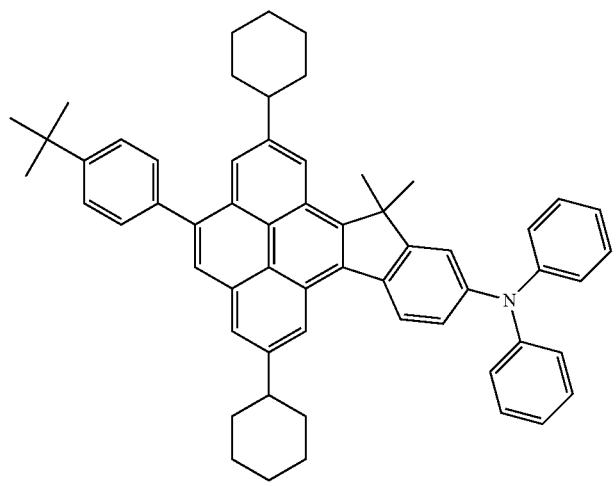

-continued
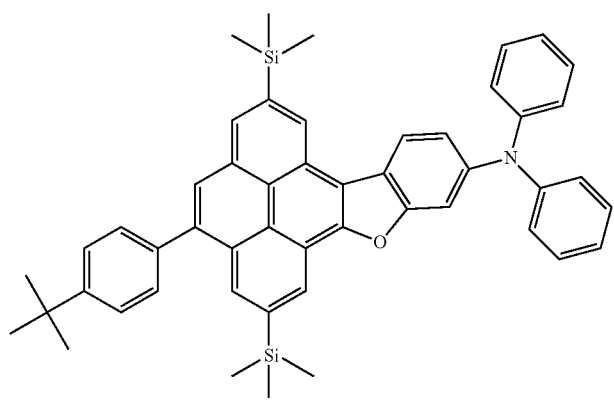
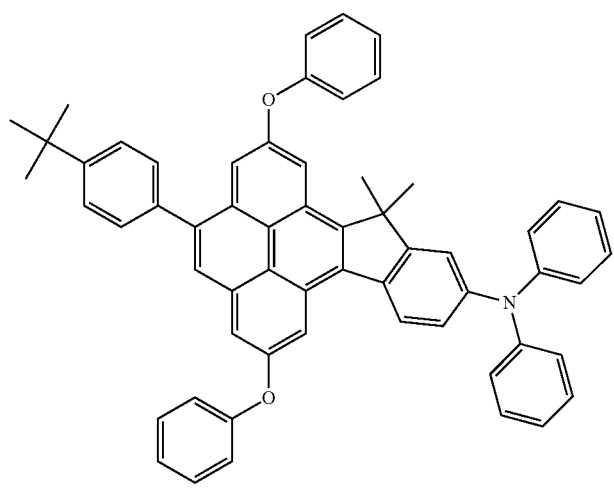
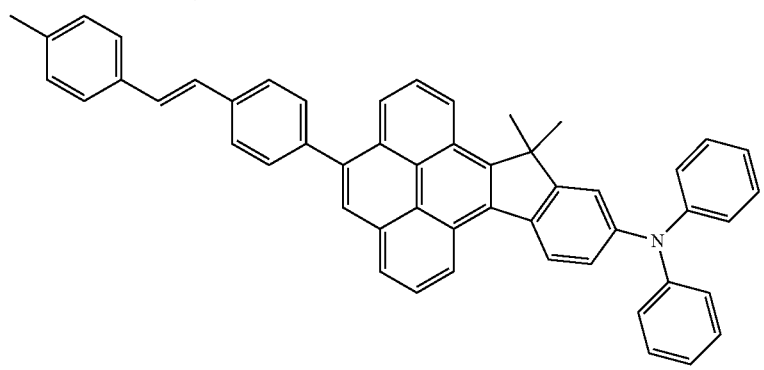
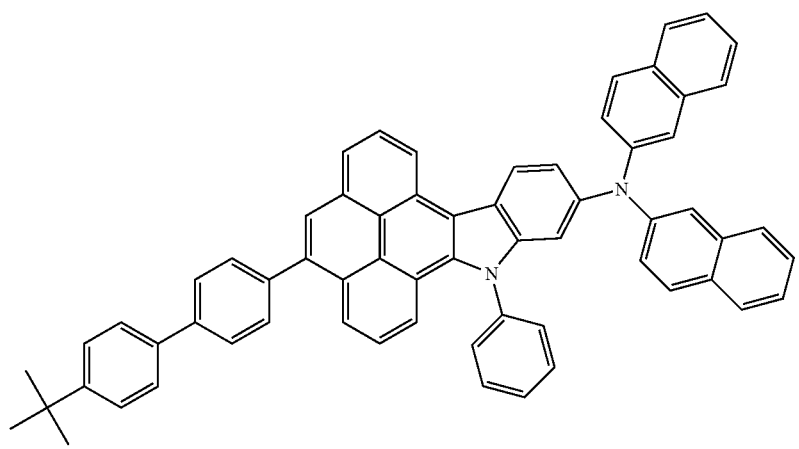

-continued
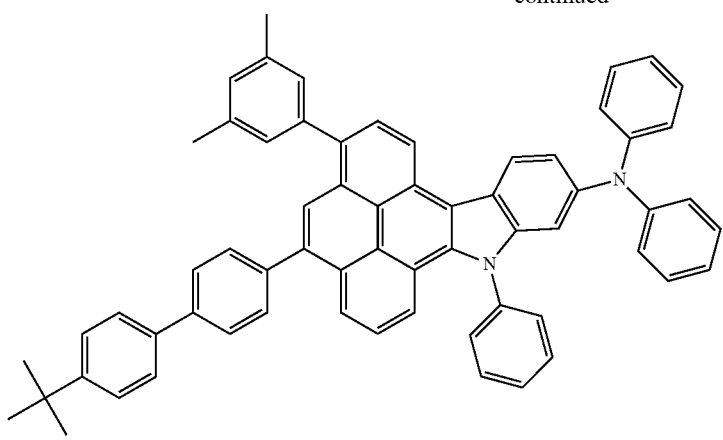
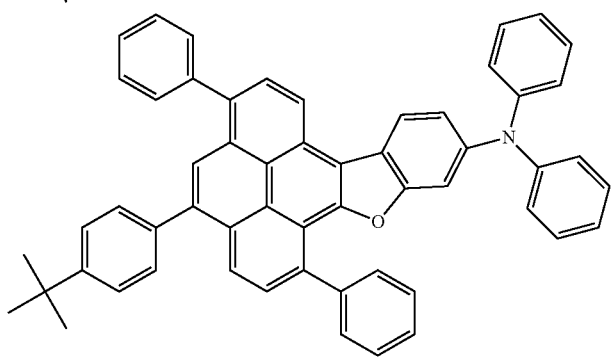
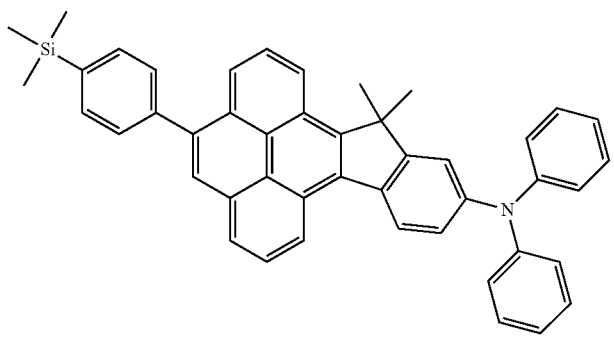
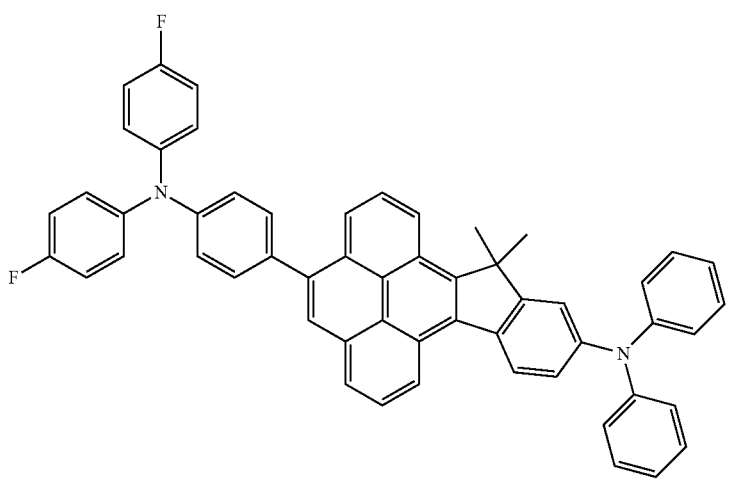

-continued
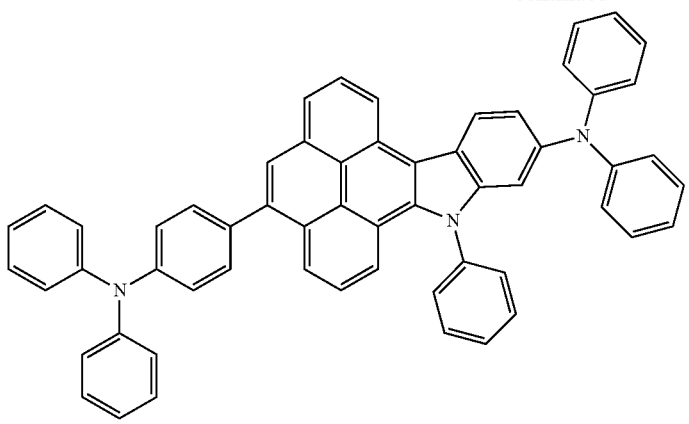
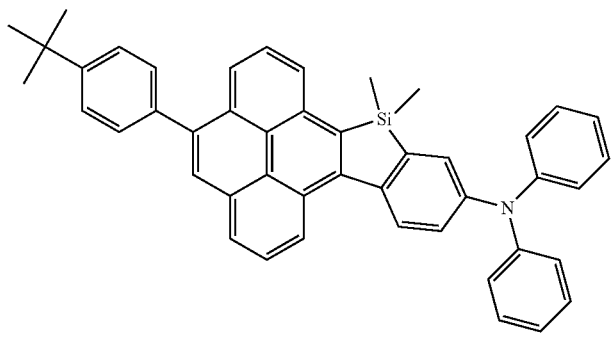
[Twenty-First Chemical Formula]
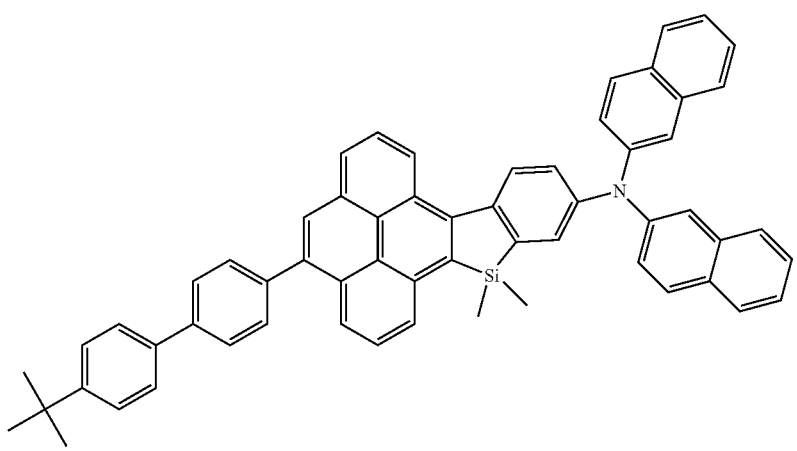
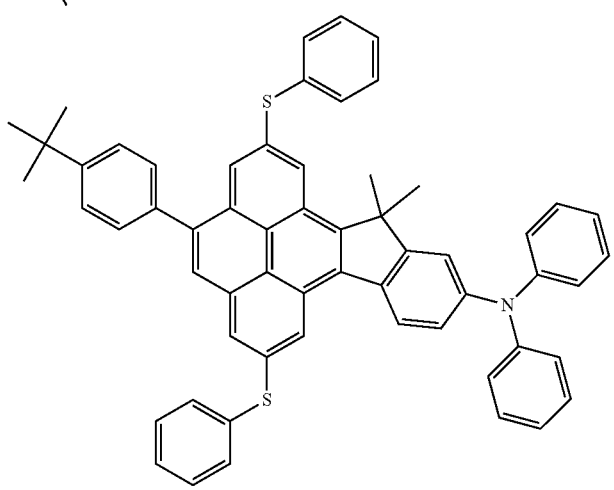

-continued
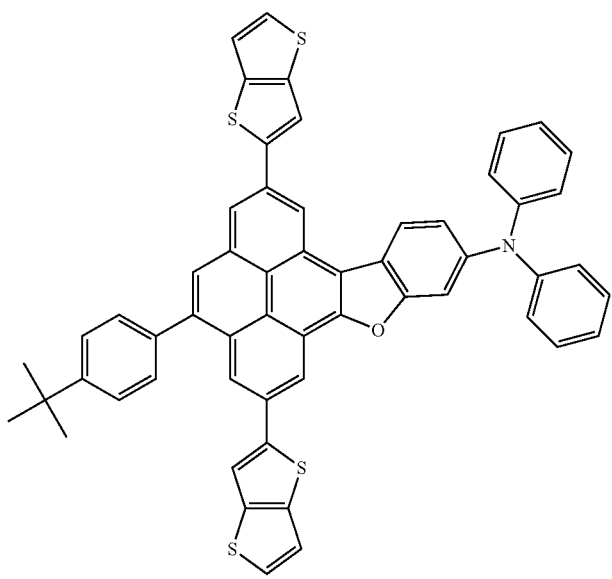
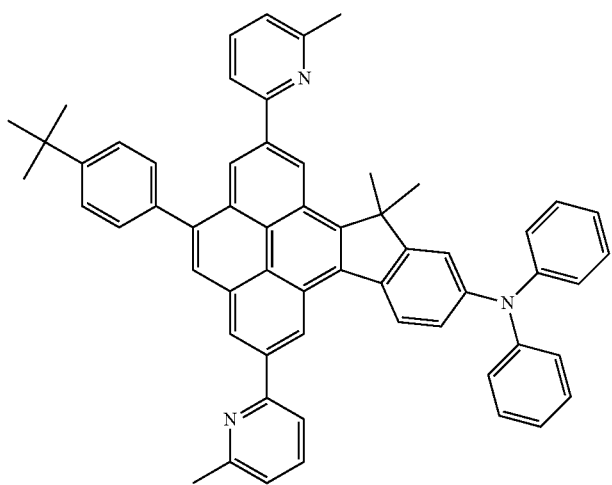
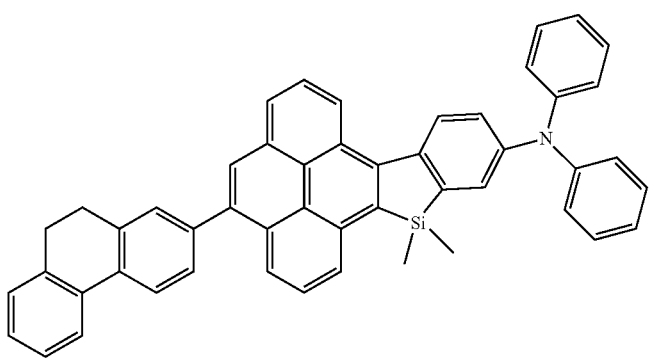

-continued
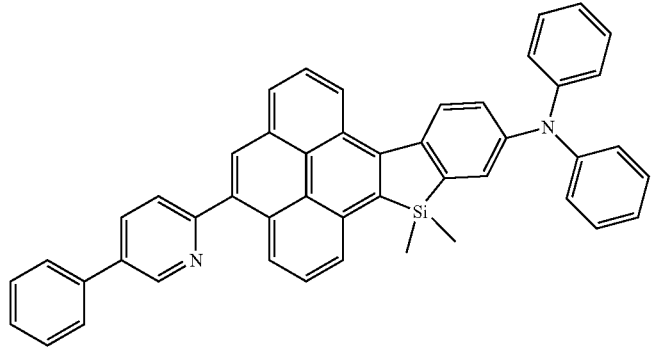
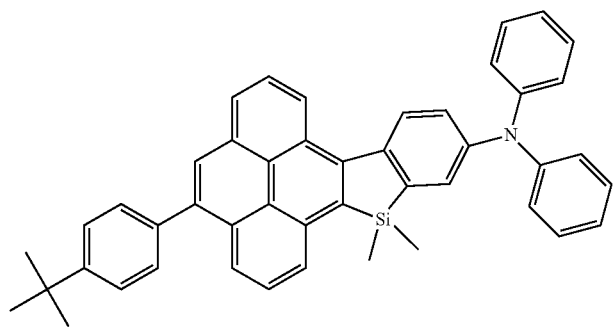
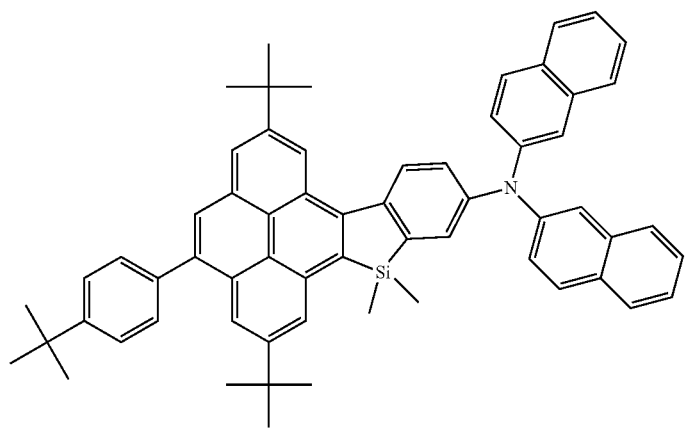
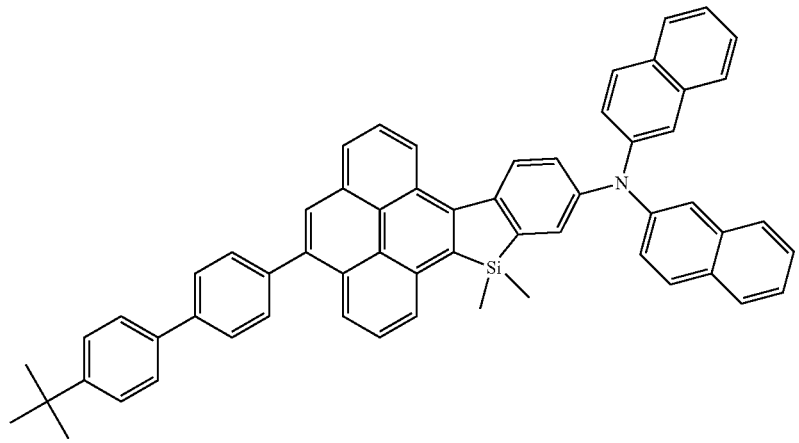

-continued
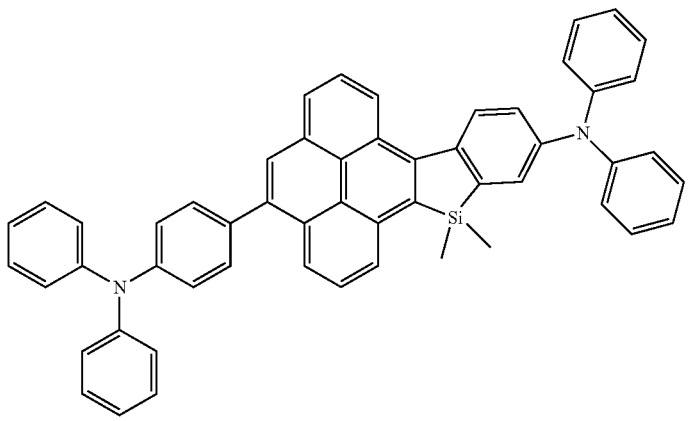
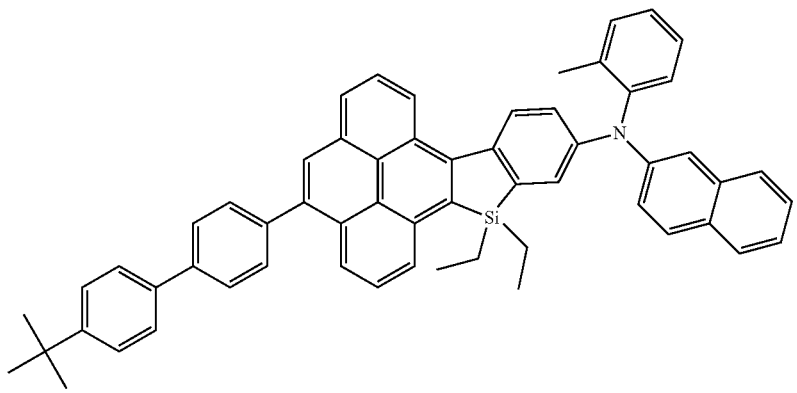
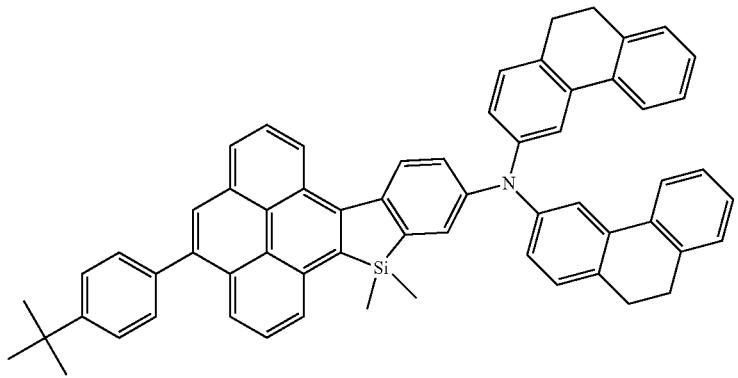
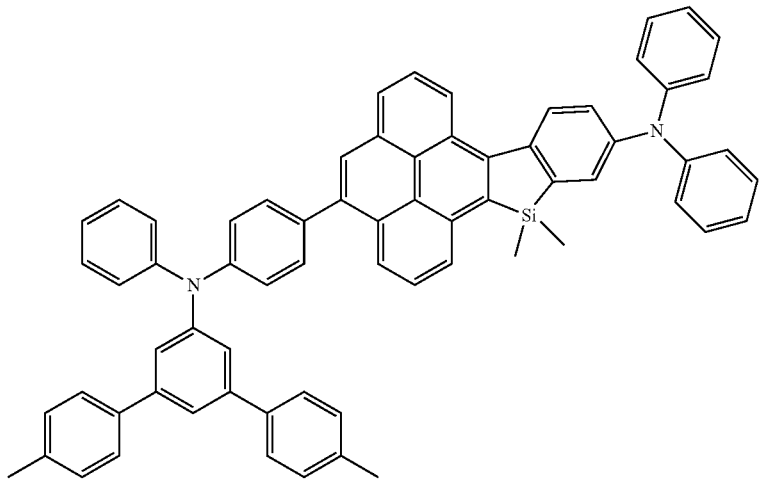

-continued
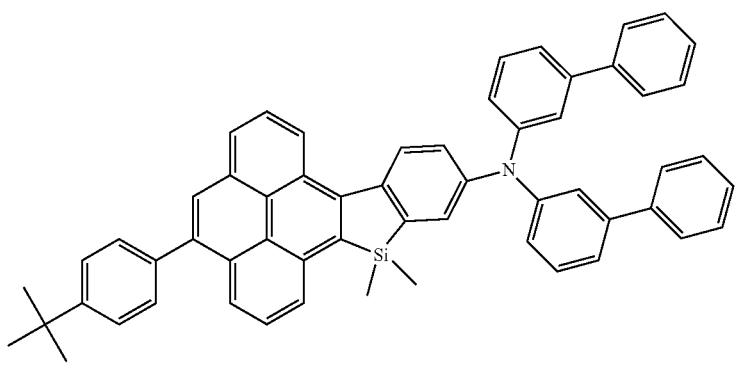
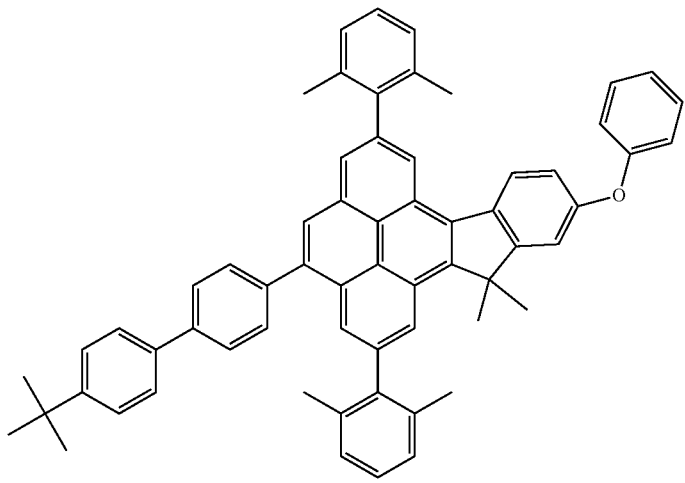
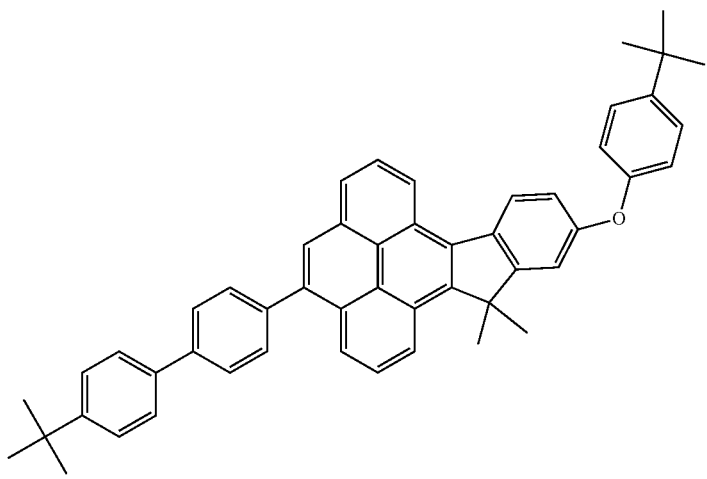

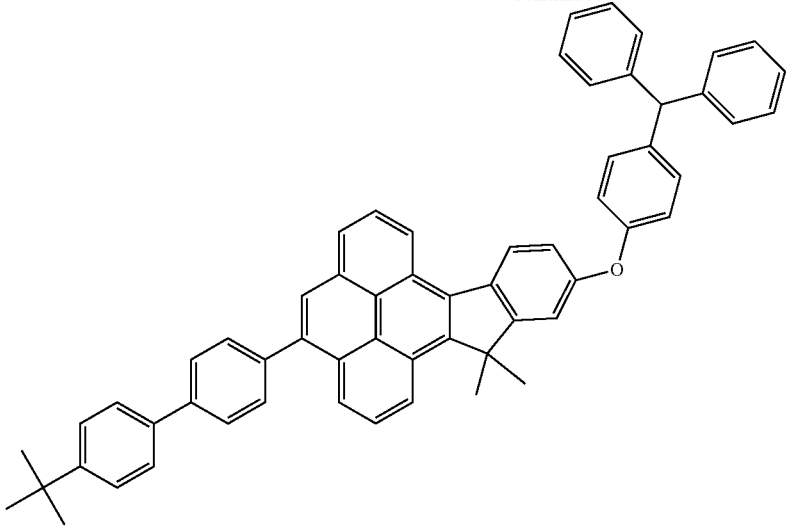

The light-emitting materials expressed by General Formula 1 above can be synthesized by combining publicly known reactions. Moreover, they can be synthesized by the following scheme, for example:

[Twenty-Second Chemical Formula]

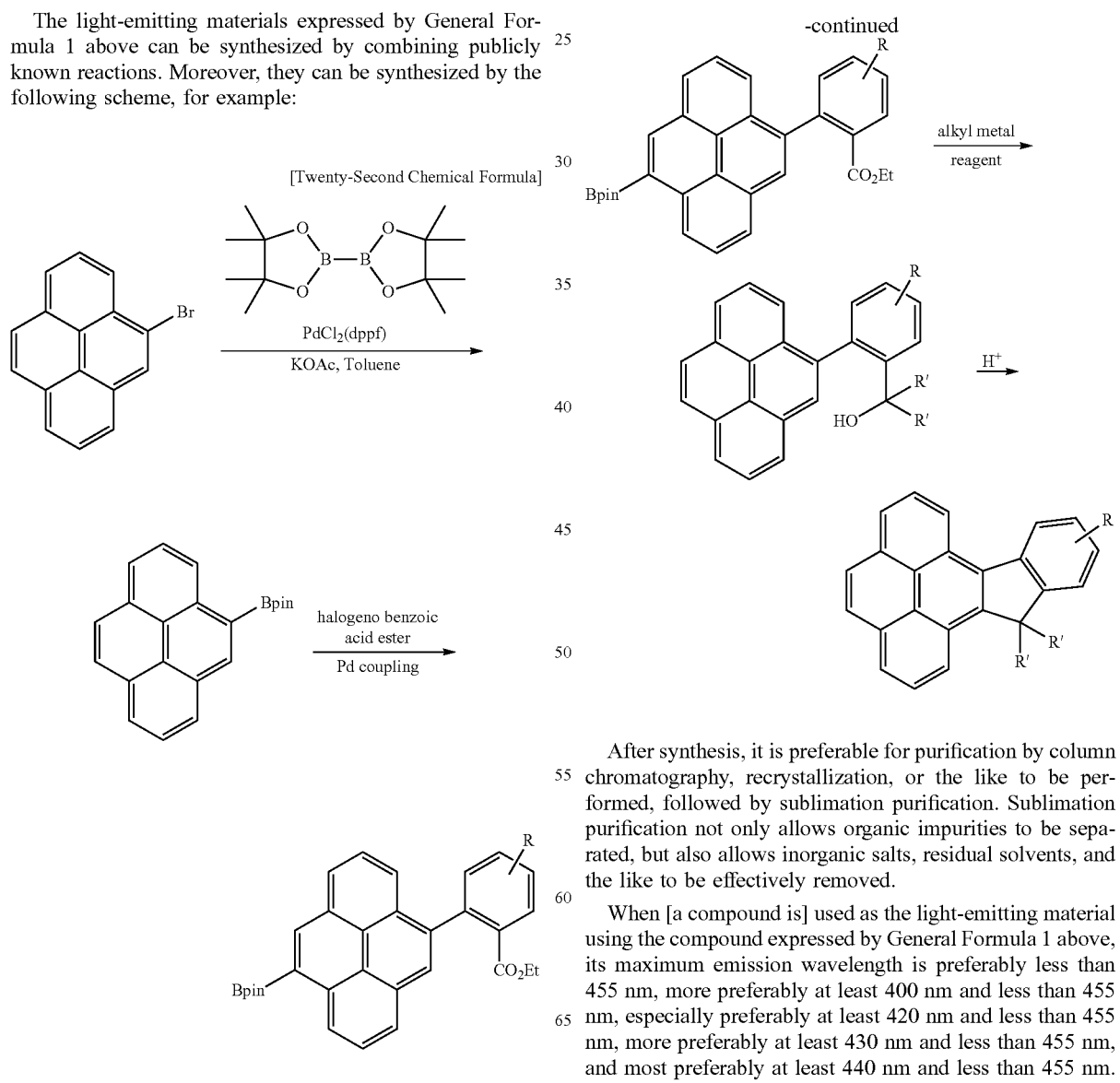

After synthesis, it is preferable for purification by column chromatography, recrystallization, or the like to be performed, followed by sublimation purification. Sublimation purification not only allows organic impurities to be separated, but also allows inorganic salts, residual solvents, and the like to be effectively removed.

When [a compound is] used as the light-emitting material using the compound expressed by General Formula 1 above, its maximum emission wavelength is preferably less than 455 nm, more preferably at least 400 nm and less than 455 nm, especially preferably at least 420 nm and less than 455 nm, more preferably at least 430 nm and less than 455 nm, and most preferably at least 440 nm and less than 455 nm.

Organic Electroluminescent Element

The organic electroluminescent element of the present invention has a substrate, a pair of electrodes disposed on this substrate and including an anode and a cathode, and a single or a plurality of organic layers disposed between these electrodes, and is characterized in that the aforementioned organic layer(s) include a light-emitting layer, with this light-emitting layer containing a host material and at least one light-emitting material expressed by General Formula 1 above.

There are no particular restrictions on the configuration of the organic electroluminescent element of the present invention. FIG. 1 shows one example of the configuration of the organic electroluminescent element of the present invention. The organic electroluminescent element 10 of FIG. 1 has, on a substrate 2, organic layers between a pair of electrodes (an anode 3 and a cathode 9).

The element configuration, substrate, cathode, and anode of the organic electroluminescent element are discussed in detail in Japanese Laid-Open Patent Application 2008-270736, for example, and what is described in this publication can be applied to the present invention.

Preferred modes of the organic electroluminescent element of the present invention will be described in detail below in the order of the substrate, electrodes, organic layers, protective layer, sealing container, drive method, emission wavelength, and applications.

<Substrate>

The organic electroluminescent element of the present invention has a substrate.

The substrate used in the present invention is preferably a substrate that will not scatter or attenuate light emitted from the organic layer(s). In the case of an organic material, one with excellent heat resistance, dimensional stability, solvent resistance, electrical insulation properties, and workability is preferable.

<Electrodes>

The organic electroluminescent element of the present invention has a pair of electrodes disposed on the aforementioned substrate and including an anode and a cathode.

For the quality of the light-emitting element, it is preferable for at least one of the electrodes constituting the pair of electrodes (the anode and/or cathode) to be transparent or semitransparent.

(Anode)

In general, there are no particular restrictions on the shape, structure, size, and so forth of the anode as long as it functions as an electrode that supplies holes to the organic layers, and one can be suitably selected from publicly known electrode materials depending on the purpose and application of the light-emitting element. As was described above, the anode is usually provided as a transparent anode.

(Cathode)

In general, there are no particular restrictions on the shape, structure, size, and so forth of the cathode as long as it functions as an electrode that injects electrons into the organic layers, and one can be suitably selected from publicly known electrode materials depending on the purpose and application of the light-emitting element.

<Organic Layer(s)>

The organic electroluminescent element of the present invention has a single or a plurality of organic layers disposed between the aforementioned electrodes and is characterized in that the aforementioned organic layer(s) include a light-emitting layer and that this light-emitting layer contains a host material and at least one light-emitting material expressed by General Formula 1 above.

There are no particular restrictions on the aforementioned organic layer(s), which can be suitably selected according to the purpose and application of the organic electroluminescent element, but [the organic layer(s)] are preferably formed over the aforementioned transparent electrode(s) or the aforementioned semi-transparent electrode(s). In this case, the organic layers are formed on the entire surface or one face of the aforementioned transparent electrode(s) or the aforementioned semitransparent electrode(s).

There are no particular restrictions on the shape, size, thickness, and so forth of the organic layers, which can be suitably selected according to the purpose.

The configuration of the organic layers, a method for forming the organic layers, preferred modes of various layers configuring the organic layers, and the materials used in the various layers in the organic electroluminescent element of the present invention will be described in order below.

(Configuration of Organic Layers)

In the organic electroluminescent element of the present invention, the aforementioned organic layer(s) include a light-emitting layer. The aforementioned organic layers preferably include a charge transport layer. The aforementioned term "charge transport layer" refers to a layer in which charge movement occurs when voltage is applied to the organic electroluminescent element. Concrete examples include a hole injection layer, a hole transport layer, an electron blocking layer, a light-emitting layer, a hole blocking layer, an electron transport layer, or an electron injection layer. If the aforementioned charge transport layer is a hole injection layer, a hole transport layer, an electron blocking layer, or a light-emitting layer, it is possible to manufacture a low-cost and high-efficiency organic electroluminescent element.

The compound expressed by General Formula 1 above is contained in at least one layer of the light-emitting layer(s) in a single or a plurality of organic layers disposed between the aforementioned electrodes of the organic electroluminescent element.

However, the compound expressed by General Formula 1-1 [sic][3] above may be contained in other organic layer(s) of the organic electroluminescent element of the present invention as long as it does not go against the spirit of the present invention. Examples of organic layers (other than the light-emitting layer) that may contain the compound expressed by General Formula 1 above include a hole injection layer, a hole transport layer, an electron transport layer, an electron injection layer, an exciton blocking layer, and a charge blocking layer (a hole blocking layer, an electron blocking layer, etc.), with an exciton blocking layer, a charge blocking layer, an electron transport layer, or an electron injection layer being preferable, and an exciton blocking layer, a charge blocking layer, or an electron transport layer being more preferable.

[3] Translator's note: apparent error in the original; "General Formula 1-1" should be "General Formula 1."

When the compound expressed by General Formula 1 above is contained in the light-emitting layer, the compound expressed by General Formula 1 is preferably contained in an amount of 0.1 to 100 wt %, more preferably 1 to 50 wt %, and even more preferably 2 to 20 wt %, with respect to the total weight of the light-emitting layer.

When the compound expressed by General Formula 1 above is contained in an organic layer other than the light-emitting layer, the compound expressed by General Formula 1 is preferably contained in an amount of 70 to 100 wt %, more preferably 80 to 100 wt %, and even more preferably 90 to 100 wt % with respect to the total weight of this organic layer.

(Organic Layer Formation Method)

Each of the organic layers of the organic electroluminescent element of the present invention can be favorably formed by vapor deposition, sputtering, or another such dry film formation method, or by transfer, printing, spin coating, bar coating, or another such wet film formation method (solution coating method) as well.

In the organic electroluminescent element of the present invention, the organic layers disposed between the aforementioned pair of electrodes preferably [include] at least one layer that is formed by vapor deposition of a composition containing the compound expressed by General Formula 1 above.

(Light-Emitting Layer)

When an electric field is applied, the light-emitting layer accepts holes from the anode, the hole injection layer, or the hole transport layer, accepts electrons from the cathode, the electron injection layer, or the electron transport layer, and has the function of emitting light by providing a site for the rebinding of holes and electrons. However, the aforementioned light-emitting layer in the present invention is not necessarily limited to emission of light by such a mechanism.

The aforementioned light-emitting layer in the organic electroluminescent element of the present invention may be constituted solely from the aforementioned light-emitting material or may also be made up of a mixed layer of a host material and the aforementioned light-emitting material. With regard to the types of the aforementioned light-emitting material, there may be just one type or two or more types. The aforementioned host material is preferably a charge transport material. With regard to [the types of] the aforementioned host material, there may be just one type or two or more types. Examples include a mixed configuration of an electron transporting host material and a hole transporting host material. Furthermore, a material which does not have a charge transporting property and does not emit light may also be included in the aforementioned light-emitting layer.

Moreover, the light-emitting layer may be a single layer or a multilayer of two or more layers, and the same light-emitting material or host material may be included in each layer, or different materials may be included in each layer. When there are a plurality of light-emitting layers, each light-emitting layer may also emit light of a different color.

There are no particular restrictions on the thickness of the light-emitting layer, but in general, it is preferably from 2 to 500 nm, and from the standpoint of external quantum efficiency, it is more preferably from 3 to 200 nm and even more preferably from 5 to 100 nm.

In the organic electroluminescent element of the present invention, the aforementioned light-emitting layer contains the compound expressed by General Formula 1 above, and the compound expressed by General Formula 1 above is used as the light-emitting material of the aforementioned light-emitting layer. Here, in this Specification, the host material refers to a compound that mainly handles the injection and transport of charges in the light-emitting layer, and also a compound that substantially does not emit light itself. [The phrase] "substantially does not emit light" here means that the amount of light emitted from this compound that substantially does not emit light is preferably no more than 5% of the total amount of light emitted by the entire element, more preferably no more than 3%, and even preferably no more than 1%. The compound expressed by General Formula 1 above may also be used as the host material of the light-emitting layer.

(Light-Emitting Material)

With the organic electroluminescent element of the present invention, a compound expressed by General Formula 1 above is used as the light-emitting material, but even in this case as well, a light-emitting material other than a compound expressed by General Formula 1 above can be used in combination. In the organic electroluminescent element of the present invention, furthermore, another light-emitting material different from the compound expressed by General Formula 1 above can be used in the light-emitting layer even when the compound expressed by General Formula 1 above is used as the host material of the light-emitting layer or when it is used in an organic layer other than the light-emitting layer.

The light-emitting material that can be used in the present invention may be a fluorescent material. Moreover, the light-emitting layer in the present invention can contain two or more types of light-emitting material in order to improve color purity or expand the emission wavelength band.

The fluorescent materials that can be used in the organic electroluminescent element of the present invention are discussed at length, for example, in paragraph numbers [0100] to of Japanese Laid-Open Patent Application 2008-270736 and paragraph numbers to [0090] of Japanese Laid-Open Patent Application 2007-266458, and what is discussed in these publications can be applied to the present invention.

There are no particular restrictions on the type of fluorescent material that can be used in the present invention, but besides the compounds expressed by General Formula 1-1 [sic][4] above, examples include benzoxazole, benzimidazole, benzothiazole, styryl benzene, polyphenyl, diphenyl butadiene, tetraphenyl butadiene, naphthalimide, coumarin, pyran, perinone, oxadiazole, aldazine, pyralizine, cyclopentadiene, bis-styryl anthracene, quinacridone, pyrrolopyridine, thiadiazolopyridine, cyclopentadiene, styrylamine, condensed polycyclic aromatic compounds (such as anthracene, phenanthroline, pyrene, perylene, rubrene, and pentacene), a variety of metal complexes typified by metal complexes of 8-quinolinol, pyrromethene complexes, and rare earth complexes, polymer compounds such as polythiophene, polyphenylene, and polyphenylene vinylene, organosilanes, and derivatives of these.

[4]Translator's note: apparent error in the original; "General Formula 1-1" should be "General Formula 1."

Besides these, it is also possible to use the compounds described in [0082] of Japanese Laid-Open Patent Application 2010-111620 as the light-emitting material.

The light-emitting layer in the organic electroluminescent element of the present invention may be configured from only a light-emitting material or may be made up of a mixed layer of a host material and a light-emitting material. The type of the light-emitting material may be just one type or two or more types. The host material is preferably a charge transport material. There may be just one type of host material, or two or more types may be used, and examples include a mixture of an electron transporting host material and a hole transporting host material. Furthermore, a material which does not have a charge transporting property and does not emit light may be included in the light-emitting layer.

Moreover, the light-emitting layer may be a single layer or a multilayer of two or more layers, and the same light-emitting material or host material may be contained in each layer, or a different material may be contained in each layer. When there are a plurality of light-emitting layers, each of the light-emitting layers may also emit light of a different color.

(Host Material)

The host material is a compound that mainly handles the injection and transport of charges in the light-emitting layer, and is also a compound that substantially does not emit light itself. [The phrase] "substantially does not emit light" here means that the amount of light emitted from this compound that substantially does not emit light is preferably no more than 5% of the total amount of light emitted by the entire element, more preferably no more than 3%, and even more preferably no more than 1%.

The following compounds are examples of host materials that can be used in the organic electroluminescent element of the present invention:

These examples include pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin-based compounds, condensed ring aromatic hydrocarbon compounds (such as fluorene, naphthalene, phenanthrene, and triphenylene), polysilane-based compounds, poly(N-vinylcarbazole), aniline-based copolymers, conductive macromolecular oligomers such as thiophene oligomers and polythiophene, organosilanes, carbon films, pyridine, pyrimidine, triazine, imidazole, pyrazole, triazole, oxazole, oxadiazole [sic][5], fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic acid anhydrides such as naphthalene [and] perylene, phthalocyanine, and a variety of metal complexes typified by metal complexes of an 8-quinolinol derivative, metal phthalocyanine, and metal complexes having benzoxazole or benzothiazole as a ligand, and derivatives of these (which may have a substituent or a condensed ring). Besides these, the compounds described in [0081] and [0083] of Japanese Laid-Open Patent Application 2010-111620 can also be used.

[5]Translator's note: "imidazole," "pyrazole," "triazole," "oxazole," and "oxadiazole" repeatedly appear in this list in the original.

Of these, carbazole, dibenzothiophene, dibenzofuran, arylamine, condensed ring aromatic hydrocarbon compounds, and metal complexes are preferable, with condensed ring aromatic hydrocarbon compounds being especially preferable because of their stability. Of the condensed ring aromatic hydrocarbon compounds, naphthalene-based compounds, anthracene-based compounds, phenanthrene-based compounds, triphenylene-based compounds, and pyrene-based compounds are preferable, with anthracene-based compounds and pyrene-based compounds being more preferable, and anthracene-based compounds being especially preferable. The compounds described in [0033] to [0064] of WO 2010/134350 are especially favorable as the anthracene-based compounds, and examples include compounds H-1 and H-2 (mentioned later).

With the organic electroluminescent element of the present invention, the aforementioned host material contained in the aforementioned light-emitting layer preferably has a $C_{10}$ to $C_{50}$ hydrocarbon condensed ring structure.

The aforementioned $C_{10}$ to $C_{50}$ hydrocarbon condensed ring structure preferably has [a skeleton of] naphthalene, phenanthrene, benzo[c]phenanthrene, anthracene, pyrene, triphenylene, or chrysene, more preferably naphthalene, phenanthrene, benzo[c]phenanthrene, or anthracene, and most preferably anthracene. That is, the aforementioned $C_{10}$ to $C_{50}$ hydrocarbon condensed ring structure of the aforementioned host material more preferably has an anthracene skeleton. In addition, it is especially preferable for the aforementioned $C_{10}$ to $C_{50}$ hydrocarbon condensed ring structure to be a compound made up solely of carbon and hydrogen or deuterium.

The host material that can be used in the light-emitting layer of the organic electroluminescent element of the present invention may be either a hole transporting host material or an electron transporting host material.

In the light-emitting layer, from the standpoints of color purity, luminous efficiency, and drive durability, it is preferable for the lowest excited singlet energy ($S_1$ energy) of the aforementioned host material in a film state to be higher than the $S_1$ energy of the aforementioned light-emitting material. The $S_1$ of the host material is preferably higher than the $S_1$ of the light-emitting material by at least 0.1 eV, more preferably higher by at least 0.2 eV, and even more preferably higher by at least 0.3 eV.

If the $S_1$ of the host material in a film state is lower than the $S_1$ of the light-emitting material, emission of light is quenched, so the host material needs to have a higher $S_1$ than the light-emitting material. Furthermore, even when the $S_1$ of the host material is higher than that of the light-emitting material, if the difference in the $S_1$ [values] between the two is small, reverse energy movement from the light-emitting material to the host material will occur in places, and this can lead to lower efficiency, lower color purity, or a decrease in durability. Accordingly, the host material needs to have a sufficiently high $S_1$ as well as good chemical stability and carrier injection and transport properties.

Moreover, there are no particular restrictions on the amount in which the host compound is contained in the light-emitting layer of the organic electroluminescent element of the present invention, but from the standpoints of luminous efficiency and drive voltage, it is preferably from 15 to 95 wt % with respect to the weight of all the compounds forming the light-emitting layer. If the light-emitting layer includes a plurality of types of host compound including a compound expressed by General Formula 1, then the compound expressed by General Formula 1 is preferably contained in the total host compound in an amount of at least 50 wt % and no more than 99 wt %.

(Other Layers)

The organic electroluminescent element of the present invention may have other layers besides the aforementioned light-emitting layer.

Examples of other organic layers other than the aforementioned light-emitting layer that may be included in the aforementioned organic layers include a hole injection layer, a hole transport layer, a blocking layer (hole blocking layer, exciton blocking layer, etc.), and an electron transport layer. The following are concrete examples of the layer configuration, but the present invention is in no way limited to these configurations:

anode/hole transport layer/light-emitting layer/electron transport layer/cathode anode/hole transport layer/light-emitting layer/blocking layer/electron transport layer/cathode anode/hole transport layer/light-emitting layer/blocking layer/electron transport layer/electron injection layer/cathode anode/hole injection layer/hole transport layer/light-emitting layer/blocking layer/electron transport layer/cathode anode/hole injection layer/hole transport layer/light-emitting layer/electron transport layer/electron injection layer/cathode anode/hole injection layer/hole transport layer/light-emitting layer/blocking layer/electron transport layer/electron injection layer/cathode anode/hole injection layer/hole transport layer/blocking layer/light-emitting layer/blocking layer/electron transport layer/electron injection layer/cathode The organic electroluminescent element of the present invention preferably includes at least one organic layer preferably disposed between the aforementioned anode and the aforementioned light-emitting layer (A). From the anode side, a hole injection layer, a hole transport layer, and an electron blocking layer can be cited as examples of organic layers preferably disposed between the aforementioned anode and the aforementioned light-emitting layer of (A) above.

The organic electroluminescent element of the present invention preferably includes at least one organic layer preferably disposed between the aforementioned cathode and the aforementioned light-emitting layer (B). From the cathode side, an electron injection layer, an electron transport layer, and a hole blocking layer can be cited as examples of organic layers preferably disposed between the aforementioned cathode and the aforementioned light-emitting layer of (B) above.

In concrete terms, one example of a preferred mode of the organic electroluminescent element of the present invention is the mode described in FIG. 1, being a mode in which a hole injection layer 4, a hole transport layer 5, a light-emitting layer 6, a hole blocking layer 7, and an electron transport layer 8 are laminated in this order from the side of the anode 3 as the aforementioned organic layers.

These layers other than the aforementioned light-emitting layer that may be included in the organic electroluminescent element of the present invention will be described below.

(A) Organic Layers Preferably Disposed Between the Anode and the Aforementioned Light-Emitting Layer First, (A) organic layers preferably disposed between the aforementioned anode and the aforementioned light-emitting layer will be described.

(A-1) Hole Injection Layer and Hole Transport Layer

The hole injection layer and the hole transport layer are layers having the function of accepting holes from the anode or the anode side and transporting them to the cathode side.

The light-emitting element of the present invention preferably includes at least one organic layer between the light-emitting layer and the anode, and this organic layer preferably contains at least one type of compound out of the compounds expressed by General Formula Sa-1, General Formula Sb-1, and General Formula Sc-1 below:

[Twenty-Third Chemical Formula]

General Formula Sa-1

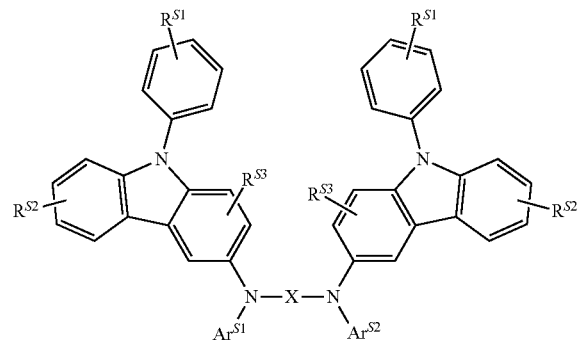

(In the formula, X represents a substituted or unsubstituted $C_1$ to $C_{30}$ alkylene group, a substituted or unsubstituted $C_2$ to $C_{30}$ alkenylene group, a substituted or unsubstituted $C_6$ to $C_{30}$ arylene group, a substituted or unsubstituted $C_2$ to $C_{30}$ heteroarylene group, or a substituted or unsubstituted $C_2$ to $C_{30}$ heterocycle. $R^{S1}$, $R^{S2}$, and $R^{S3}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent ones of the $R^{S1}$, $R^{S2}$, and $R^{S3}$ [groups] may bond to each other to form a saturated or unsaturated carbon ring. $Ar^{S1}$ and $Ar^{S2}$ represent each independently a substituted or unsubstituted $C_6$ to $C_{30}$ aryl group or a substituted or unsubstituted $C_2$ to $C_{30}$ heteroaryl group.)

[Twenty-Fourth Chemical Formula]

General Formula Sb-1

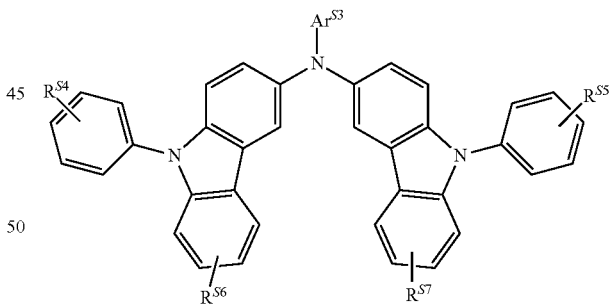

(In the formula, $R^{S4}$, $R^{S5}$, $R^{S6}$, and $R^{S7}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent ones of the $R^{S4}$, $R^{S5}$, $R^{S6}$, and $R^{S7}$ [groups] may bond to each other to form a saturated or unsaturated carbon ring. $Ar^{S3}$ represents a substituted or unsubstituted $C_6$ to $C_{30}$ aryl group or a substituted or unsubstituted $C_2$ to $C_{30}$ heteroaryl group.)

[Twenty-Fifth Chemical Formula]

General Formula Sc-1

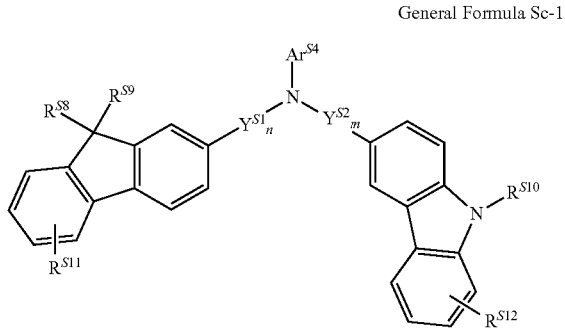

(In the formula, $R^{S8}$ and $R^{S9}$ represent each independently a hydrogen atom, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S10}$ represents a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S11}$ and $R^{S12}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S11}$ and $R^{S12}$ [groups] may bond to each other to form a saturated or unsaturated carbon ring. $Ar^{S4}$ represents a substituted or unsubstituted $C_6$ to $C_{30}$ aryl group or a substituted or unsubstituted $C_2$ to $C_{30}$ heteroaryl group. $Y^{S1}$ and $Y^{S2}$ represent each independently a substituted or unsubstituted $C_1$ to $C_{30}$ alkylene group or a substituted or unsubstituted $C_6$ to $C_{30}$ arylene group. n and m represent each independently an integer from 0 to 5.)

General Formula Sa-1 above will now be described.

In General Formula Sa-1 above, X represents a substituted or unsubstituted $C_1$ to $C_{30}$ alkylene group, a substituted or unsubstituted $C_2$ to $C_{30}$ alkenylene group, a substituted or unsubstituted $C_6$ to $C_{30}$ arylene group, a substituted or unsubstituted $C_2$ to $C_{30}$ heteroarylene group, or a substituted or unsubstituted $C_2$ to $C_{30}$ heterocycle. X is preferably a substituted or unsubstituted $C_6$ to $C_{30}$ arylene group, more preferably a substituted or unsubstituted phenylene, a substituted or unsubstituted biphenylene, and a substituted or unsubstituted naphthylene, and even more preferably a substituted or unsubstituted biphenylene.

$R^{S1}$, $R^{S2}$, and $R^{S3}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent ones of the $R^{S1}$, $R^{S2}$, and $R^{S3}$ [groups] may bond to each other to form a saturated or unsaturated carbon ring. Examples of the aforementioned saturated or unsaturated carbon ring include naphthalene, azulene, anthracene, fluorene, and phenalene. $R^{S1}$, $R^{S2}$, and $R^{S3}$ are preferably a hydrogen atom, a substituted or unsubstituted $C_1$ to $C_{30}$ alkyl group, a substituted or unsubstituted $C_6$ to $C_{30}$ aryl group, a substituted or unsubstituted $C_5$ to $C_{30}$ condensed polycyclic group, or a cyano group, with a hydrogen atom being more preferable.

$Ar^{S1}$ and $Ar^{S2}$ represent each independently a substituted or unsubstituted $C_6$ to $C_{30}$ aryl group or a substituted or unsubstituted $C_2$ to $C_{30}$ heteroaryl group. $Ar^{S1}$ and $Ar^{S2}$ are preferably a substituted or unsubstituted phenyl group.

Next, General Formula Sb-1 above will be described.

In General Formula Sb-1 above, $R^{S4}$, $R^{S5}$, $R^{S6}$, and $R^{S7}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent ones of the $R^{S4}$, $R^{S5}$, $R^{S6}$, and $R^{S7}$ [groups] may bond to each other to form a saturated or unsaturated carbon ring. Examples of the aforementioned saturated or unsaturated carbon ring include naphthalene, azulene, anthracene, fluorene, and phenalene. $R^{S4}$, $R^{S5}$, $R^{S6}$, and $R^{S7}$ are preferably a hydrogen atom, a substituted or unsubstituted $C_1$ to $C_{30}$ alkyl group, a substituted or unsubstituted $C_6$ to $C_{30}$ aryl group, a substituted or unsubstituted $C_5$ to $C_{30}$ condensed polycyclic group, or a cyano group, with a hydrogen atom being more preferable.

$Ar^{S3}$ represents a substituted or unsubstituted $C_6$ to $C_{30}$ aryl group or a substituted or unsubstituted $C_2$ to $C_{30}$ heteroaryl group. $Ar^{S3}$ is preferably a substituted or unsubstituted phenyl group.

Next, General Formula Sc-1 above will be described.

In General Formula Sc-1 above, $R^{S8}$ and $R^{S9}$ represent each independently a hydrogen atom, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S8}$ and $R^{S9}$ are preferably a substituted or unsubstituted $C_1$ to $C_{30}$ alkyl group or a substituted or unsubstituted $C_6$ to $C_{30}$ aryl group, with a methyl group and a phenyl group being more preferable. $R^{S10}$ represents a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S10}$ preferably a substituted or unsubstituted $C_6$ to $C_{30}$ aryl group and more preferably a phenyl group. $R^{S11}$ and $R^{S12}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S11}$ and $R^{S12}$ [groups] may bond to each other to form a saturated or unsaturated carbon ring. Examples of the aforementioned saturated or unsaturated carbon ring include naphthalene, azulene, anthracene, fluorene, and phenalene. $R^{S11}$ and $R^{S12}$ are preferably a hydrogen atom, a substituted or unsubstituted $C_1$ to $C_{30}$ alkyl group, a substituted or unsubstituted $C_6$ to $C_{30}$ aryl group, a substituted or unsubstituted $C_5$ to $C_{30}$ condensed polycyclic group, or a cyano group, with a hydrogen atom being more preferable. $Ar^{S4}$ represents a substituted or unsubstituted $C_6$ to $C_{30}$ aryl group or a substituted or unsubstituted $C_2$ to $C_{30}$ heteroaryl group. $Y^{S1}$ and $Y^{S2}$ represent a substituted or unsubstituted $C_1$ to $C_{30}$ alkylene or a substituted or unsubstituted $C_6$ to $C_{30}$ arylene. $Y^{S1}$ and $Y^{S2}$ are preferably a substituted or unsubstituted $C_6$ to $C_{30}$ arylene, with a substituted or unsubstituted phenylene being more preferable. n is an integer from 0 to 5, preferably from 0 to 3, more preferably from 0 to 2, and even more preferably 0. m is an integer from 0 to 5, preferably from 0 to 3, more preferably from 0 to 2, and even more preferably 1.

General Formula Sa-1 above is preferably a compound expressed by General Formula Sa-2 below:

[Twenty-Sixth Chemical Formula]

General Formula Sa-2

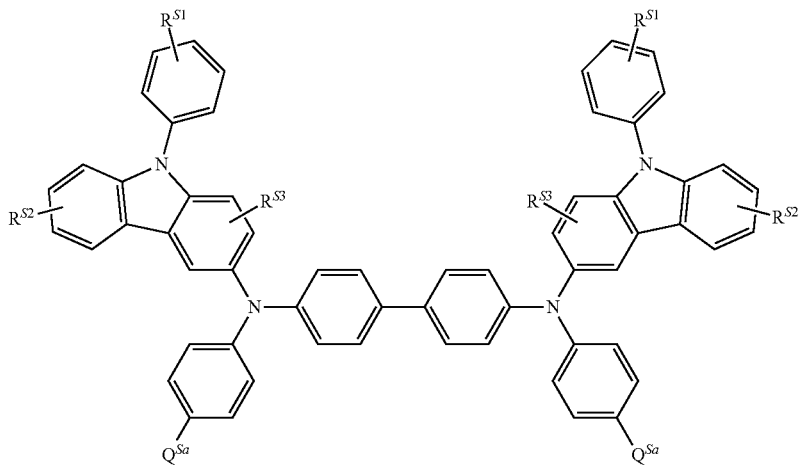

(In the formula, $R^{S1}$, $R^{S2}$, and $R^{S3}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent ones of the $R^{S1}$, $R^{S2}$, $R^{S3}$ [groups] may bond to each other to form a saturated or unsaturated carbon ring. $Q^{Sa}$ [groups] represent each independently a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group.)

General Formula Sa-2 above will now be described. $R^{S1}$, $R^{S2}$, and $R^{S3}$ are defined the same as those in General Formula Sa-1, and the preferred ranges are also the same. $Q^{Sa}$[groups] represent each independently a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group. $Q^{Sa}$ is preferably a hydrogen atom, a cyano group, a fluorine atom, a substituted or unsubstituted $C_1$ to $C_{30}$ alkyl group, or a substituted or unsubstituted $C_6$ to $C_{30}$ aryl group, more preferably a hydrogen atom or a substituted or unsubstituted $C_1$ to $C_{30}$ alkyl group, and even more preferably a hydrogen atom.

General Formula Sb-1 above is preferably a compound expressed by General Formula Sb-2 below:

[Twenty-Seventh Chemical Formula]

General Formula Sb-2

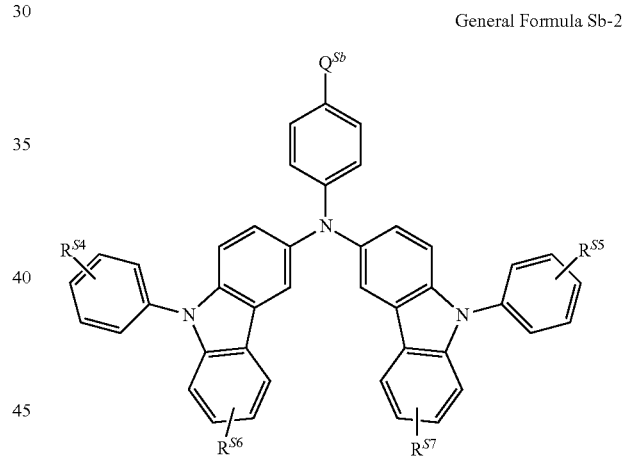

(In the formula, $R^{S4}$, $R^{S5}$, $R^{S6}$, and $R^{S7}$ represent represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent ones of the $R^{S4}$, $R^{S5}$, $R^{S6}$, and $R^{S7}$ [groups] may bond to each other to form a saturated or unsaturated carbon ring. $Q^{Sb}$ represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group.)

General Formula Sb-2 above will now be described. $R^{S4}$, $R^{S5}$, $R^{S6}$, and $R^{S7}$ are defined the same as those in General Formula Sb-1, and the preferred ranges are also the same.

$Q^{Sa}$ [sic]⁶ represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group. $Q^{Sa}$ [sic] is preferably a hydrogen atom, a cyano group, a fluorine atom, a substituted or unsubstituted $C_1$ to $C_{30}$ alkyl group, or a substituted or unsubstituted $C_6$ to $C_{30}$ aryl group, more preferably a hydrogen atom or a substituted or unsubstituted $C_1$ to $C_{30}$ alkyl group, and even more preferably a hydrogen atom.

⁶Translator's note: apparent error in the original; "$Q^{Sa}$" should be "$Q^{Sb}$" (same below).

General Formula Sc-1 above is preferably a compound expressed by General Formula Sc-2 below:

[Twenty-Eighth Chemical Formula]

General Formula Sc-2

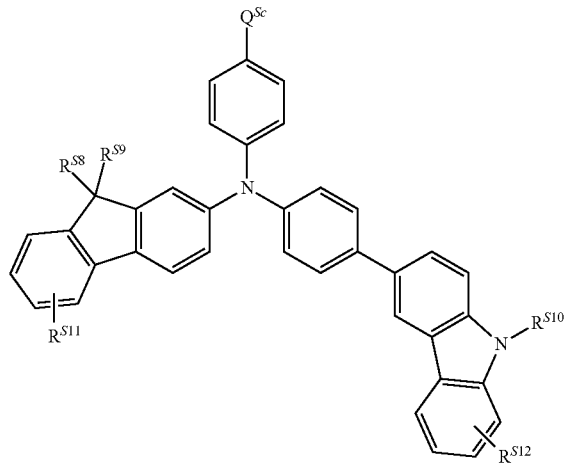

(In the formula, $R^{s8}$ and $R^{s9}$ represent each independently a hydrogen atom, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S10}$ represents a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S11}$ and $R^{s12}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S11}$ and $R^{s12}$ [groups] may bond to each other to form a saturated or unsaturated carbon ring. $Q^{Sc}$ represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group.)

General Formula Sc-2 above will now be described. $R^{S8}$, $R^{S9}$, $R^{S10}$, $R^{S11}$, and $R^{S12}$ are defined the same as those in General Formula Sc-1, and the preferred ranges are also the same. $Q^{Sc}$ represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group. $Q^{Sc}$ is preferably a hydrogen atom, a cyano group, a fluorine atom, a substituted or unsubstituted $C_1$ to $C_{30}$ alkyl group, or a substituted or unsubstituted $C_6$ to $C_{30}$ aryl group, more preferably a hydrogen atom or a substituted or unsubstituted $C_6$ to $C_{30}$ aryl group, and even more preferably a phenyl group.

Concrete examples of compounds expressed by General Formulas Sa-1, Sb-1, and Sc-1 above are as follows, but the present invention is not limited to or by the following concrete examples:

[Twenty-Ninth Chemical Formula]

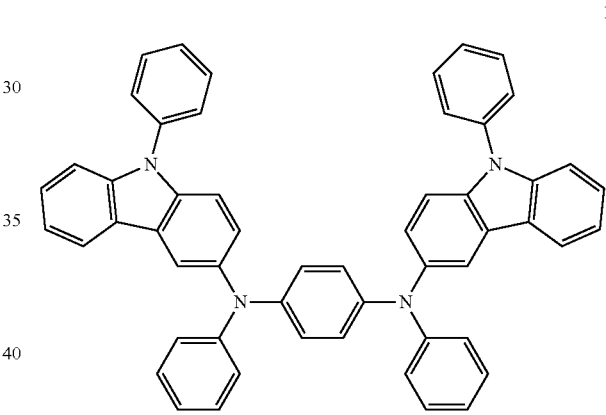

1

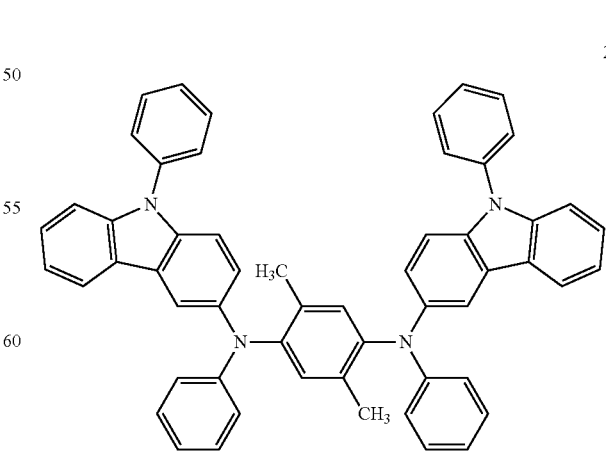

2

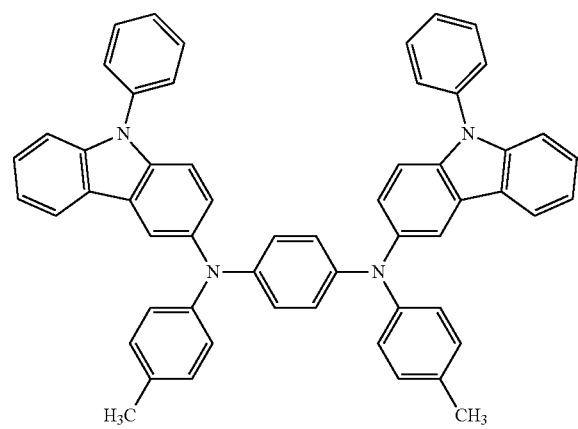
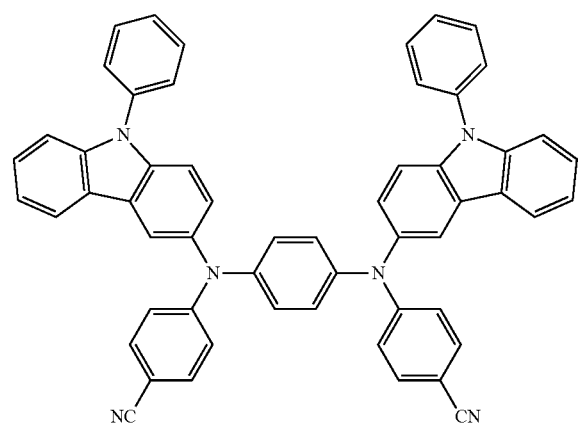
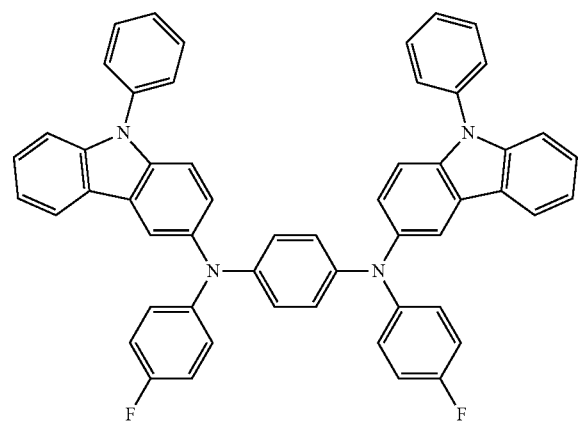
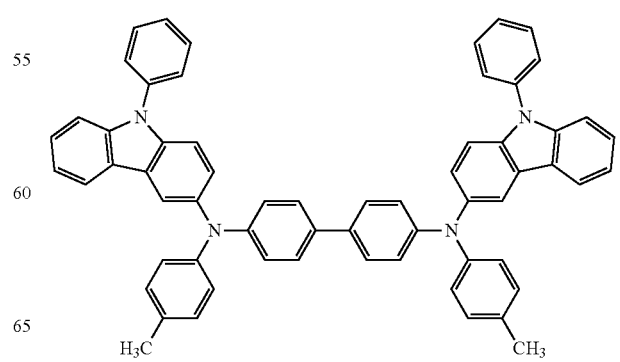
[Thirtieth Chemical Formula]

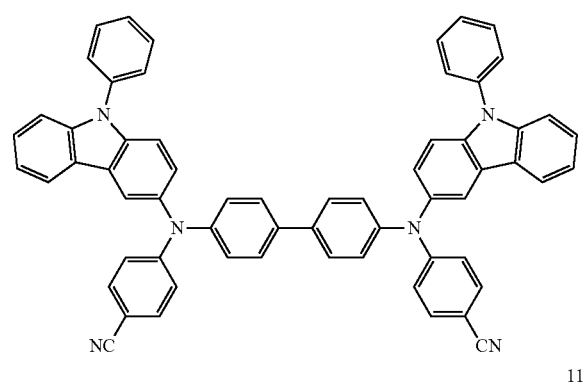
10
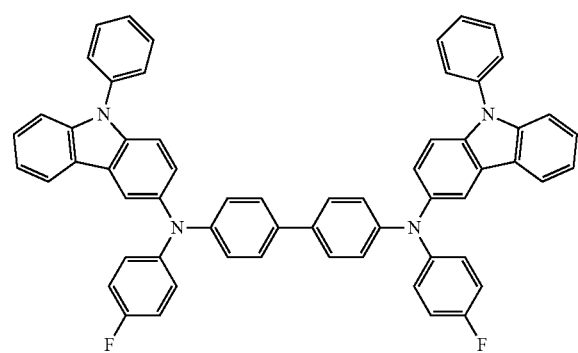
11
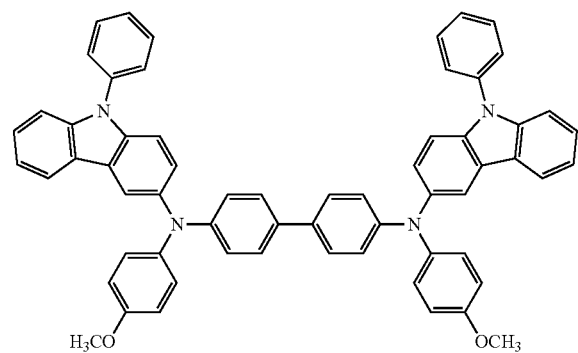
12
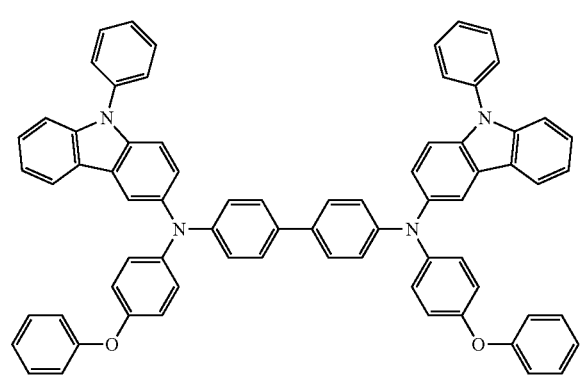
13
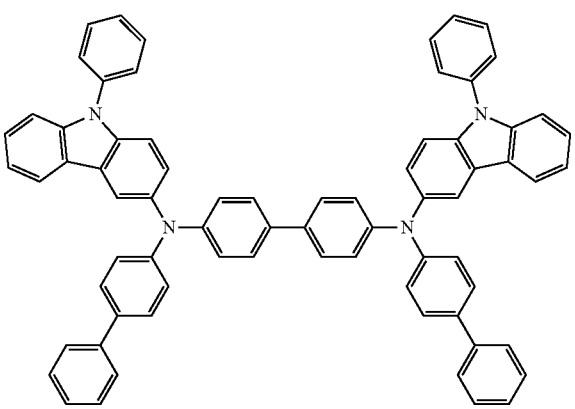
14
[Thirty-First Chemical Formula]
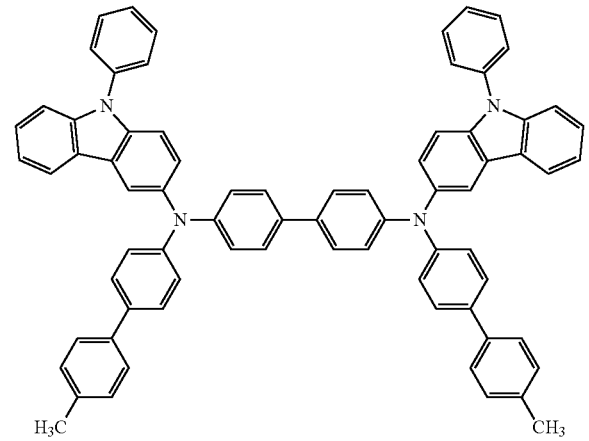
15
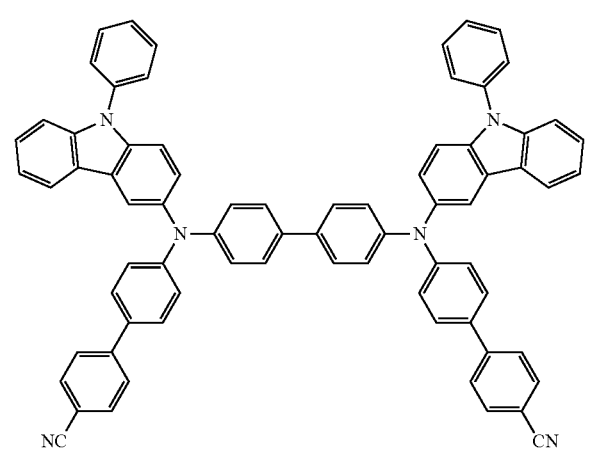
16

17
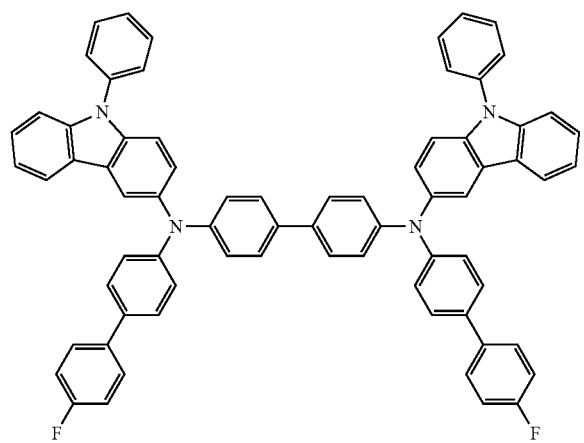
18
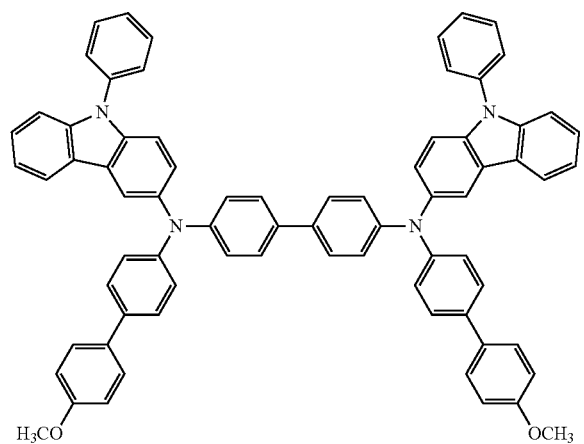
19
20
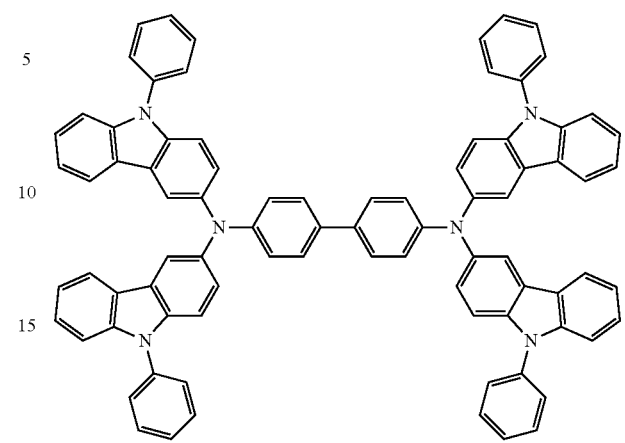
[Thirty-Second Chemical Formula]
21
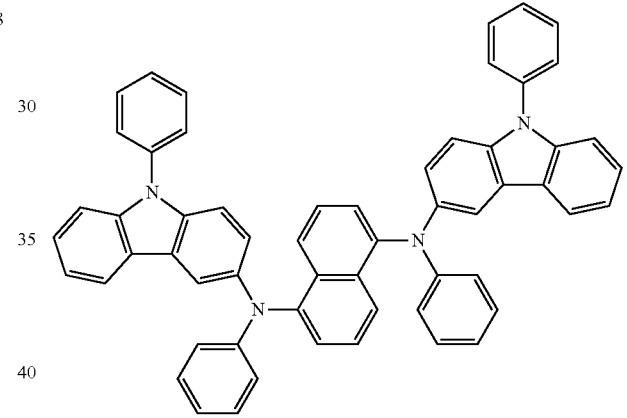
22
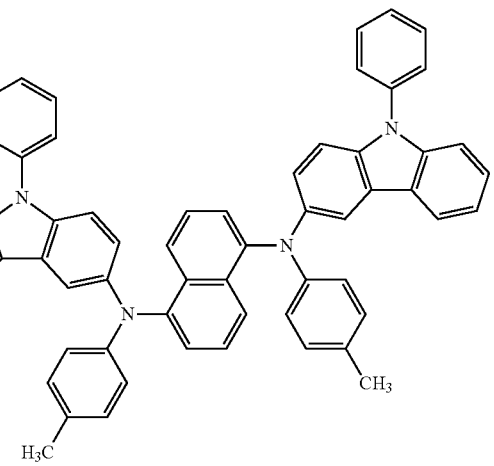

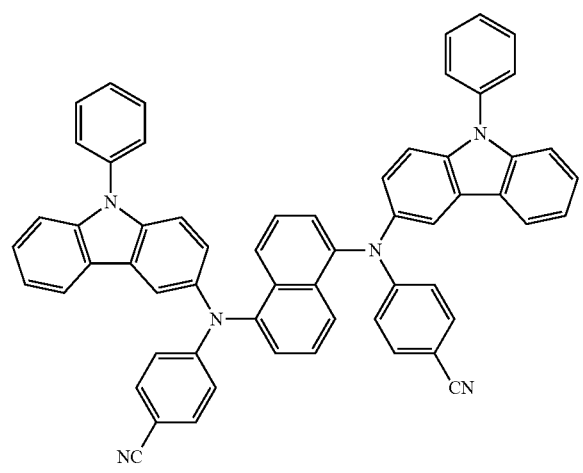
23
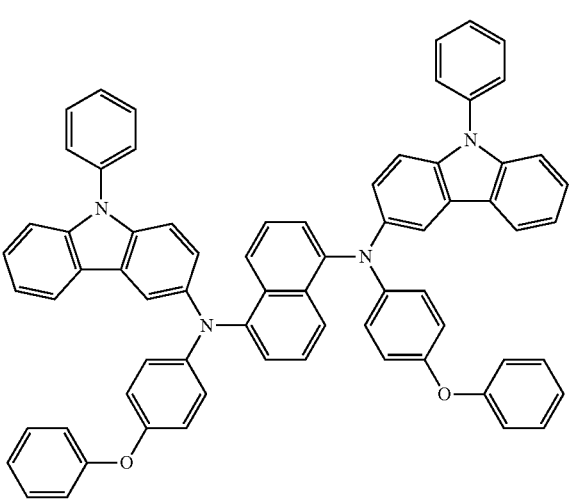
26
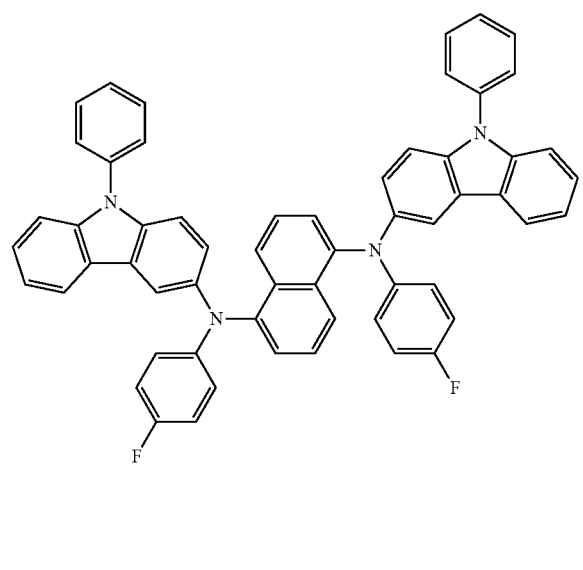
24
[Thirty-Third Chemical Formula]
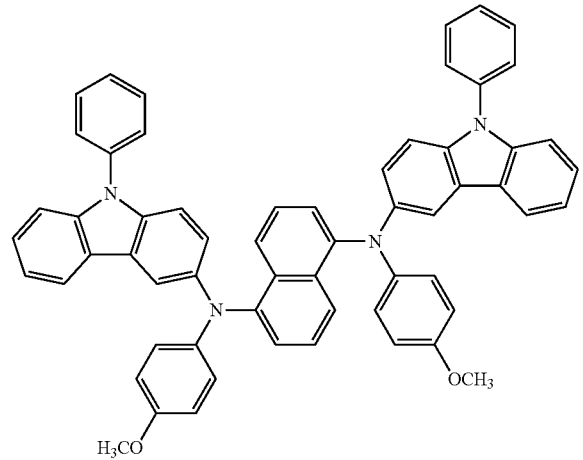
25
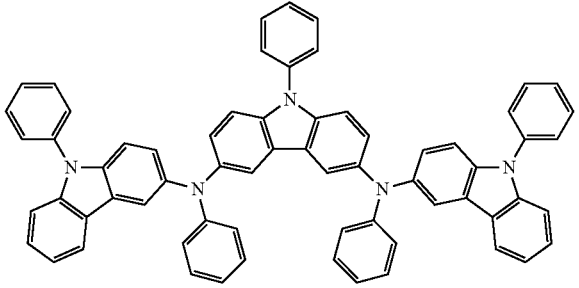
27
28

29
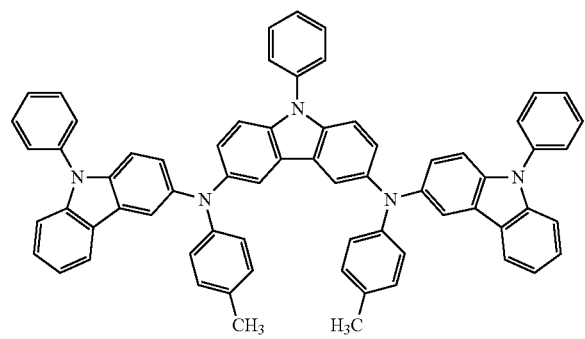
30
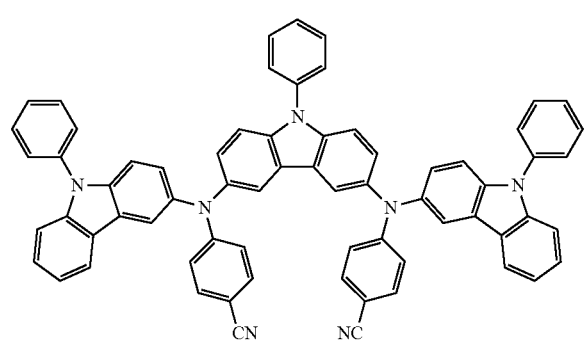
31
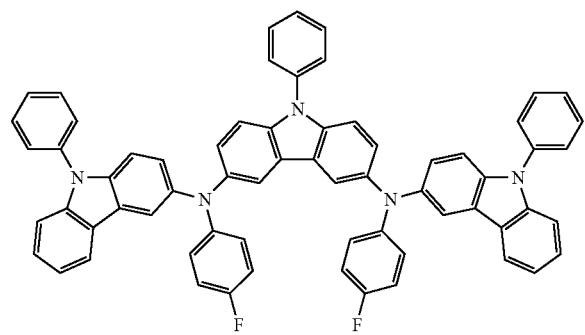
32
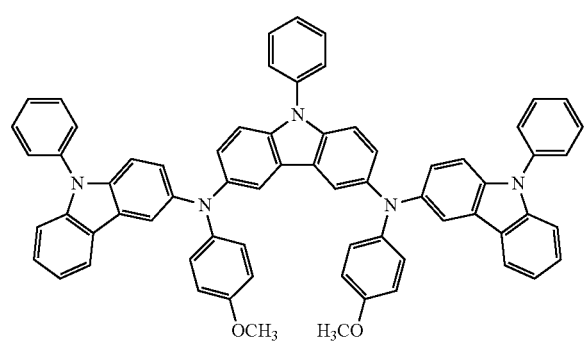
[Thirty-Fourth Chemical Formula]
33
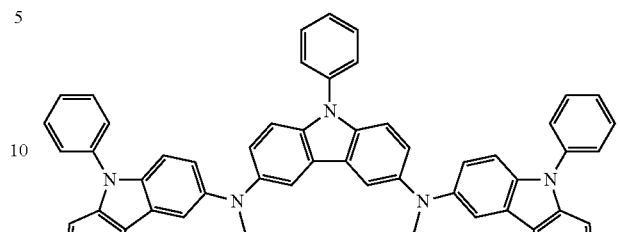
34
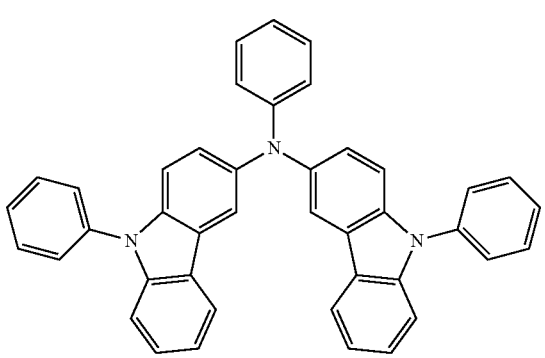
35
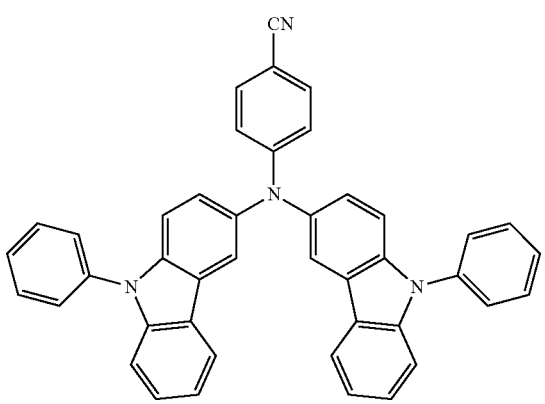
36
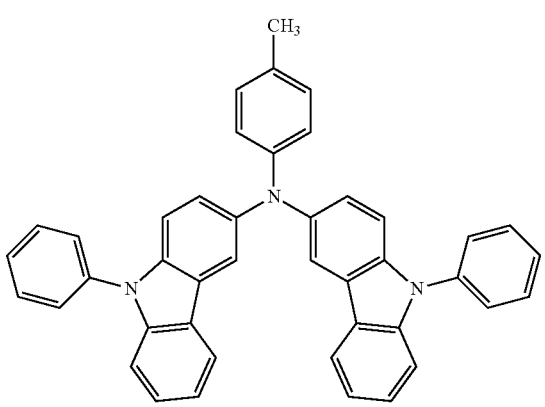

37
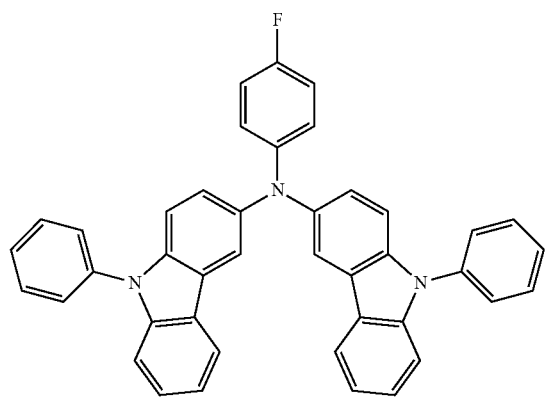
38
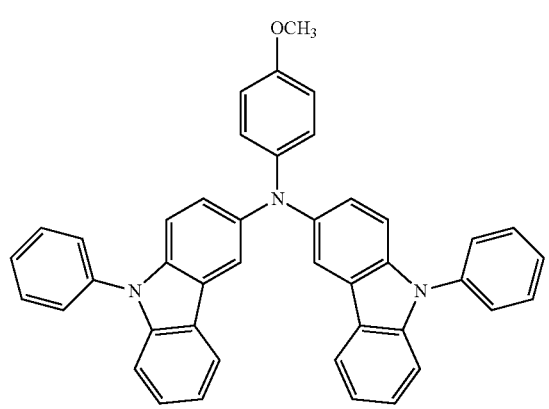
[Thirty-Fifth Chemical Formula]
39
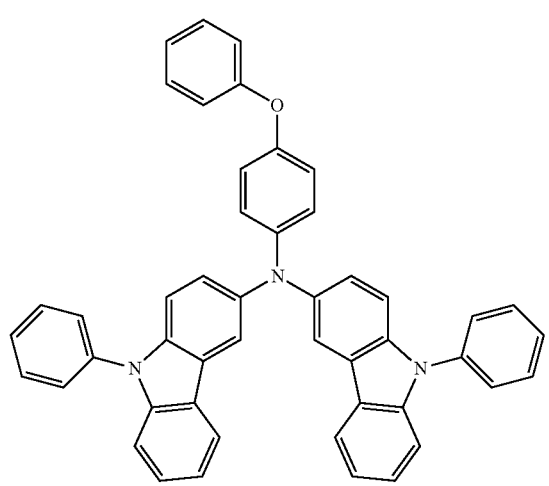
40
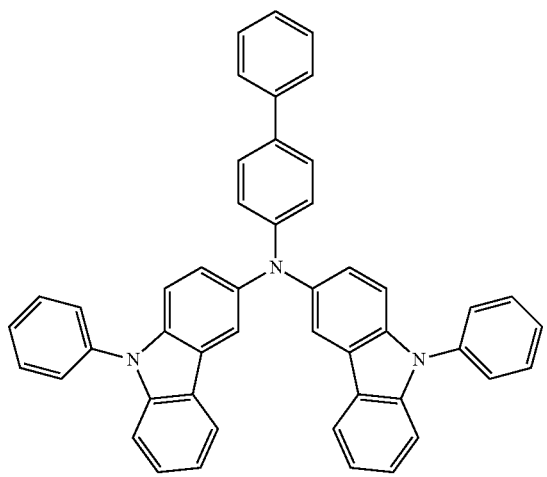
41
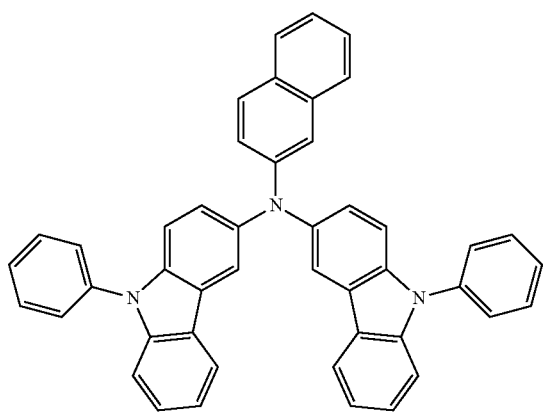
42
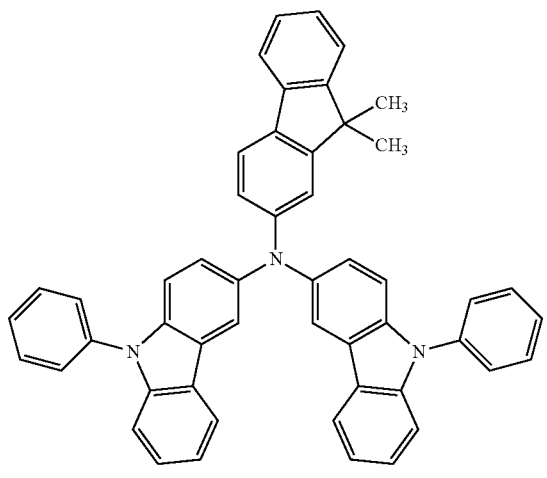

[Thirty-Sixth Chemical Formula]
43
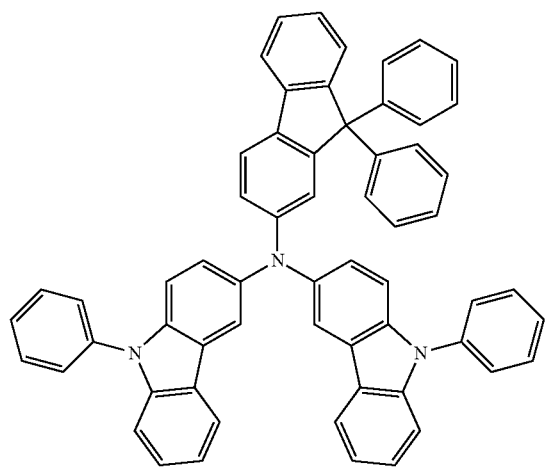
44
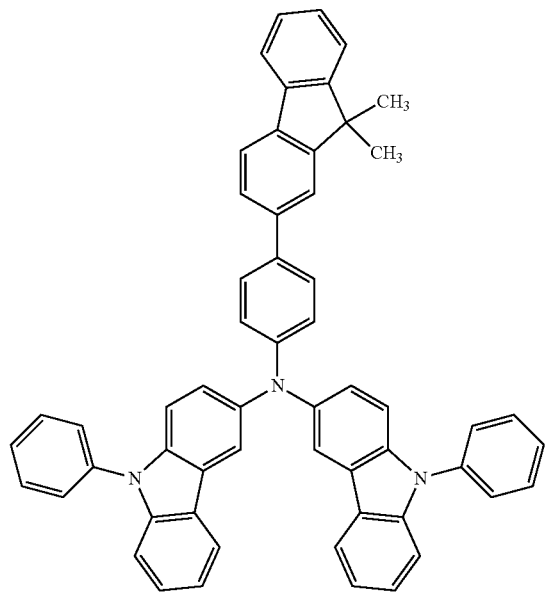
45
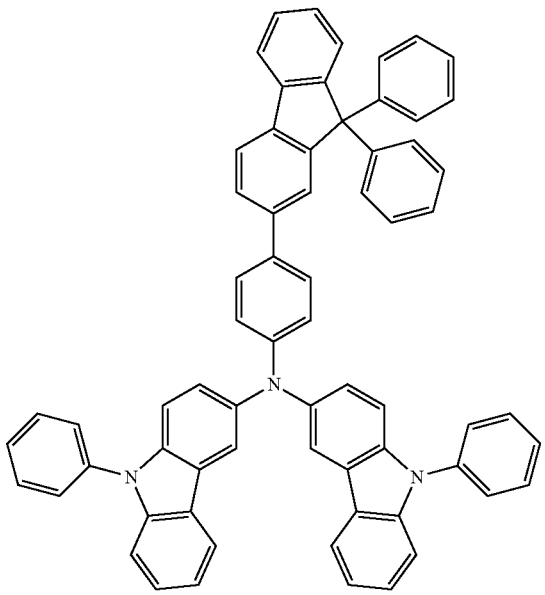
46
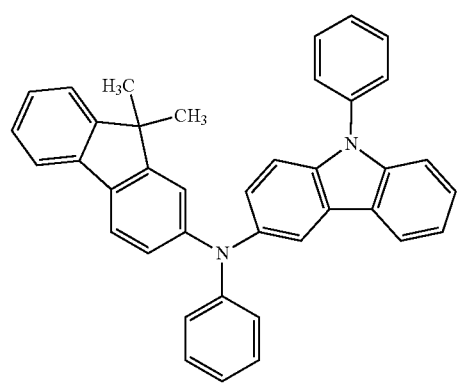
[Thirty-Seventh Chemical Formula]
47
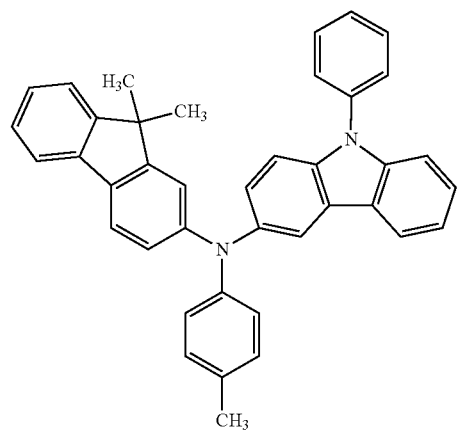

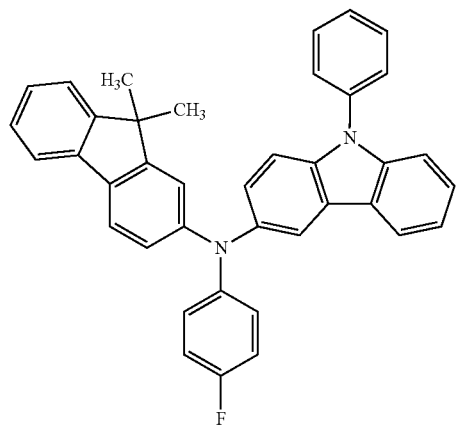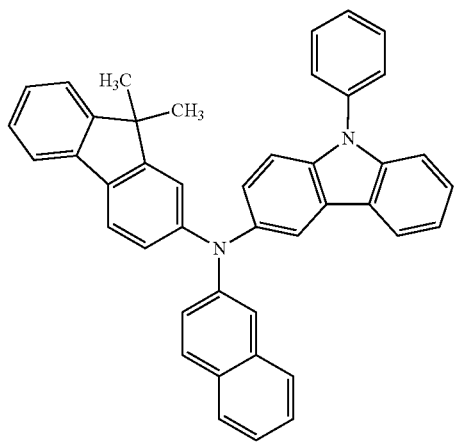

54
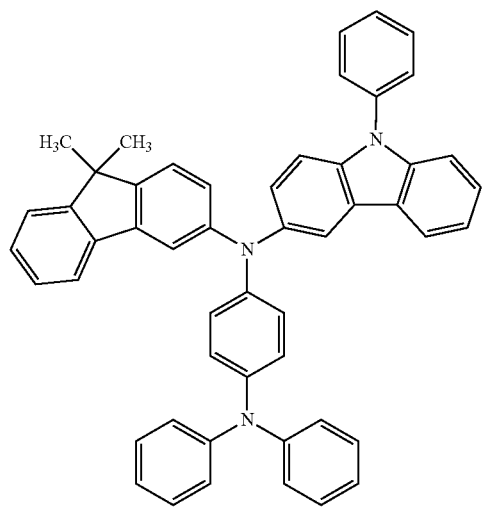
57
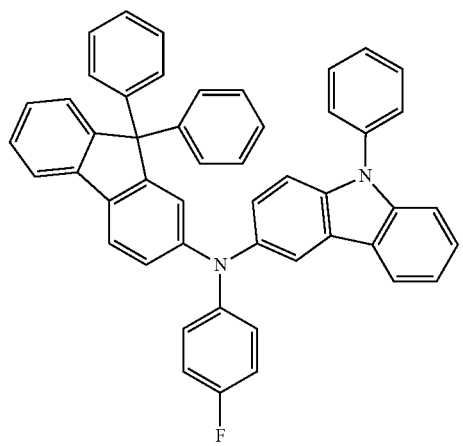
55
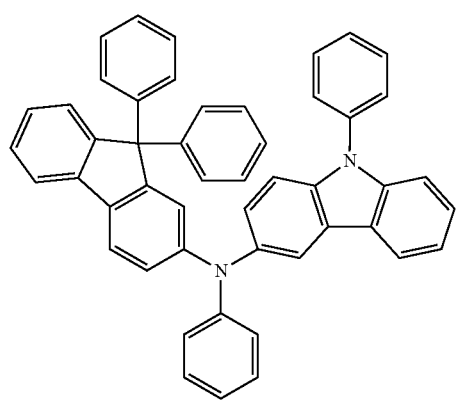
58
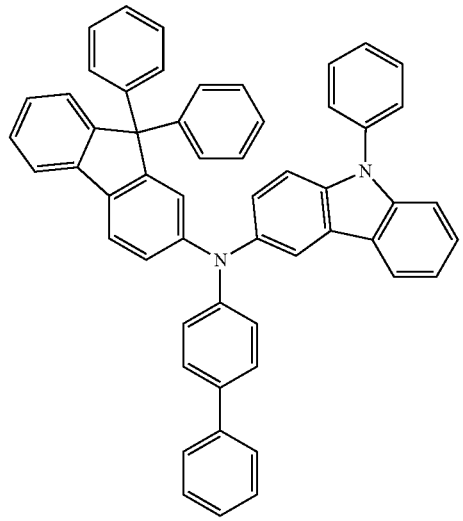
[Thirty-Eighth Chemical Formula]
56
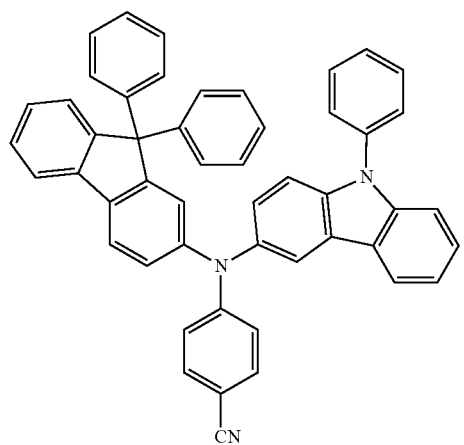
59
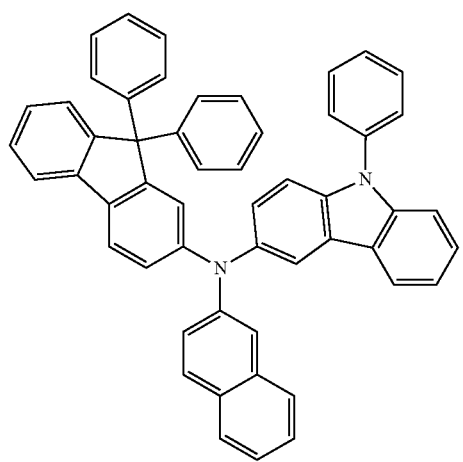

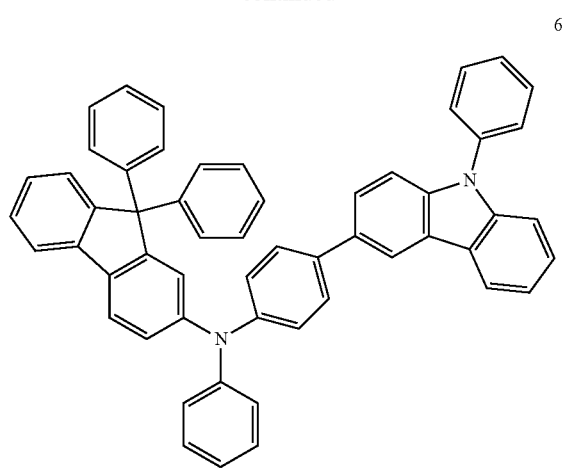

60

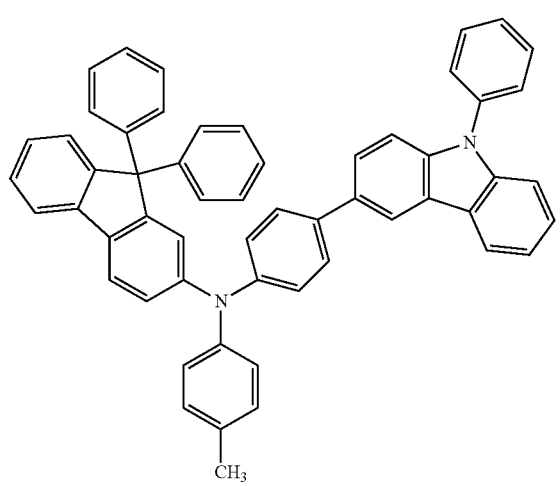

61

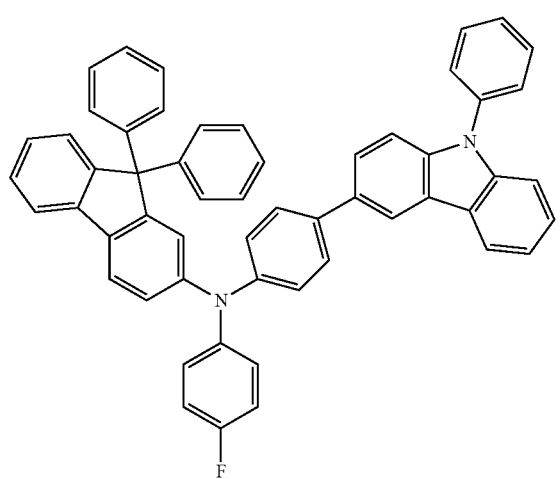

62

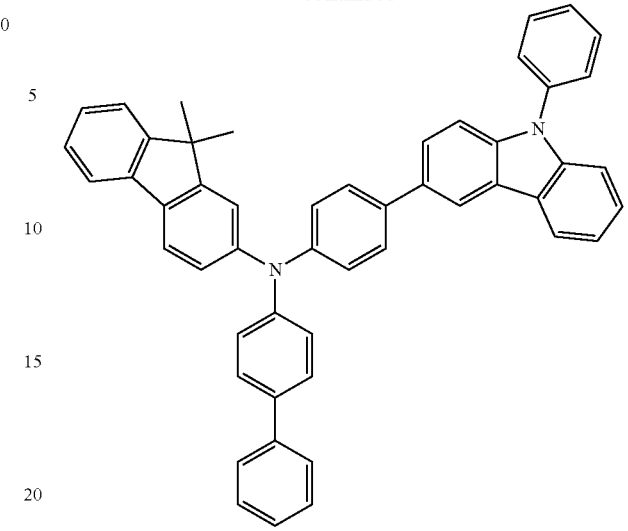

5

The compounds expressed by General Formula Sa-1, Sb-1, or Sc-1 above can be synthesized by the methods described in Japanese Laid-Open Patent Application 2007-318101. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the light-emitting element of the present invention, the compound expressed by General Formula Sa-1, Sb-1, or Sc-1 above is preferably contained in an organic layer between the aforementioned light-emitting layer and the aforementioned anode, and it is more preferably contained in the layer adjacent to the light-emitting layer on the anode side among the [organic layers]. It is especially preferable if it is the hole transport material contained in the hole transport layer.

The compound expressed by General Formula Sa-1, Sb-1, or Sc-1 above is preferably contained in an amount of 70 to 100 wt % and more preferably 85 to 100 wt % with respect to the total weight of the organic layer to which [this compound is] added.

Besides these, regarding the hole injection layer and hole transport layer, what is stated in paragraph numbers [0165] to [0167] of Japanese Laid-Open Patent Application 2008-270736 can be applied to the present invention.

The aforementioned hole injection layer preferably contains an electron-accepting dopant. The effects of having the hole injection layer contain an electron-accepting dopant are that hole injection is enhanced, drive voltage decreases, efficiency is higher, and so forth. The electron-accepting dopant may be either an organic material or inorganic material as long as it is a material capable of pulling electrons from the doped material and generating radical cations, but examples include tetracyanoquinodimethane (TCNQ), tetrafluorotetracyanoquinodimethane ($F_4$-TCNQ), and molybdenum oxide.

The electron-accepting dopant in the aforementioned hole injection layer is preferably contained in an amount of 0.01 to 50 wt %, more preferably 0.1 to 40 wt %, and even more preferably 0.2 to 30 wt %, with respect to the weight of all the compounds forming the hole injection layer.

(A-2) Electron Blocking Layer

The electron blocking layer is a layer having the function of preventing the electrons transported from the cathode side to the light-emitting layer from escaping to the anode side. In the present invention, an electron blocking layer can be provided as an organic layer that is adjacent to the light-emitting layer on the anode side.

As examples of organic compounds that constitute an electron blocking layer, those listed above as examples of hole transport materials can be used.

The thickness of the electron blocking layer is preferably 1 to 500 nm, more preferably 3 to 100 nm, and even more preferably 5 to 50 nm.

The electron blocking layer may have a single-layer structure composed of one or more types of the aforementioned materials, or may have a multilayer structure composed of a plurality of layers of the same composition or different compositions.

From the standpoints of color purity, luminous efficiency, and drive durability, the material used in the electron blocking layer preferably has [an $S_1$ energy] higher than the $S_1$ energy of the aforementioned light-emitting material. The $S_1$ in a film state of the material used in the electron blocking layer is preferably at least 0.1 eV higher than the $S_1$ of the light-emitting material, more preferably at least 0.2 eV higher, and even more preferably at least 0.3 eV higher.

(B) Organic Layers Preferably Disposed Between the Cathode and the Aforementioned Light-Emitting Layer Next, (B) organic layers preferably disposed between the aforementioned cathode and the aforementioned light-emitting layer will be described.

(B-1) Electron Injection Layer and Electron Transport Layer

The electron injection layer and the electron transport layer are layers having the function of accepting electrons from the cathode or the cathode side and transporting them to the anode side. The electron injection material and electron transport material used for these layers may be compounds with either a low or a high molecular weight.

The compounds expressed by General Formula 1 above, for example, can be used as electron transport materials. Other electron transport materials are preferably selected from among a pyridine derivative, a quinoline derivative, a pyrimidine derivative, a pyrazine derivative, a phthalazine derivative, a phenanthroline derivative, a triazine derivative, a triazole derivative, an oxazole derivative, an oxadiazole derivative, an imidazole derivative, a benzimidazole derivative, an imidazopyridine derivative, a fluorenone derivative, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, an aromatic tetracarboxylic acid anhydride such as naphthalene and perylene, a phthalocyanine derivative, various metal complexes typified by metal complexes of an 8-quinolinol derivative, metal phthalocyanine, and metal complexes having benzoxazole or benzothiazole as a ligand, an organic silane derivative typified by silole, condensed ring hydrocarbon compounds (such as naphthalene, anthracene, phenanthrene, triphenylene, and pyrene), and the like, with a pyridine derivative, a benzimidazole derivative, an imidazopyridine derivative, a metal complex, or a condensed ring hydrocarbon compound being more preferable.

From the standpoint of lowering the drive voltage, the thickness of the electron injection layer and electron transport layer is preferably no more than 500 nm for each.

The thickness of the electron transport layer is preferably 1 to 500 nm, more preferably 5 to 200 nm, and even more preferably 10 to 100 nm. In addition, the thickness of the electron injection layer is preferably 0.1 to 200 nm, more preferably 0.2 to 100 nm, and even more preferably 0.5 to 50 nm.

The electron injection layer and the electron transport layer may have a single-layer structure composed of one or more types of the aforementioned materials, or a multilayer structure composed of a plurality of layers of the same composition or different compositions.

The electron injection layer preferably contains an electron-donating dopant. The effects of having the electron injection layer contain an electron-donating dopant are that electron injection is enhanced, drive voltage decreases, efficiency is higher, and so forth. The electron-donating dopant may be either an organic material or inorganic material as long as it is a material capable of giving electrons to the doped material and generating radical anions, but examples include tetrathiafulvalene (TTF), tetrathianaphthacene (TTT) [sic][7], bis-[1,3-diethyl-2-methyl-1,2-dihydrobenzimidazolyl] and other such dihydroimidazole compounds, lithium, and cesium.

[7]Translator's note: The abbreviation of "tetrathianaphthacene" should be "TTN," and "TTT" is "tetrathiatetracene," so this abbreviation "TTT" here seems to be an error in the original for "TTN."

The electron-donating dopant in the electron injection layer is preferably contained in an amount of 0.01 to 50 wt %, more preferably 0.1 to 40 wt %, and even more preferably 0.5 to 30 wt %, with respect to the weight of all the compounds forming the electron injection layer.

(B-2) Hole Blocking Layer

The hole blocking layer is a layer having the function of preventing the holes transported from the anode side to the light-emitting layer from escaping to the cathode side. In the present invention, a hole blocking layer can be provided as an organic layer that is adjacent to the light-emitting layer on the cathode side.

The $S_1$ energy in a film state of the organic compound constituting the hole blocking layer is preferably higher than the $S_1$ energy of the light-emitting material for the purpose of preventing energy movement of excitons generated in the light-emitting layer, thus preventing a decrease in luminous efficiency.

The compounds expressed by General Formula 1 above can be used as examples of organic compounds that constitute a hole blocking layer.

Examples of other organic compounds that constitute a hole blocking layer other than the compounds expressed by General Formula 1 above include aluminum(III) bis(2-methyl-8-quinolinato) 4-phenylphenolate (abbreviated as Balq) and other such aluminum complexes, triazole derivatives, and phenanthroline derivatives such as 2,9-dimethyl-4,7-diphenyl-1,10-phenanthroline (abbreviated as BCP).

The thickness of the hole blocking layer is preferably 1 to 500 nm, more preferably 3 to 100 nm, and even more preferably 5 to 50 nm.

The hole blocking layer may have a single-layer structure composed of one or more types of the aforementioned materials, or it may have a multilayer structure composed of a plurality of layers of the same composition or different compositions.

From the standpoints of color purity, luminous efficiency, and drive durability, the material used in the hole blocking layer preferably has [an $S_1$ energy] higher than the $S_1$ energy of the aforementioned light-emitting material. The $S_1$ in a film state of the material used in the hole blocking layer is preferably at least 0.1 eV higher than the $S_1$ of the light-emitting material, more preferably at least 0.2 eV higher, and even more preferably at least 0.3 eV higher.

(B-3) Materials Especially Preferably Used in the Organic Layers Preferably Disposed Between the Cathode and the Aforementioned Light-Emitting Layer In the organic electroluminescent element of the present invention, examples of materials especially preferably used as the materials of (B) the organic layers preferably disposed between the aforementioned cathode and the aforementioned light-emitting layer include compounds expressed by General Formula 1 above, compounds expressed by General Formula P-1 below, and compounds expressed by General Formula O-1 below.

Compounds expressed by the aforementioned General Formula O-1 and compounds expressed by the aforementioned General Formula P-1 will be described below.

The organic electroluminescent element of the present invention preferably includes at least one organic layer between the light-emitting layer and the cathode, and from the standpoints of the drive voltage and efficiency of the element, this organic layer preferably contains at least one type of compound expressed by General Formula O-1 below. General Formula O-1 will be described below:

[Thirty-Ninth Chemical Formula]

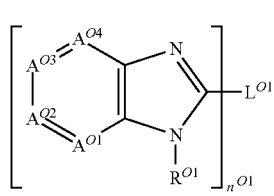

General Formula O-1

(In General Formula O-1, $R^{O1}$ represents an alkyl group, an aryl group, or a heteroaryl group. $A^{O1}$ to $A^{O4}$ represent each independently C—$R^A$ or a nitrogen atom. $R^A$ represents a hydrogen atom, an alkyl group, an aryl group, or a heteroaryl group, and the plurality of $R^A$ [groups] may be the same or different. $L^{O1}$ represents a divalent to hexavalent linking group composed of an aryl ring or a heteroaryl ring. $n^{O1}$ represents an integer from 2 to 6.)

$R^{O1}$ represents an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. $R^{O1}$ is preferably an aryl group or a heteroaryl group and more preferably an aryl group. Substituents that are preferable when the aryl group of $R^{O1}$ has a substituent include an alkyl group, an aryl group, and a cyano group, with an alkyl group or aryl group being more preferable, and an aryl group being even more preferable. If the aryl group of $R^{O1}$ has a plurality of substituents, the plurality of substituents may bond to each other to form a five- or six-membered ring. The aryl group of $R^{O1}$ is preferably a phenyl group that may have a substituent selected from Substituent Group A, more preferably a phenyl group that may be substituted with an alkyl group or an aryl group, and even more preferably an unsubstituted phenyl group or a 2-phenylphenyl group.

$A^{O1}$ to $A^{O4}$ represent each independently C—$R^A$ or a nitrogen atom. It is preferable for zero to two of $A^{O1}$ to $A^{O4}$ to be a nitrogen atom, and it is more preferable for zero or one to be a nitrogen atom. Preferably all of $A^{O1}$ to $A^{O4}$ are C—$R^A$, or $A^{O1}$ is a nitrogen atom and $A^{O2}$ to $A^{O4}$ are C—$R^A$, more preferably $A^{O1}$ is a nitrogen atom and $A^{O2}$ to $A^{O4}$ are C—$R^A$, and even more preferably $A^{O1}$ is a nitrogen atom, $A^{O2}$ to $A^{O4}$ are C—$R^A$, and all of the $R^A$ [groups] are hydrogen atoms.

$R^A$ represents a hydrogen atom, an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. Furthermore, the plurality of $R^A$ [groups] may be the same or different. $R^A$ is preferably a hydrogen atom or an alkyl group and more preferably a hydrogen atom.

$L^{O1}$ represents a divalent to hexavalent linking group composed of an aryl ring (preferably $C_6$ to $C_{30}$) or a heteroaryl ring (preferably $C_4$ to $C_{12}$). $L^{O1}$ is preferably an arylene group, a heteroarylene group, an aryltolyl group, or a heteroaryltolyl group, more preferably a phenylene group, a biphenylene group, or a benzenetriyl group, and even more preferably a biphenylene group or a benzenetriyl group. $L^{O1}$ may have a substituent selected from the aforementioned Substituent Group A, and if there is a substituent, the substituent is preferably an alkyl group, an aryl group, or a cyano group. Concrete examples of $L^{O1}$ are listed below:

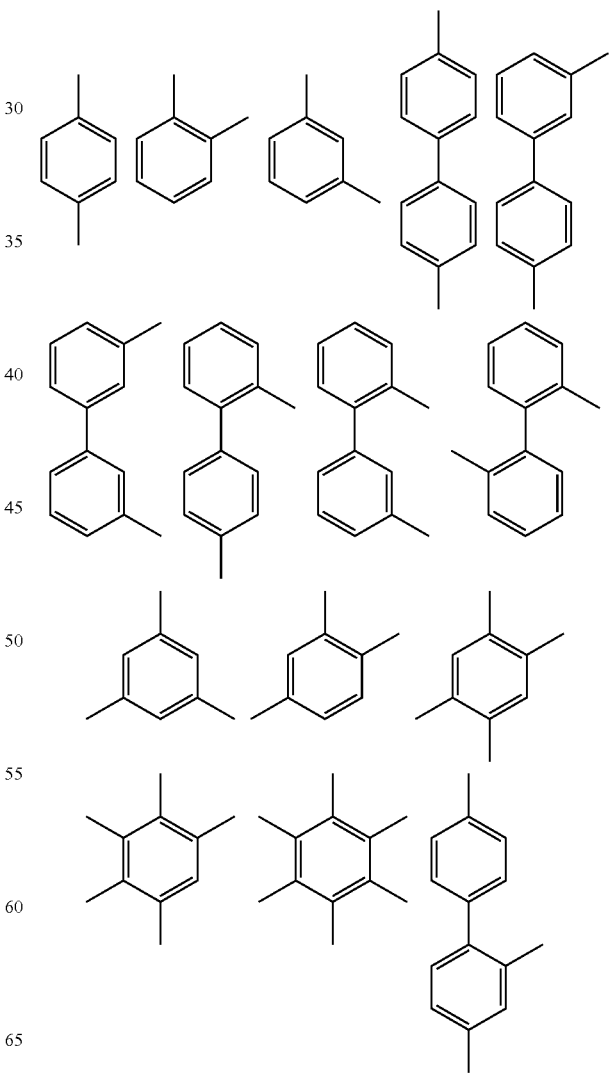

101

-continued

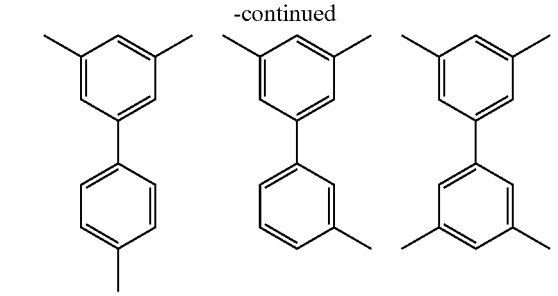

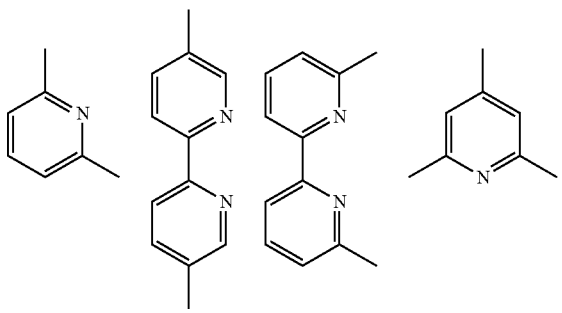

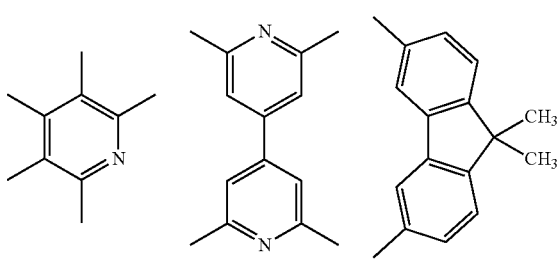

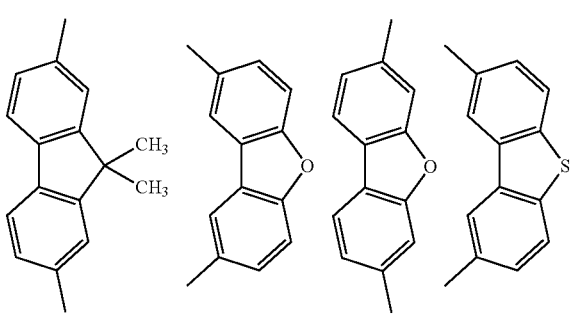

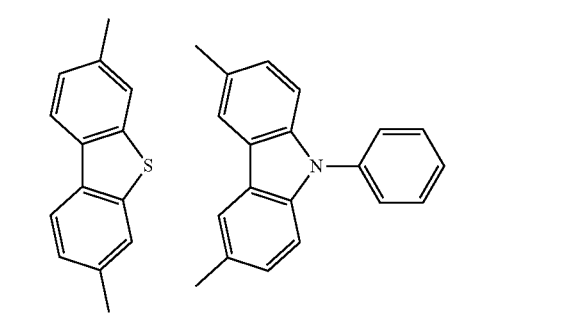

102

-continued

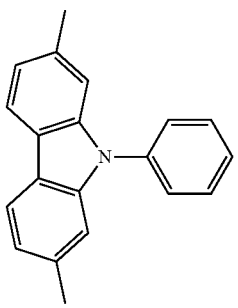

$n^{O1}$ represents an integer from 2 to 6 and is preferably an integer from 2 to 4, and more preferably 2 or 3. From the standpoint of efficiency of the element, $n^{O1}$ is most preferably 3, and from the standpoint of durability of the element, 2 is most preferable.

From the standpoints of stability during high-temperature storage and stable operation with respect to heat emission during high-temperature drive and during drive [sic], the glass transition temperature (Tg) of the compound expressed by General Formula O-1 above is preferably from 100° C. to 300° C., more preferably from 120° C. to 300° C., even more preferably from 120° C. to 300° C., and even still more preferably from 140° C. to 300° C.

Concrete examples of the compound expressed by General Formula O-1 will be given below, but it should not be construed that the compounds expressed by General Formula O-1 that can be used in the present invention are limited to or by these concrete examples:

[Forty-First Chemical Formula]

OM-1

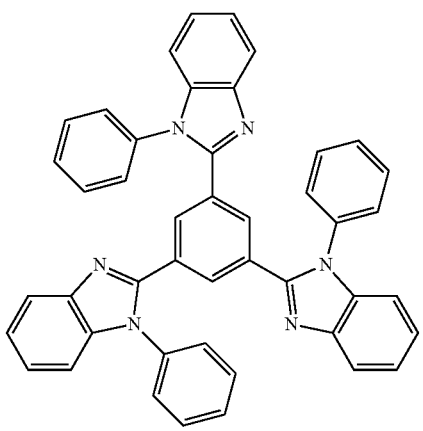

-continued
OM-2
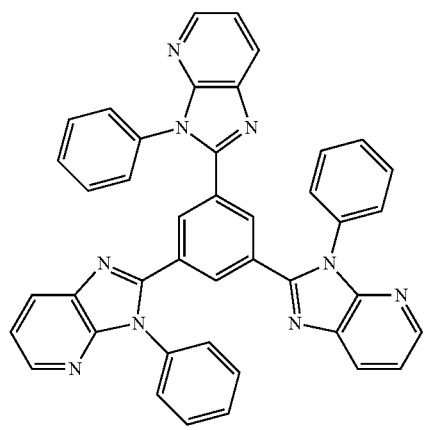
OM-3
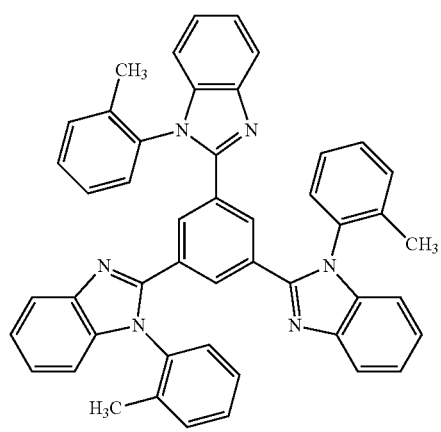
OM-4
-continued
OM-5
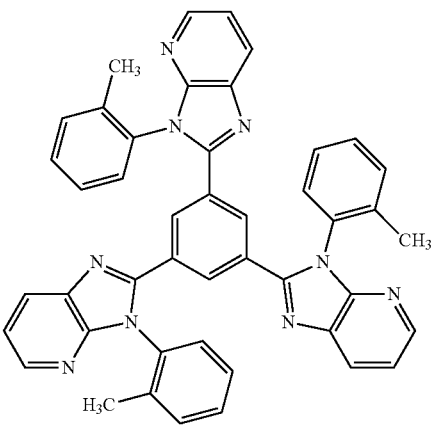
OM-6
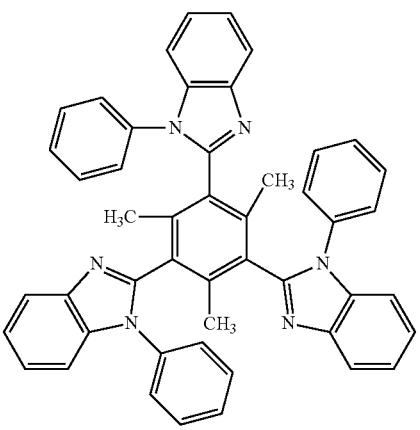
OM-7
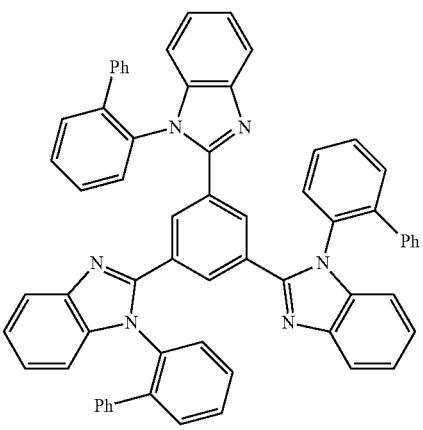

OM-8
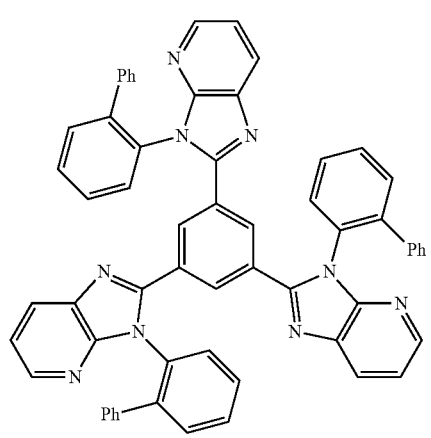
OM-9
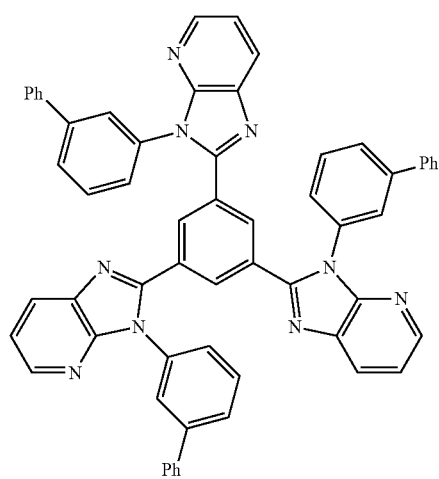
[Forty-Second Chemical Formula]
OM-10
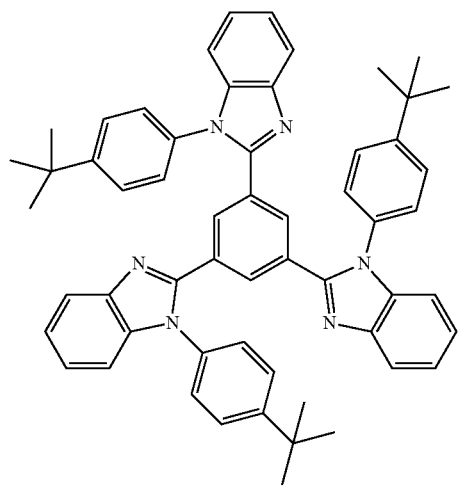
OM-11
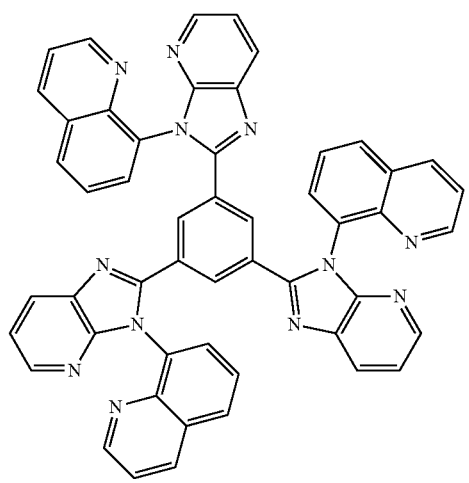
OM-12
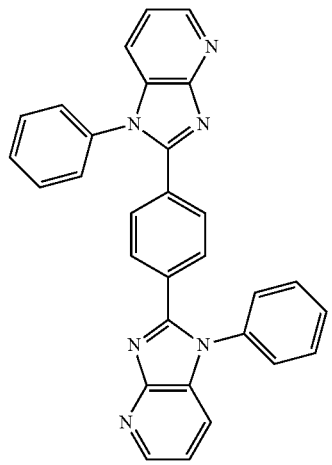
OM-13
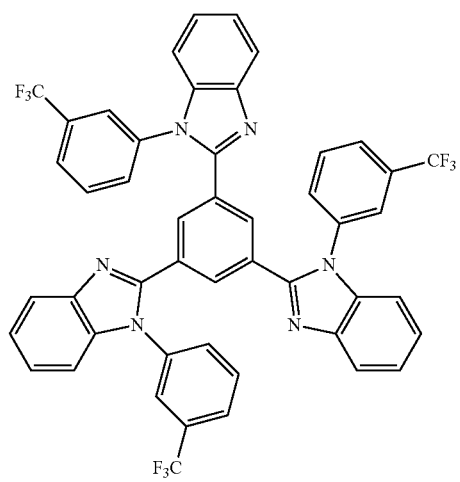

-continued

OM-14

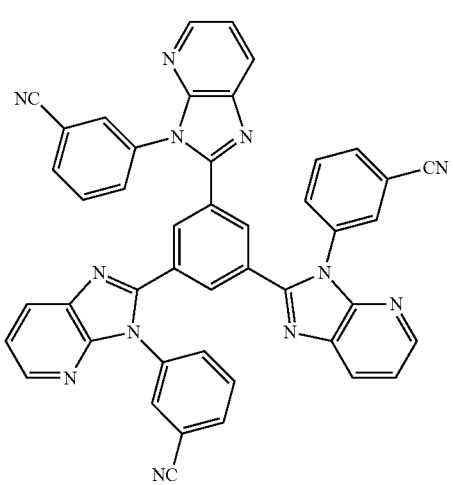

OM-15

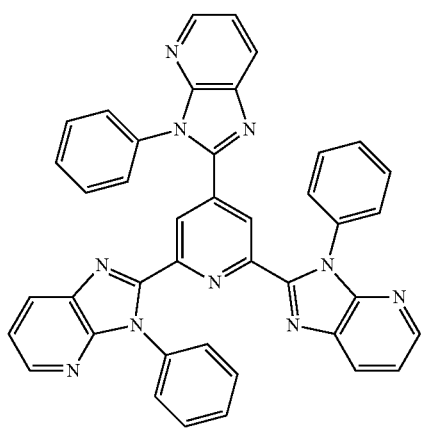

OM-16

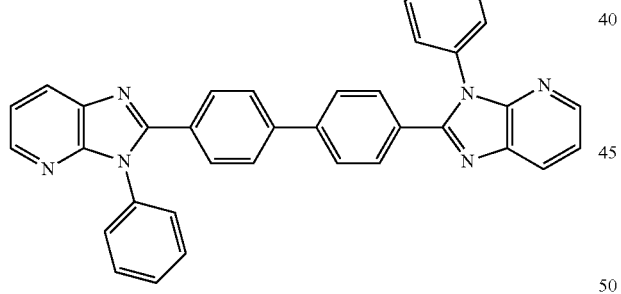

The compounds expressed by General Formula O-1 above can be synthesized by the method described in Japanese Laid-Open Patent Application 2001-335776. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the organic electroluminescent element of the present invention, a compound expressed by General Formula O-1 is preferably contained in an organic layer between the light-emitting layer and the cathode, but it is more preferably contained in the layer adjacent to the light-emitting layer on the cathode side.

The compound expressed by General Formula O-1 is preferably contained in an amount of 70 to 100 wt % and more preferably 85 to 100 wt % with respect to the total weight of the organic layer to which [this compound is] added.

The organic electroluminescent element of the present invention preferably includes at least one organic layer between the light-emitting layer and the cathode, and from the standpoints of the drive voltage and efficiency of the element, this organic layer preferably contains at least one type of compound expressed by General Formula P below. General Formula P will be described below:

[Forty-Third Chemical Formula]

General Formula P

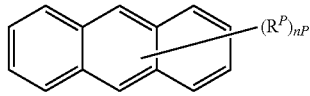

In General Formula P, $R^P$ represents an alkyl group (preferably $C_1$ to $C_8$), an aryl group (preferably $C_6$ to $C_{30}$), or a heteroaryl group (preferably $C_4$ to $C_{12}$), and these may have substituents selected from the aforementioned Substituent Group A. nP represents an integer from 1 to 10, and if there are a plurality of $R^P$ [groups], these may be the same or different. At least one $R^P$ is a substituent expressed by [one of] General Formulas P-1 to P-3 below:

[Forty-Fourth Chemical Formula]

General Formula P-1

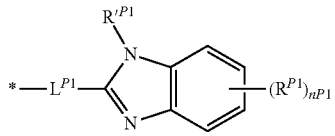

General Formula P-2

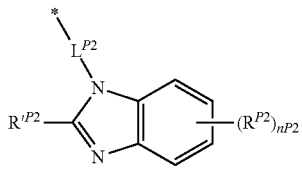

General Formula P-3

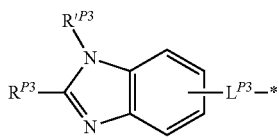

(In General Formulas P-1 to P-3, $R^{P1}$ to $R^{P3}$ and $R'^{P1}$ to $R'^{P3}$ represent each [independently] an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. $n^{P1}$ and $n^{P2}$ represent an integer from 0 to 4, and if there are a plurality of $R^{P1}$ to $R^{P3}$ and $R'^{P1}$ to $R'^{P3}$ [groups], these may be the same or different. $L^{P1}$ to $L^{P3}$ represent either a single bond or a divalent linking group composed of an aryl ring or a heteroaryl ring. The asterisk indicates the bonding position with an anthracene ring in General Formula P.)

A substituent favorable as $R^P$ other than the substituents expressed by P-1 to P-3 is an aryl group, and more preferably a phenyl group, a biphenyl group, a terphenyl group, or a naphthyl group, with a naphthyl group being even more preferable.

$R^{P1}$ to $R^{P3}$ and $R^{'P1}$ to $R^{'P3}$ are preferably either an aryl group or a heteroaryl group, more preferably an aryl group, and even more preferably a phenyl group, a biphenyl group, a terphenyl group, or a naphthyl group, with a phenyl group being most preferable.

$L^{P1}$ to $L^{P3}$ are preferably either a single bond or a divalent linking group composed of an aryl ring, more preferably a single bond, phenylene, biphenylene, terphenylene, or naphthylene, and even more preferably a single bond, phenylene, or naphthylene.

Concrete examples of the compounds expressed by General Formula P are given below, but it should not be construed that the compounds expressed by General Formula P that can be used in the present invention are limited to or by these concrete examples:

[Forty-Fifth Chemical Formula]

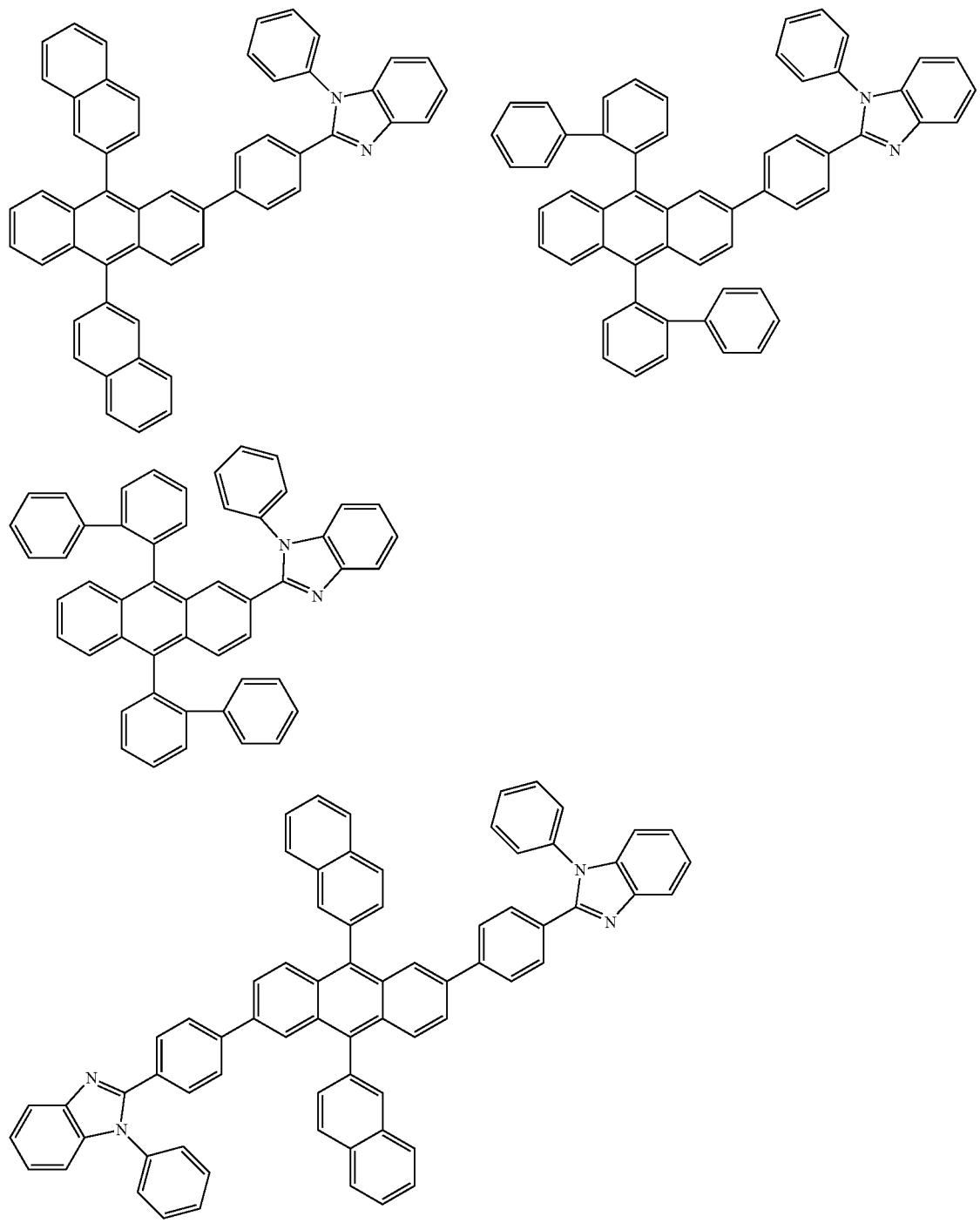

-continued
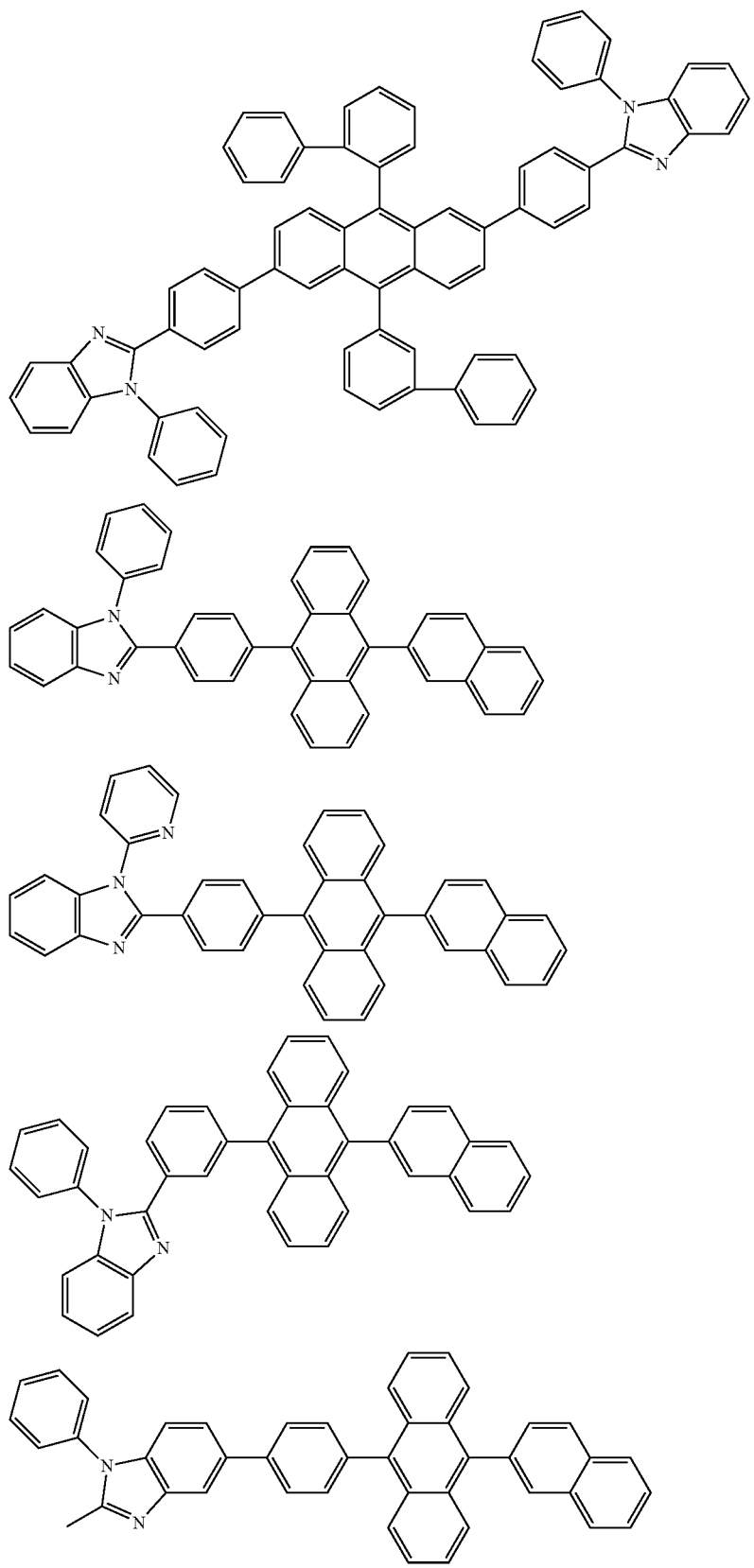

[Forty-Sixth Chemical Formula]

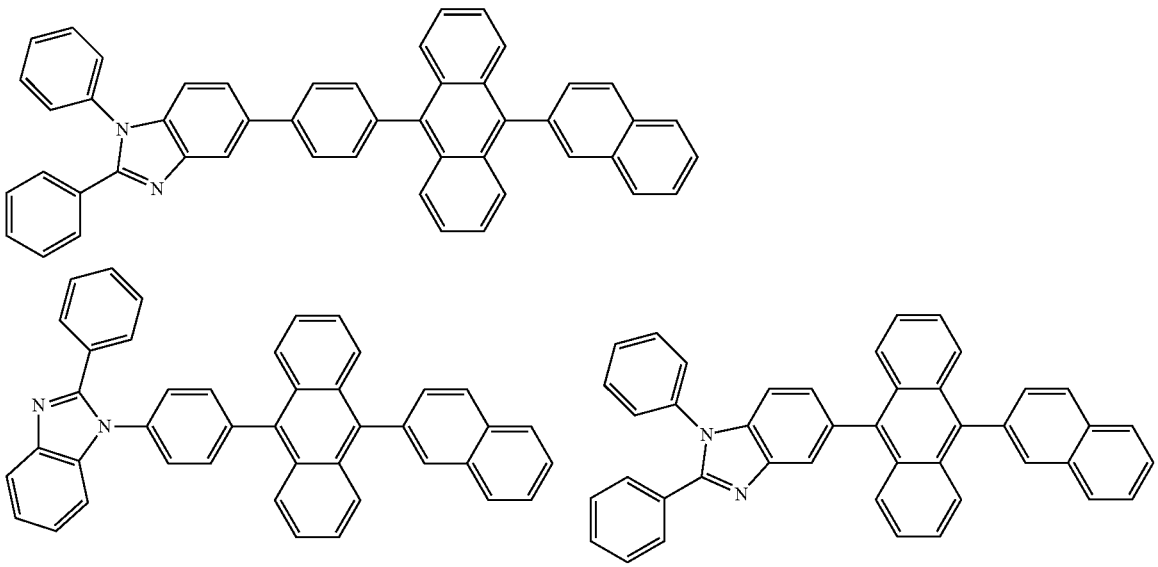

The compounds expressed by General Formula P above can be synthesized by the methods described in WO 2003/060956, WO 2004/080975, and the like. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the organic electroluminescent element of the present invention, the compound expressed by General Formula P is preferably contained in an organic layer between the light-emitting layer and the cathode, but it is more preferably contained in the layer adjacent to the cathode.

The compound expressed by General Formula P is preferably contained in an amount of 70 to 100 wt % and more preferably 85 to 100 wt % with respect to the total weight of the organic layer to which [this compound is] added.

<Protective Layer>

In the present invention, the entire organic electroluminescent element may be protected by a protective layer.

Regarding the protective layer, what is stated in paragraph numbers [0169] and [0170] in Japanese Laid-Open Patent Application 2008-270736 can be applied to the present invention. Note that the material of the protective layer may be either an inorganic material or organic material.

<Sealing Container>

The organic electroluminescent element of the present invention may be entirely sealed by using a sealing container.

Regarding the sealing container, what is stated in paragraph number [0171] in Japanese Laid-Open Patent Application 2008-270736 can be applied to the present invention.

<Drive Method>

The organic electroluminescent element of the present invention can emit light by applying direct current (may include an alternating current component as needed) voltage (usually 2 to 15 volts) or DC current between the anode and the cathode.

For the method for driving the organic electroluminescent element of the present invention, it is possible to apply the drive methods described in the respective Specifications or the like of Japanese Laid-Open Patent Applications H2-148687, H6-301355, H5-29080, H7-134558, H8-234685, and H8-241047, Japanese Patent 2,784,615, and U.S. Pat. Nos. 5,828,429 and 6,023,308.

The external quantum efficiency of the organic electroluminescent element of the present invention is preferably at least 5%, more preferably at least 6%, and even more preferably at least 7%. The numerical value of the external quantum efficiency that can be used is the maximum value for external quantum efficiency when the element is driven at 20° C., or the value for external quantum efficiency near 300 to 400 cd/m$^2$ when the element is driven at 20° C.

The internal quantum efficiency of the organic electroluminescent element of the present invention is preferably at least 30%, more preferably at least 50%, and even more preferably at least 70%. The internal quantum efficiency of the element is calculated by dividing the external quantum efficiency by the light extraction efficiency. The light extraction efficiency is approximately 20% with an ordinary organic EL element, but the light extraction efficiency can be raised to over 20% by modifying the shape of the substrate, the shape of the electrodes, the thickness of the organic layers, the thickness of the inorganic layers, the refractive index of the organic layers, the refractive index of the inorganic layers, and so forth.

<Emission Wavelength>

The emission wavelength of the organic electroluminescent element of the present invention is similar to the maximum emission wavelength of the aforementioned material for an organic electroluminescent element of the present invention. Of the three primary colors of light, it is used for emission of blue light. With the organic electroluminescent element of the present invention, a compound expressed by General Formula 1 above is used as the light-emitting material to cause emission of blue light.

<Applications of the Organic Electroluminescent Element of the Present Invention>

The organic electroluminescent element of the present invention can be utilized favorably in display elements, displays, backlights, electronic photography, illumination light sources, recording light sources, exposure light sources, reading light sources, road signs, trade signs, interior decorating, optical communications, and so forth. [This element] can be especially favorably used in devices that are driven in areas of high light emission brightness, such as in light-emitting devices, illumination devices, and display devices.

Light-Emitting Device

The light-emitting device of the present invention is characterized by including the organic electroluminescent element of the present invention.

Next, the light-emitting device of the present invention will be described with reference to FIG. 2.

The light-emitting device of the present invention makes use of the aforementioned organic electroluminescent element.

Figure 2:
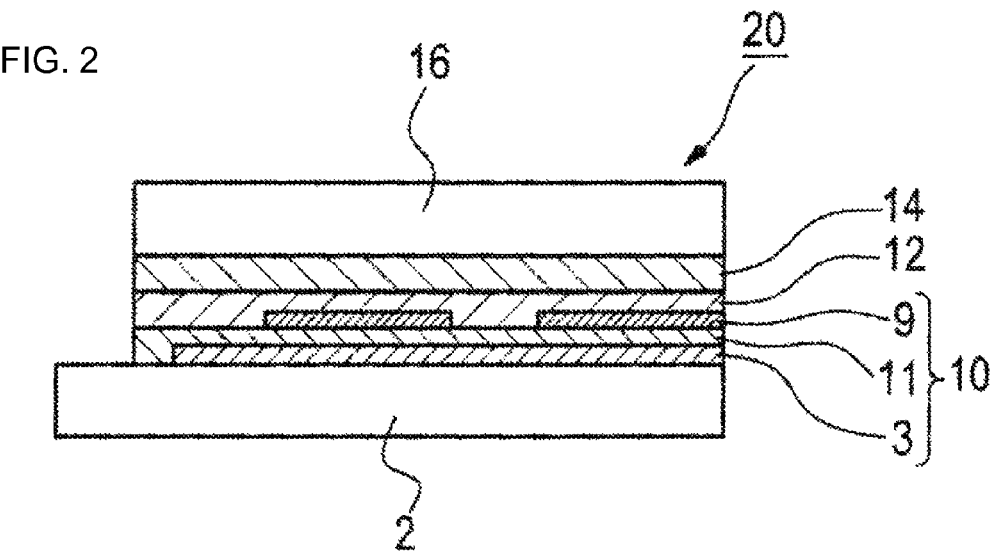
FIG. 2 is a schematic diagram illustrating one example of the light-emitting device according to the present invention.

FIG. 2 is a sectional view schematically showing one example of the light-emitting device of the present invention. The light-emitting device 20 in FIG. 2 is made up of a transparent substrate (support substrate) 2, an organic electroluminescent element 10, a sealing container 16, and the like.

The organic electroluminescent element 10 is configured such that an anode (first electrode) 3, an organic layer 11, and a cathode (second electrode) 9 are sequentially laminated over the substrate 2. Furthermore, a protective layer 12 is laminated over the cathode 9, and in addition, the sealing container 16 is provided on the protective layer 12 via an adhesive layer 14. Note that parts of the electrodes 3 and 9, partitions, insulating layers, and so forth are not depicted.

Here, an epoxy resin or other such photosetting adhesive or thermosetting adhesive can be used as the adhesive layer 14. For example, a thermosetting adhesive sheet can also be used.

There are no particular restrictions on the applications of the light-emitting device of the present invention, but examples other than illumination devices include television sets, personal computers, portable telephones, electronic paper, and other such display devices.

Illumination Device

The illumination device of the present invention is characterized by including the organic electroluminescent element of the present invention.

Next, the illumination device of the present invention will be described with reference to FIG. 3.

Figure 3:
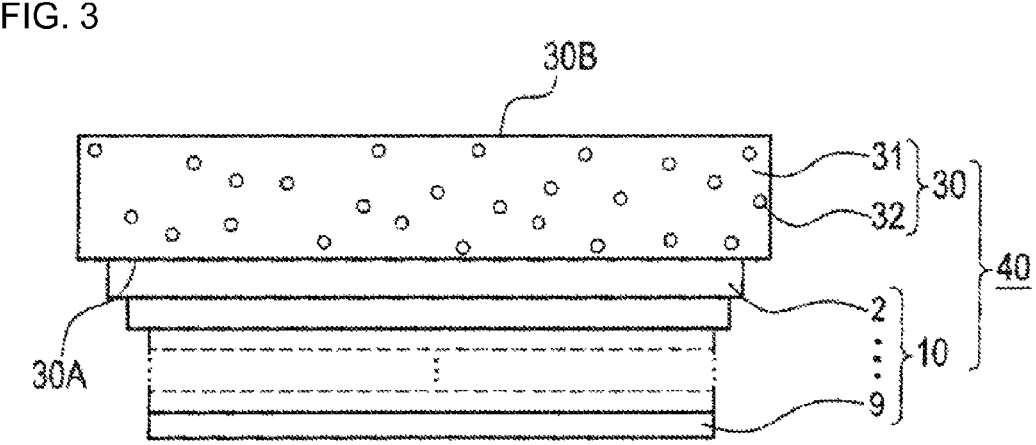
FIG. 3 is a schematic diagram illustrating one example of the illumination device according to the present invention.

FIG. 3 is a sectional view schematically showing one example of the illumination device of the present invention.

As is shown in FIG. 3, the illumination device 40 of the present invention comprises the aforementioned organic EL element 10 and a light-scattering member 30. In more concrete terms, the illumination device 40 is configured such that the substrate 2 of the organic EL element 10 is in contact with the light-scattering member 30.

There are no particular restrictions on the light-scattering member 30 as long as it is capable of scattering light, but in FIG. 3, it is a member in which microparticles 32 are dispersed in a transparent substrate 31. A glass substrate, for example, can be used favorably as the transparent substrate 31. Transparent resin microparticles can be used favorably as the microparticles 32. The glass substrate and the transparent resin microparticles can both be from prior art. This type of illumination device 40 is devised such that when light emitted from the organic electroluminescent element 10 is incident on a light incidence face 30A of the light-scattering member 30, the incident light is scattered by the light-scattering member 30, and the scattered light exits a light emission face 30B as illuminating light.

Display Device

The display device of the present invention is characterized by including the organic electroluminescent element of the present invention.

Examples of the display device of the present invention include television sets, personal computers, portable telephones, electronic paper, and other such display devices.

WORKING EXAMPLES

The characteristic features of the present invention will be described below in more concrete terms by giving working examples and comparative examples. The materials, usage amounts, proportions, processing details, processing procedures, and so forth mentioned in the following working examples can be suitably modified as long as they do not depart from the gist of the present invention. Therefore, it should not be construed that the scope of the present invention is limited to or by the concrete examples given below.

The structural formulas of light-emitting materials 1, 7, 8, and 11 to 17 which are compounds expressed by General Formula 1 used in working examples and the structural formulas of light-emitting materials Ref-1, Ref-2, Ref-11, and Ref-12 used in comparative examples are shown all together below:

[Forty-Seventh Chemical Formula]

1

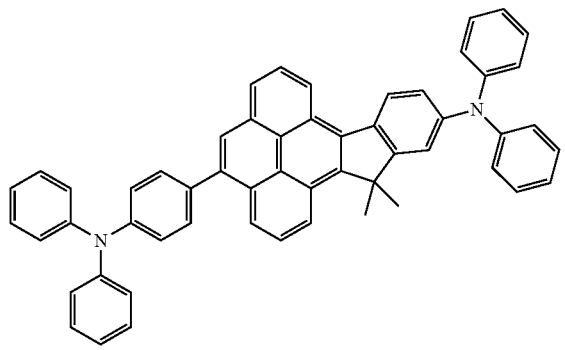

7

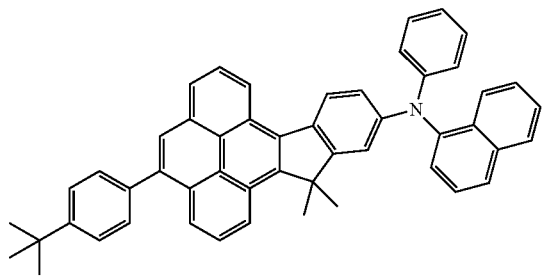

-continued
8
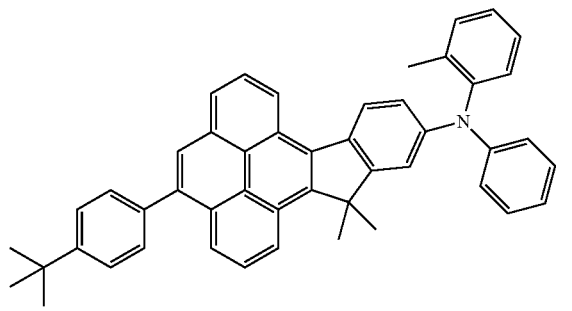
Ref-1
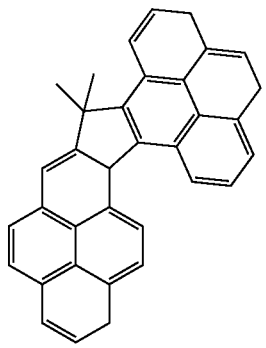
Ref-2
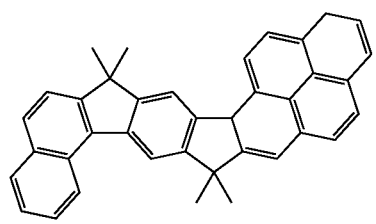
11
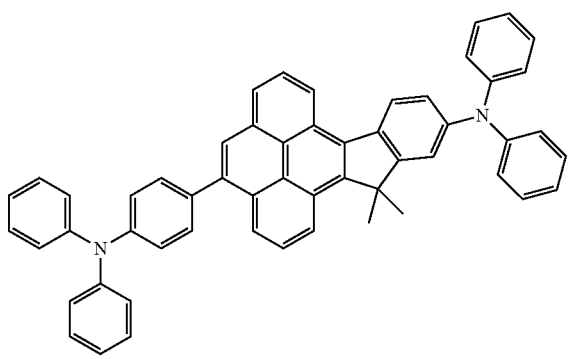
12
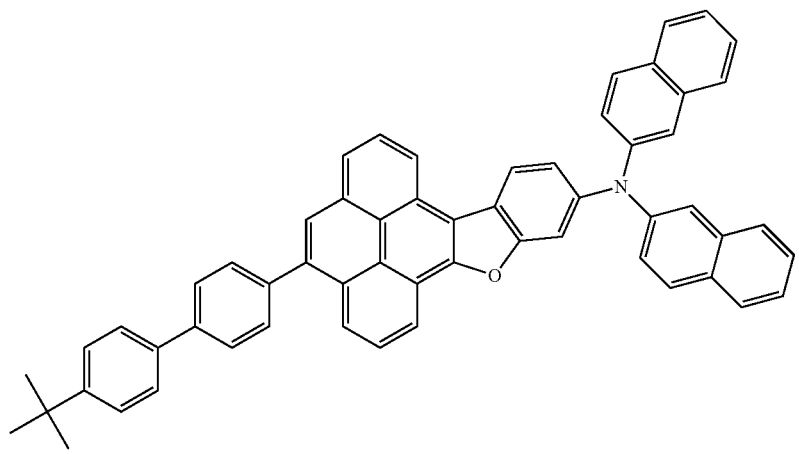
13
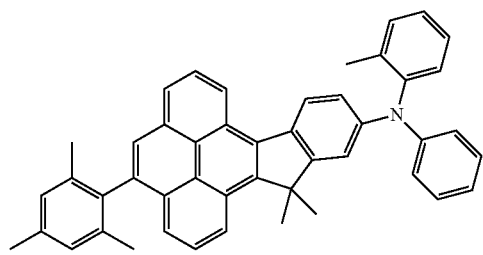
14
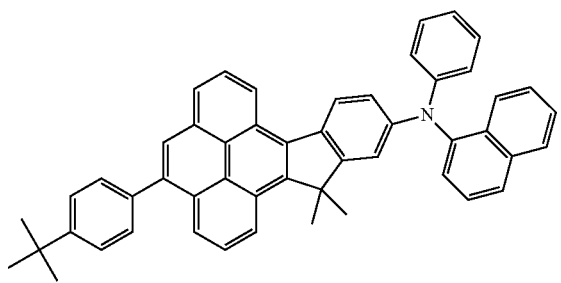

-continued
15
16
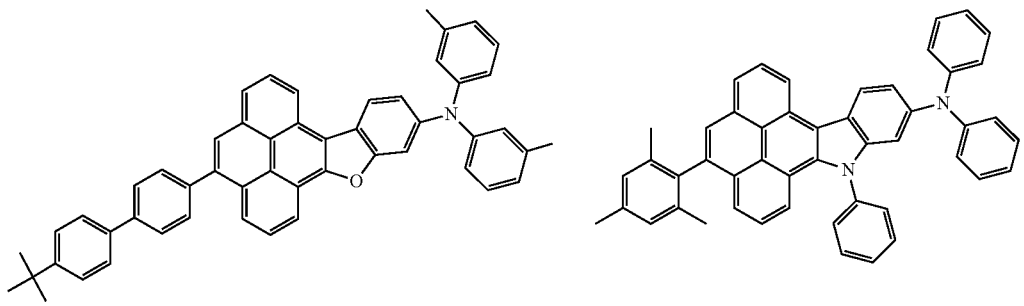
17
Ref-11
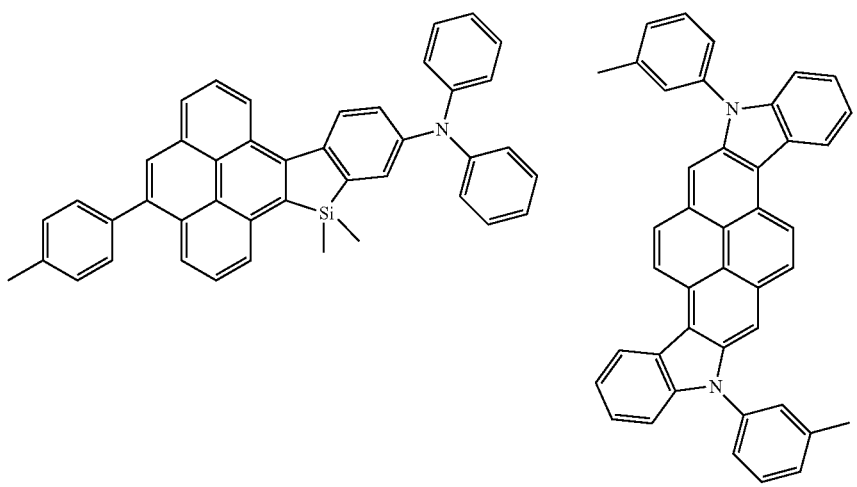
Ref-12
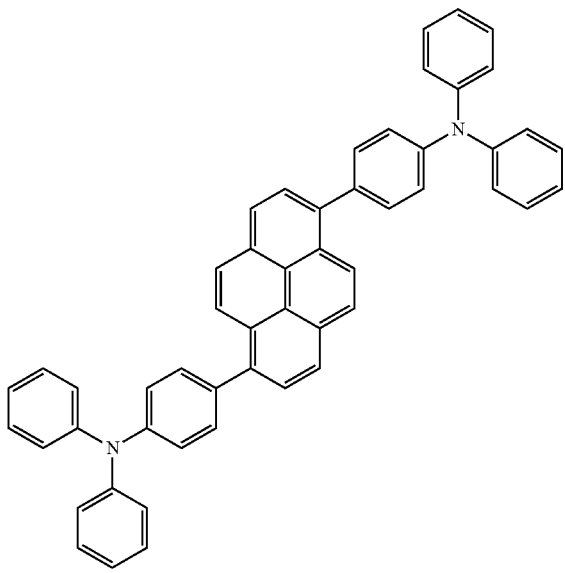

[Forty-Eighth Chemical Formula]
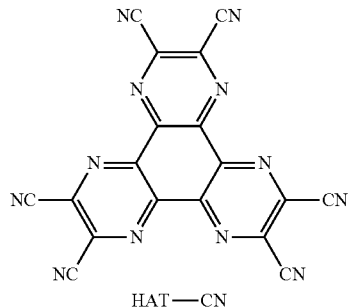
HAT—CN
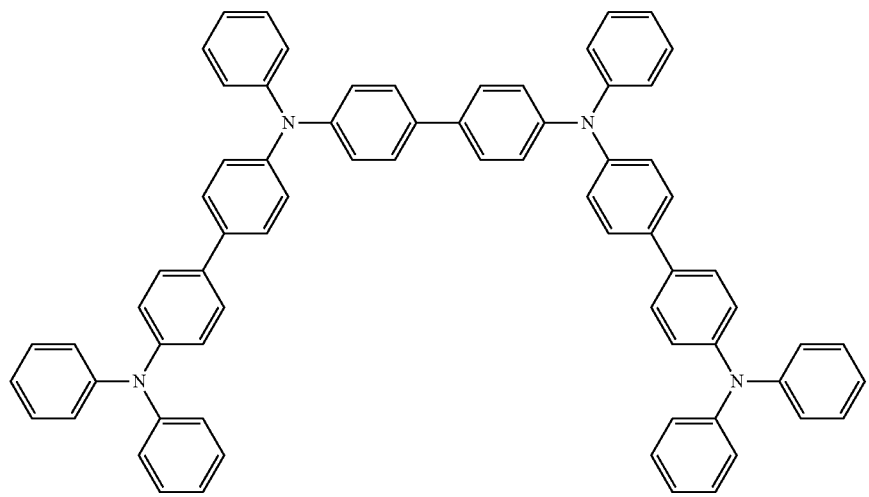
HT-1
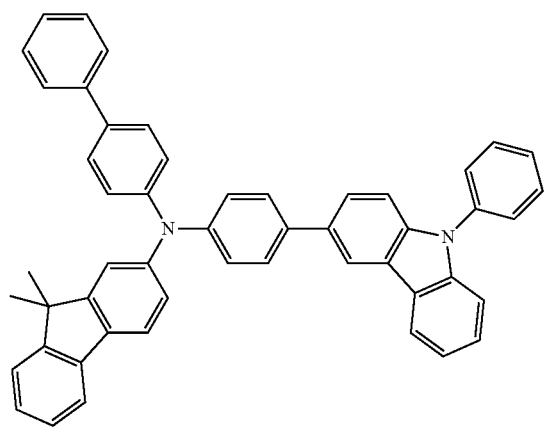
HT-2
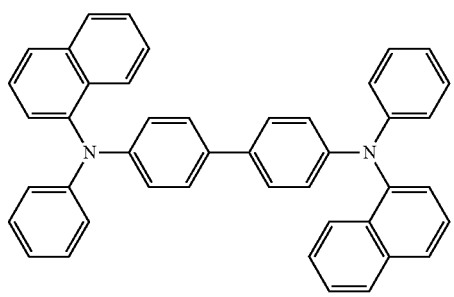
NPD -continued
HT-3
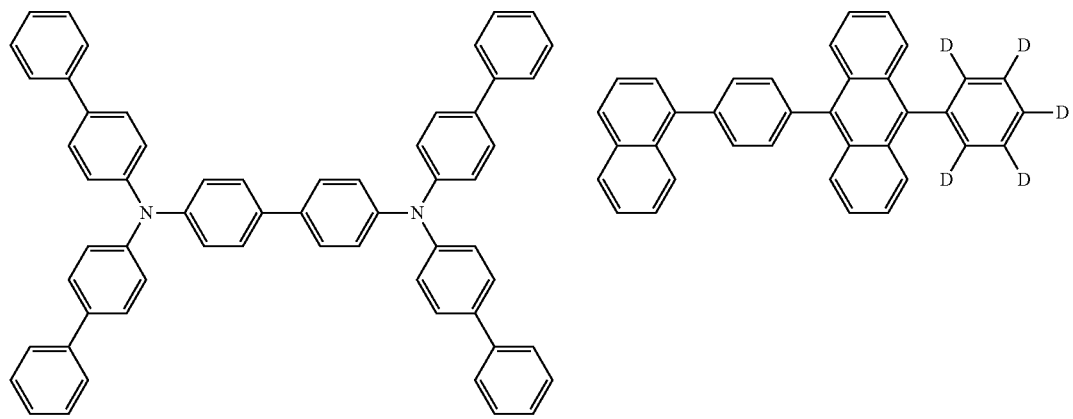
H-1
H-2
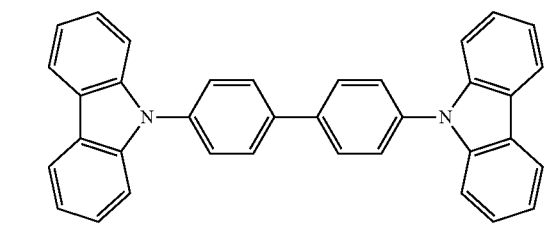
CBP
H-3
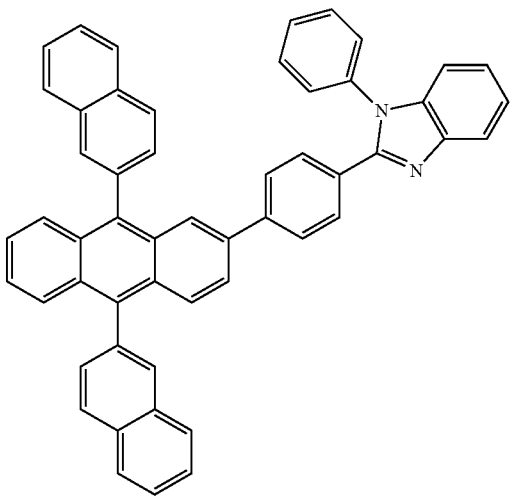
ET-1

-continued

ET-2

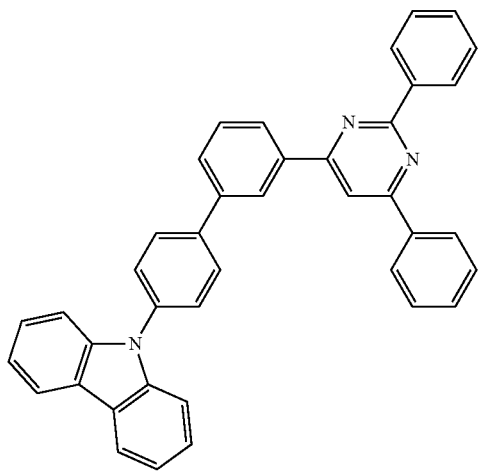

ET-3

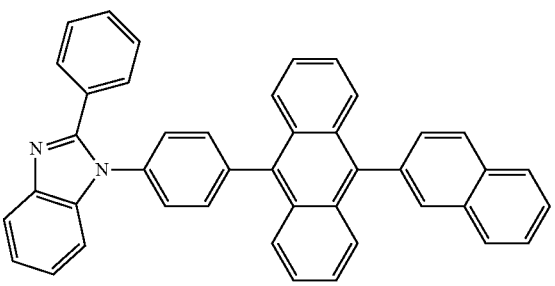

ET-4

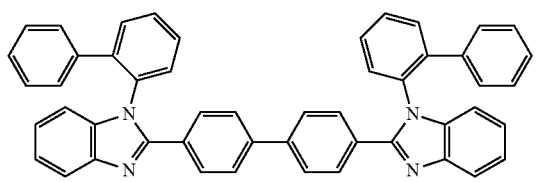

Alq

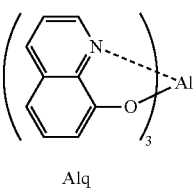

ET-5

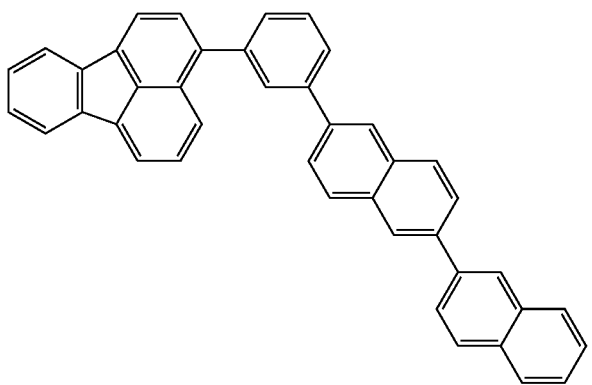

1. Synthesis Examples

The compounds expressed by General Formula 1 can be synthesized by the methods described in this Specification or by a combination of other publicly known reactions. Typical examples of concrete procedures for synthesizing the compounds expressed by General Formula 1 will be described below:

(Synthesis Example 1) Synthesis of Compound 1

[Forty-Ninth Chemical Formula]

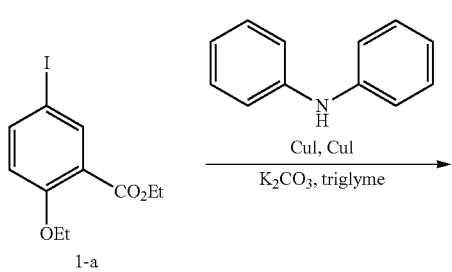

-continued

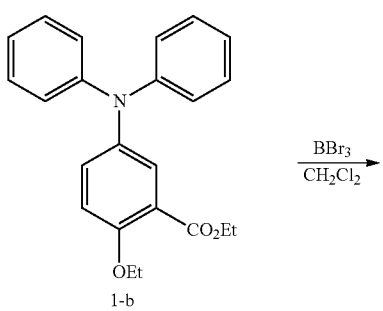

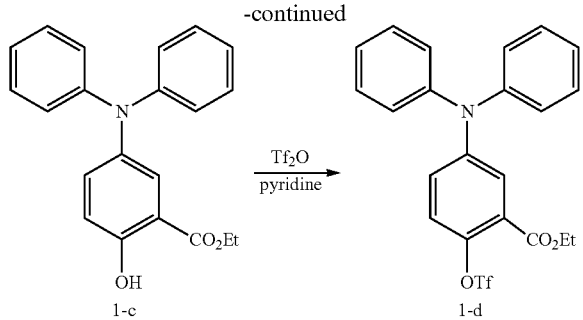

Synthesis of Compound 1-b

Compound 1-a (60.0 g; 187 mmol), diphenylamine (38.06 g; 225 mmol), copper iodide (18 mmol; 3.5 g), copper (37 mmol; 2.4 g), potassium carbonate (374 mmol; 51.7 g), and 180 mL of diphenyl ether were put into a 500-mL three-neck flask, and [the mixture] was heated for 14 hours at 200° C. in a flow of nitrogen gas. The reaction solution was filtered through Celite and, after distilling off the solvent, purified with a silica gel column (hexane eluent). After the solvent was distilled off, the crude powder thus obtained was rinsed with hexane to obtain compound 1-b (amount obtained: 57.0 g; yield: 84.3%) as a white powder.

Synthesis of Compound 1-c

Compound 1-b (57.0 g; 158 mmol) and 400 mL of dichloromethane were added to a 2-L three-neck flask in nitrogen, and a dichloromethane solution of boron tribromide (concentration: 1 mol/L; 205 mL; 205 mmol) was added dropwise over 30 minutes while stirring in an ice bath. Thereafter, the reaction liquid was stirred for 1 hour at room temperature. After the reaction solution was poured into ice water, an organic layer extracted with ethyl acetate was rinsed with an aqueous solution of sodium sulfite. After vacuum distilling off the solvent from the organic layer, it was purified with a silica gel column (hexane eluent:ethyl acetate=9:1). After the solvent was distilled off, rinsing with hexane was performed to obtain compound 1-c (amount obtained: 38.5 g; yield: 73.1%) as a white solid.

Synthesis of Compound 1-d

Compound 1-d [sic][8] (38.5 g; 115 mmol) and 200 mL of pyridine were added to a 1-L three-neck flask in a flow of nitrogen gas, and trifluoromethanesulfonic anhydride (23.6 mL; 140 mmol) was added dropwise over 30 minutes while stirring in an ice bath. Thereafter, [the liquid] was raised to room temperature and stirred for 6 hours. 700 mL of water was added to the reaction solution in an ice bath, and when the solids thus obtained were filtered and rinsed with water, compound 1-d (52.6 g; ~100%) was obtained.

[8] Translator's note: "Compound 1-d" is probably an error in the original for "Compound 1-c."

[Fiftieth Chemical Formula]

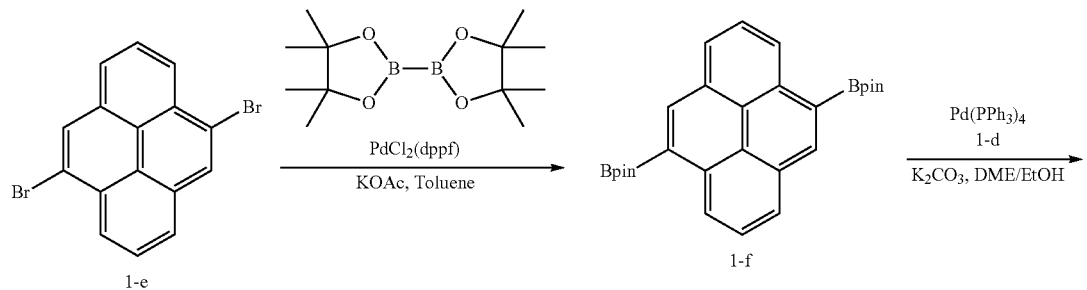

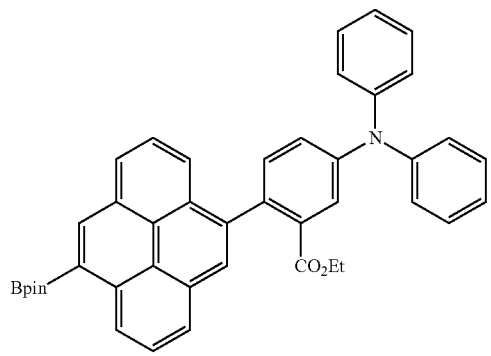

-continued
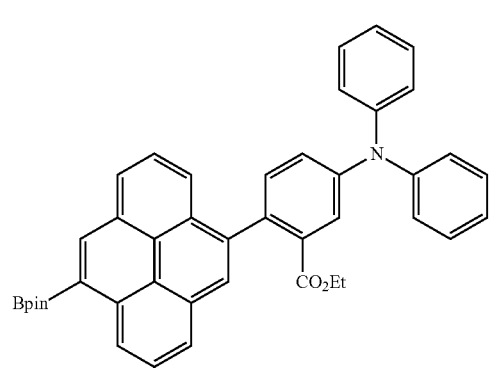
1-g
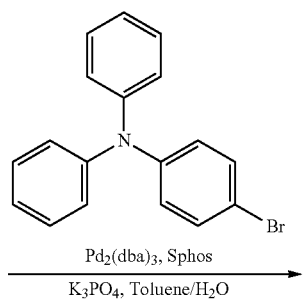
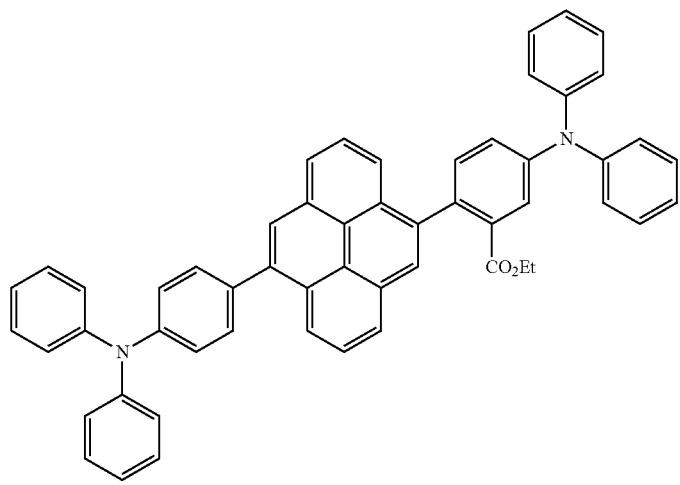
1-h
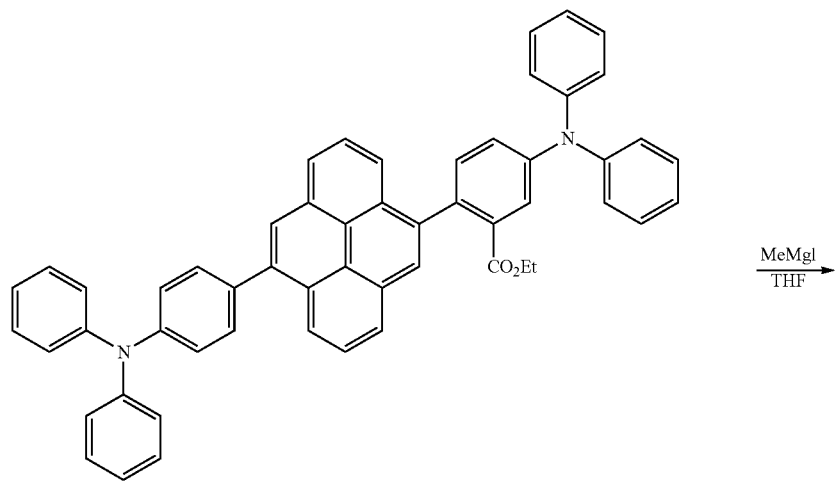
1-h

-continued
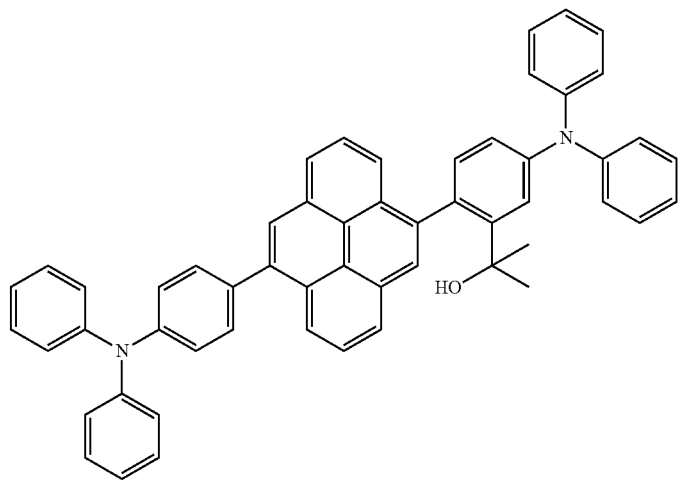
1-i
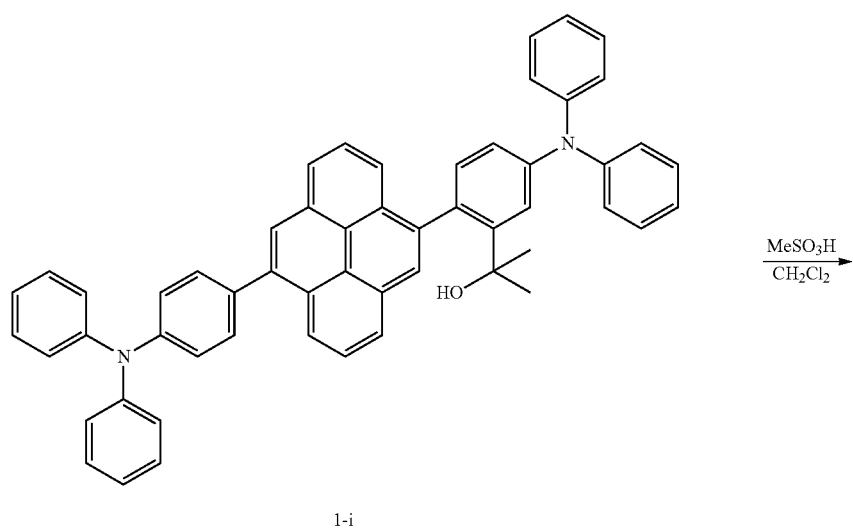
1-i
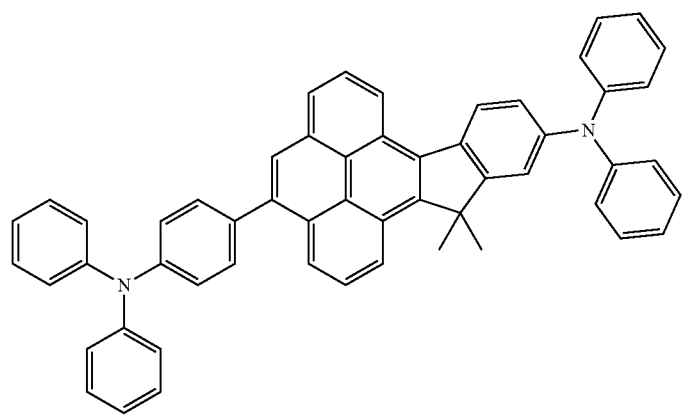
1

Compound 1-e was synthesized according to the method recited in the literature (Synthesis, May 1989, page 356 et seq.).

Synthesis of Compound 1-f

Compound 1-e (9.0 g; 24.6 mmol), bis(pinacolato)diboron (13.7 g; 54.1 mmol), potassium acetate (7.2 g; 73.8 mmol), (diphenylphosphino ferrocene)palladium dichloride (1.0 g; 1.2 mmol), and 90 mL of toluene were heated and stirred for 13 hours at 80° C. in a flow of nitrogen gas, and the reaction solution was extracted with ethyl acetate. After distilling off the solvent, Celite filtration followed by silica gel filtration were performed, and after distilling off the solvent, ethanol was added, and the white solid thus obtained was filtered to obtain compound 1-f.

Synthesis of Compound 1-g

Compound 1-f (6.75 g; 14.7 mmol), compound 1-d (8.2 g; 17.6 mmol), potassium carbonate (4.8 g; 35.2 mmol), tetrakis(triphenylphosphine)palladium (1.0 g; 0.9 mmol), 200 mL of dimethoxyethane, and 170 mL of ethanol were heated in a 1-L three-neck flask at 110° C. in a flow of nitrogen gas; the reaction solution thus obtained after distilling off the solvent was purified with a silica gel column (hexane eluent:ethyl acetate=9:1) to obtain compound 1-g.

Synthesis of Compound 1-h

Compound 1-g (1.73 g; 2.7 mmol), N-p-bromophenyl-diphenylamine (1.0 g; 3.2 mmol), 2-dicyclohexylphosphino-2',6'-dimethoxybiphenyl (0.16 g; 0.38 mmol), tripotassium phosphate (3.4 g; 1.6 mmol), tris(dibenzylideneacetone)dipalladium (88 mg; 0.1 mmol), 20 mL of toluene, and 10 mL of water were added to a 200-mL two-neck flask, and [the mixture] was heated for 3 hours at 100° C. in a flow of nitrogen gas. After allowing the reaction solution to cool, an organic layer was extracted with toluene, and the organic layer was rinsed with an aqueous solution of sodium chloride. The residue obtained after distilling off the solvent was purified with a silica gel column (hexane eluent:ethyl acetate=9:1) to obtain compound 1-h.

Synthesis of Compound 1-i

Compound 1-h (2.4 g; 3.1 mmol) and 24 mL of THF were added to a 100-mL round-bottomed flask and dissolved in an ice bath, and methylmagnesium iodide (12.5 mmol) was added dropwise in a flow of nitrogen gas. Thereafter, the reaction solution was raised to room temperature and then heated to 80° C. and heated for 3 hours. After the reaction solution was neutralized with a 1M aqueous solution of ammonium chloride, an organic layer was extracted with ethyl acetate. The organic layer was rinsed with an aqueous solution of sodium chloride, and the residue after distilling off the solvent was purified with a silica gel column (hexane eluent:ethyl acetate=9:1) to obtain compound 1-i.

Synthesis of Compound 1

Compound 1-i (1.8 g; 2.4 mmol) and 60 mL of dichloromethane were added to a 200-mL three-neck flask, and the reaction solution was cooled to −75° C. Thereafter, methanesulfonic acid (46 mg; 0.48 mmol) was added dropwise, and [the reaction solution] was then raised to room temperature. The reaction solution was poured into water and extracted with ethyl acetate, and the residue obtained after distilling off the solvent was purified with a column to obtain compound 1.

Figure 6:
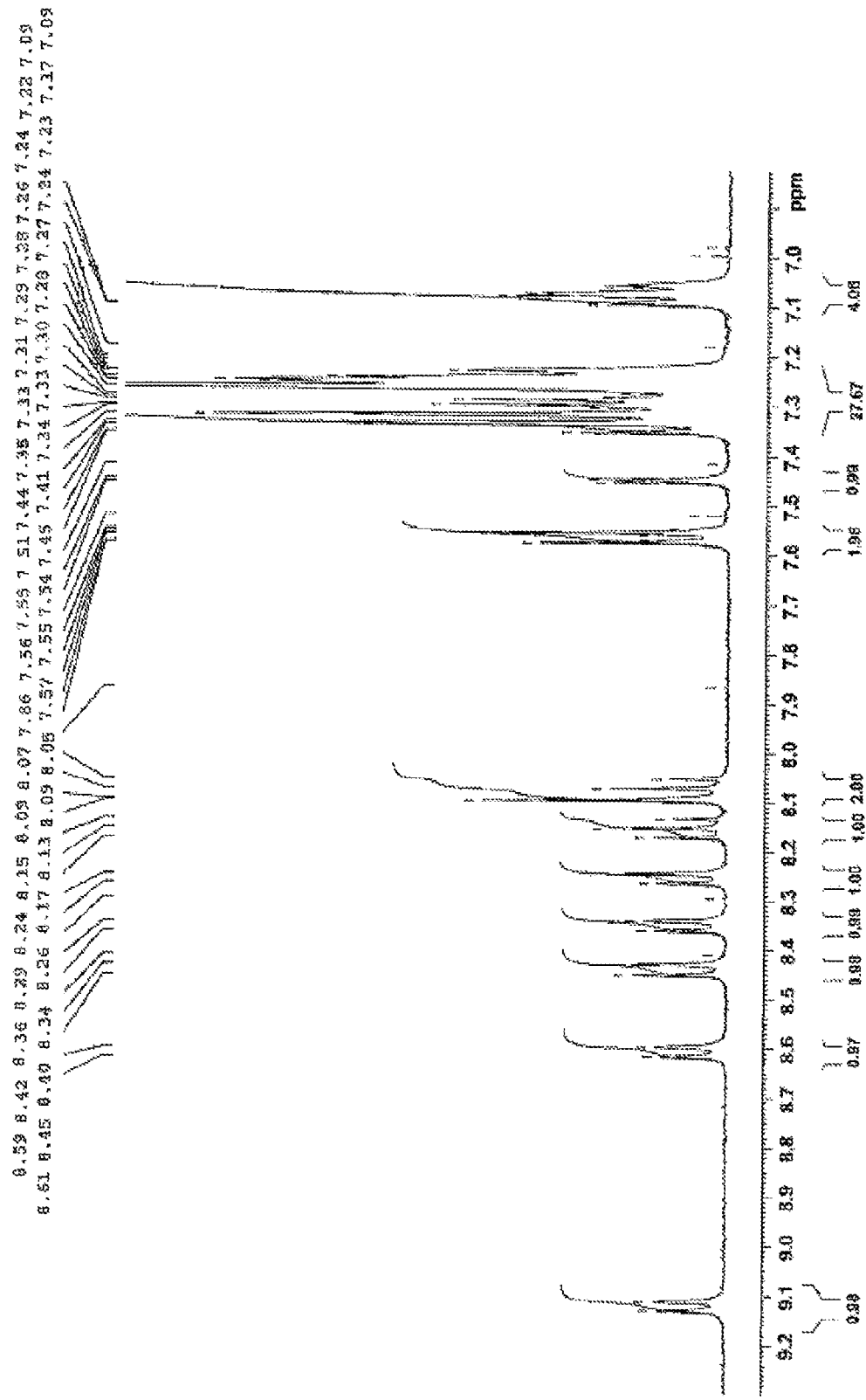
FIG. 6 is an enlarged diagram of one portion the NMR chart of the compound illustrated in FIG. 5.

FIG. 5 illustrates the NMR chart for compound 1. In addition, FIG. 6 illustrates a partial enlargement of the NMR chart of FIG. 5.

Furthermore, instead of reacting compound 1-a with diphenylamine, it is possible to react it with various di-substituted amines in the same manner to synthesize the intermediate 1-d and its analogues 1-d' and 1-d".

[Fifty-First Chemical Formula]

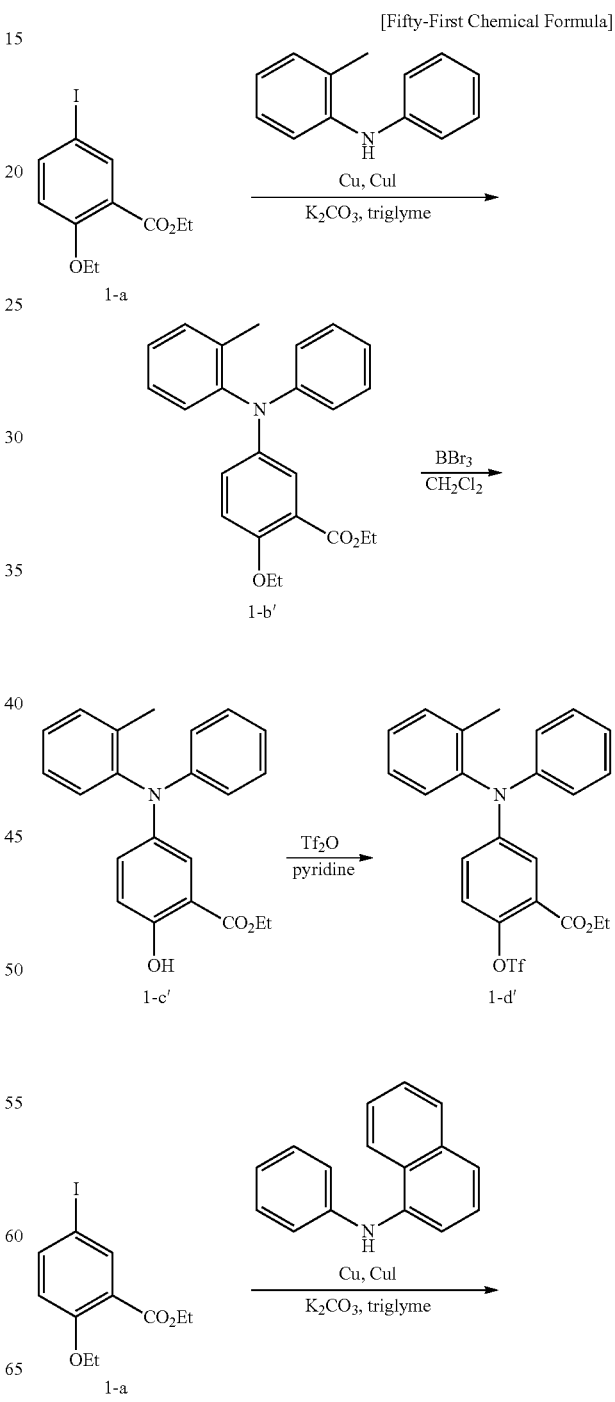

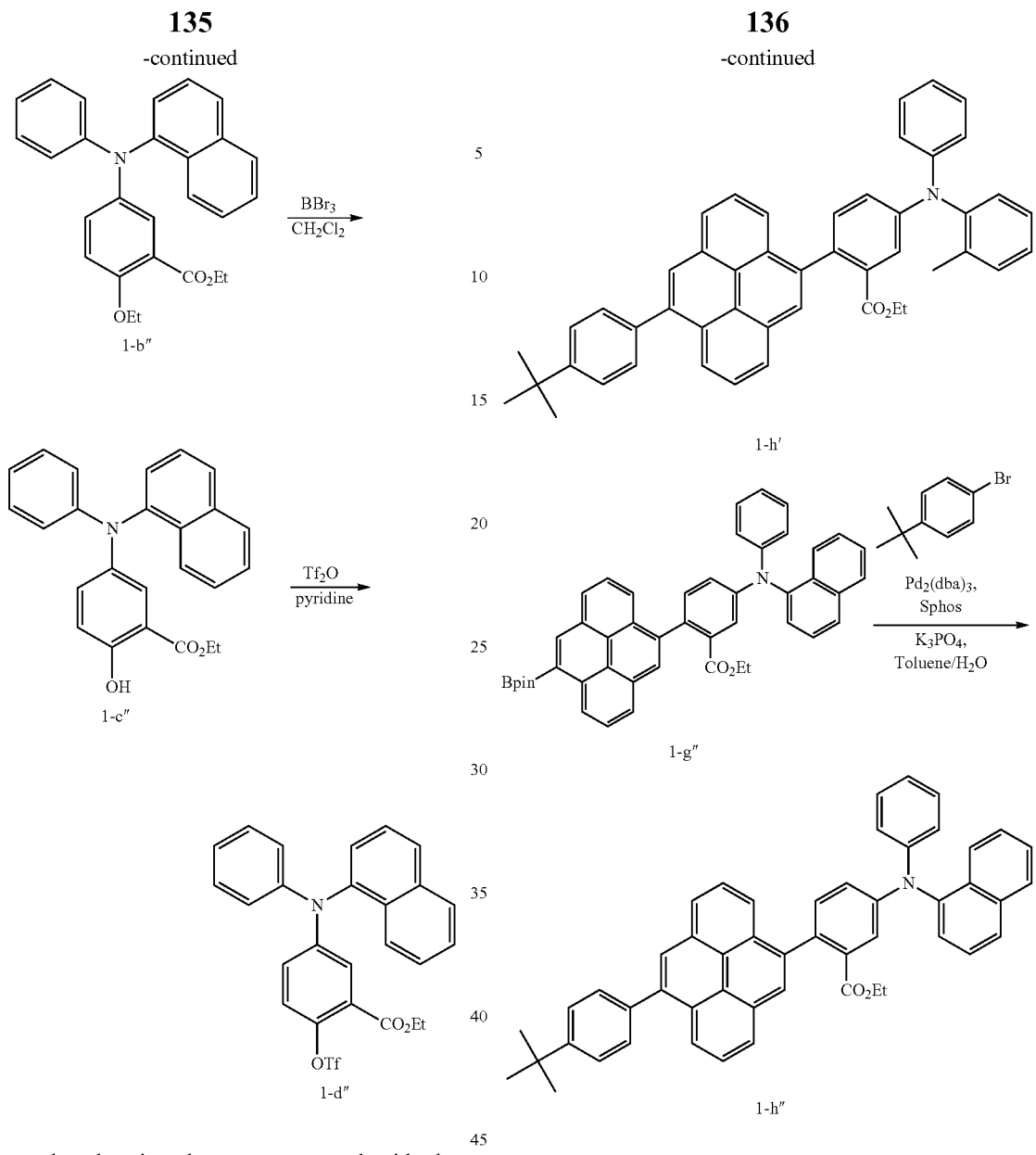

Moreover, by changing the reagent reacted with the analogues 1-g' and 1-g" of compound 1-g in the aforementioned scheme from N-p-bromophenyl-diphenylamine to p-bromo-t-butylbenzene, it is possible to synthesize analogues 1-h' and 1-h" of intermediate 1-h.

Based on the aforementioned synthesis method, it is possible to synthesize compounds 7 and 8 from 1-h' and 1-h".

[Fifty-Second Chemical Formula]

[Fifty-Third Chemical Formula]

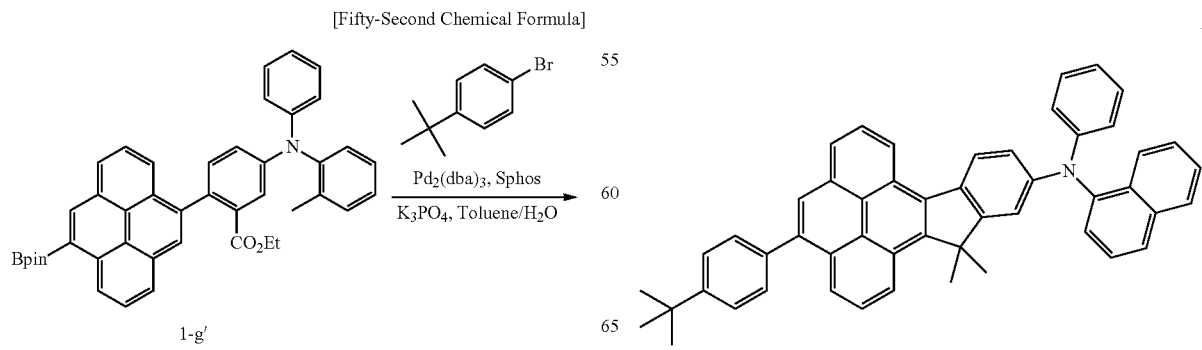

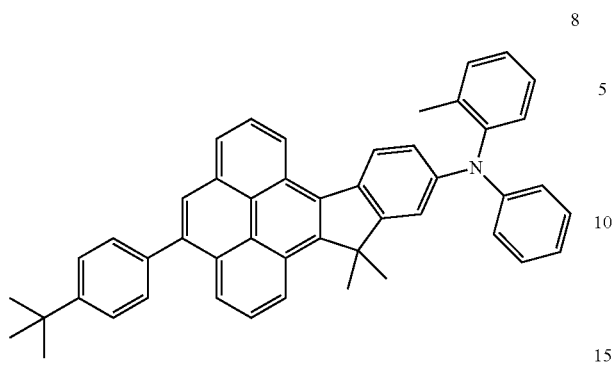
(Synthesis Example 2) Synthesis of Compound 12
[Fifty-Fourth Chemical Formula]
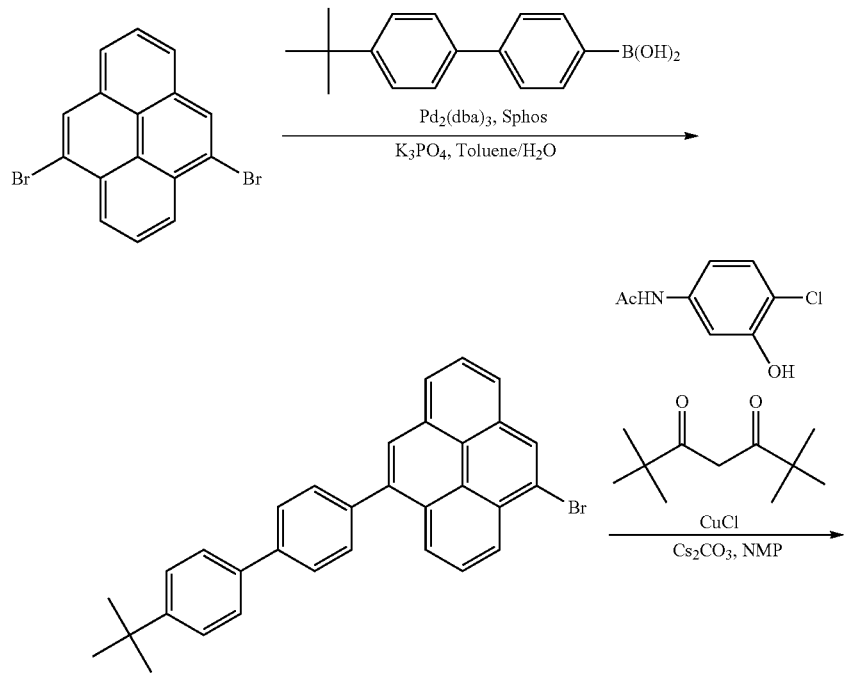
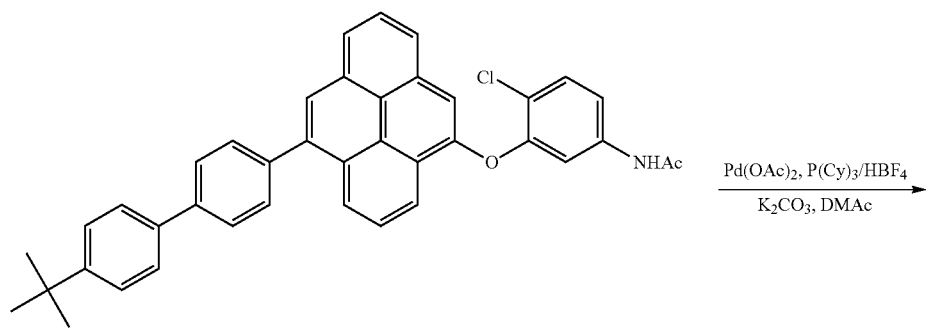

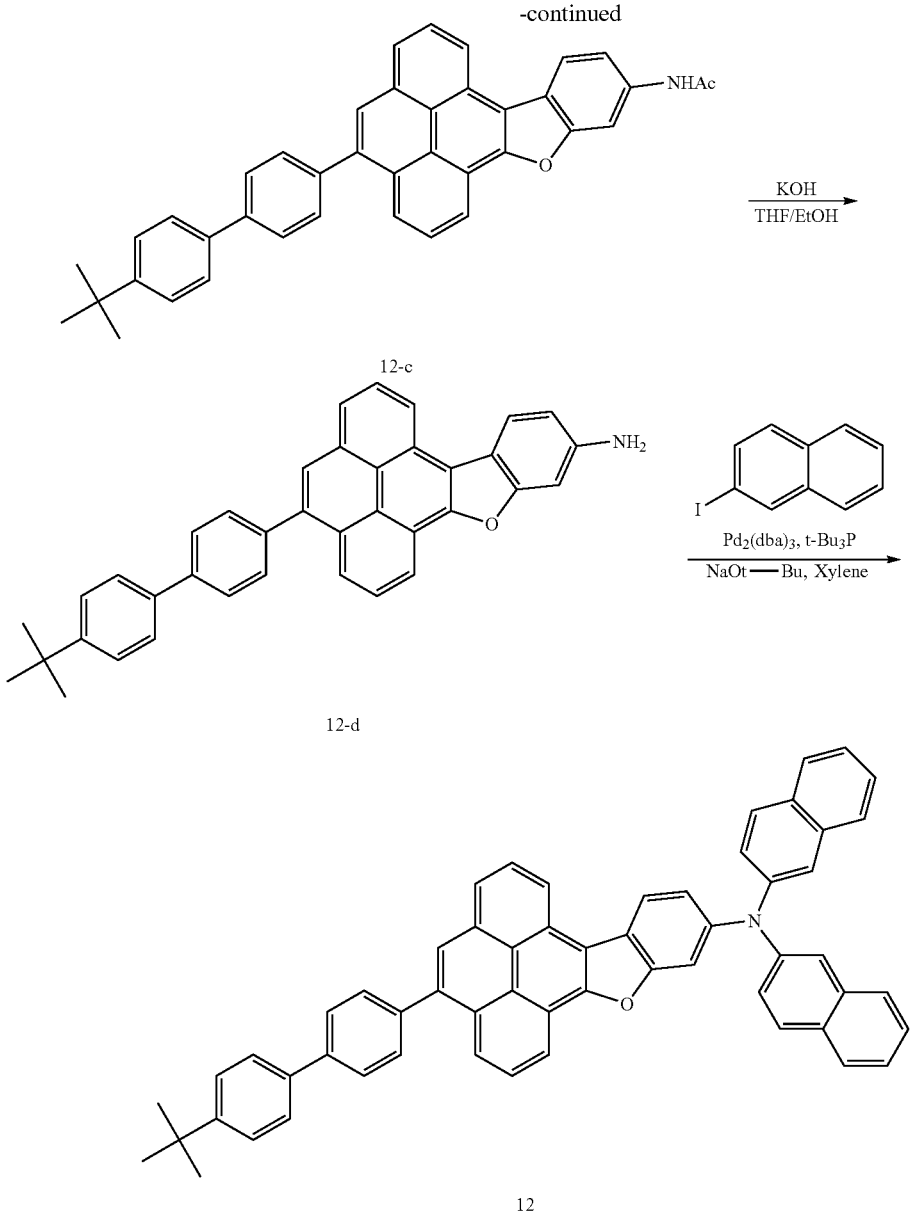

Synthesis of Compound 12-a 4,10-dibromopyrene (20.55 g; 57.09 mmol), 4-(4-tertiary-butylphenyl)phenylboronic acid (14.51 g; 57.09 mmol), 2-dicyclohexylphosphino-2',6'-dimethoxybiphenyl (5.62 g; 0.14 mmol), tripotassium phosphate (60.59 g; 285 mmol), tris(dibenzylideneacetone)dipalladium (2.61 g; 2.9 mmol), 600 mL of toluene, and 300 mL of water were added, and [the mixture] was heated for 3 hours at 100° C. in a flow of nitrogen gas. After allowing the reaction solution to cool, an organic layer was extracted with toluene, and the organic layer was rinsed with an aqueous solution of sodium chloride. The residue obtained after distilling off the solvent was purified with a silica gel column (hexane eluent: ethyl acetate=9:1) to obtain compound 12-a.

Synthesis of Compound 12-b

Compound 12-a (15.62 g; 31.91 mmol), N-(4-chloro-3-hydroxyphenyl)acetamide (7.11 g; 38.30 mmol), dipivaloyl-methane (1.18 g; 6.38 mmol), cesium carbonate (51.98 g; 160 mmol), copper(I) chloride (6.32 g; 63.82 mmol), and 300 mL of N-methylpyrrolidone were added to a 1-L three-neck flask, and [the mixture] was stirred for 9 hours at 130° C. in a flow of nitrogen gas. After allowing [the reaction solution] to cool, the organic salts within the reaction solution were filtered with Celite and liquid-separated with pure water/toluene. The residue obtained after distilling off the solvent was purified with a silica gel column (hexane eluent:ethyl acetate=2:1) to obtain compound 12-b.

Synthesis of Compound 12-c

Compound 12-b (3.46 g; 5.83 mmol), potassium carbonate (3.22 g; 23.33 mmol), tricyclohexylphosphine tetrafluoroborate (1.72 g; 4.67 mmol), palladium acetate (0.52 g; 2.33 mmol), and 35 mL of dimethylacetamide were added to a 200-mL three-neck flask, and [the mixture] was stirred for 2 hours at 130° C. in a flow of nitrogen gas. The reaction solution was allowed to cool and then poured into water. The precipitated solids were filtered, and purification by recrystallization in THF was repeated to obtain compound 12-c.

Synthesis of Compound 12-d

Compound 12-c (1.60 g; 2.87 mmol), potassium hydroxide (1.29 g; 22.95 mmol), 300 mL of tetrahydrofuran, 50 mL of ethanol, and 5 mL of pure water were added to a 200-mL three-neck flask, and [the mixture] was refluxed for 10 hours in a flow of nitrogen gas. The reaction solution was allowed to cool and then extracted with ethyl acetate, and the residue obtained after distilling off the solvent was purified with a silica gel column (hexane elute:ethyl acetate=9:1) to obtain compound 12-d.

Synthesis of Compound 12

Figure 7:
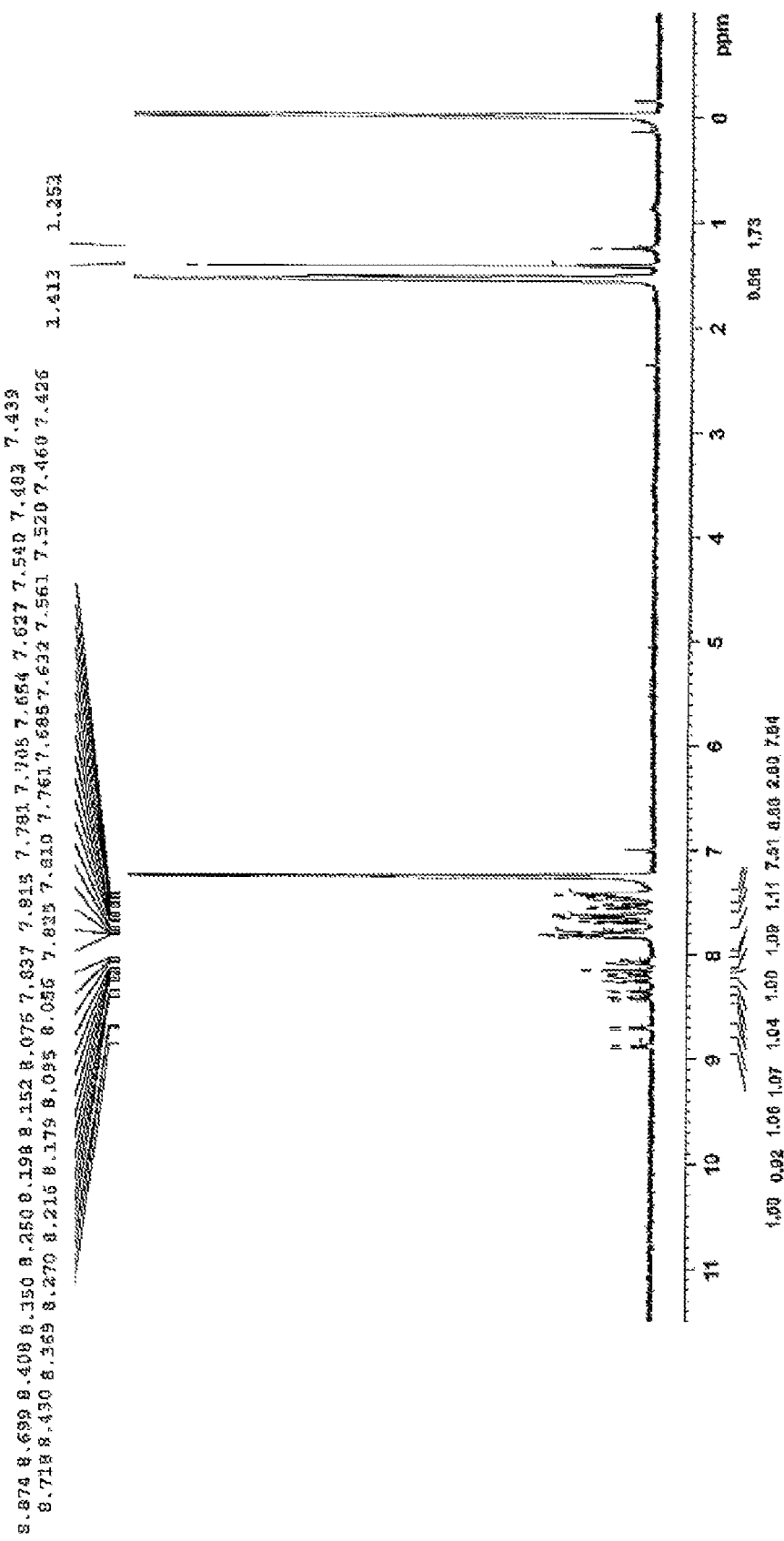
FIG. 7 is a diagram showing an NMR chart of another compound used in the light-emitting material for use in the organic electroluminescent element of the present invention.

Compound 12-d (1.40 g; 2.72 mmol), 2-iodonaphthalene (2.07 g; 8.15 mmol), sodium tertiary-butoxide (0.86 g; 8.96 mmol), tris(dibenzylideneacetone)dipalladium (0.25 g; 0.27 mmol), tritertiary-butylphosphine (55 mg; 0.27 mmol), and 55 mL of xylene were added to a 200-mL three-neck flask, and [the mixture] was refluxed for 4 hours in a flow of nitrogen gas. After allowing the reaction solution to cool, it was extracted with toluene, and the residue obtained after distilling off the solvent was purified with a silica gel column (hexane eluent:toluene=1:1) to obtain compound 12. FIG. 7 illustrates the NMR chart of compound 12 (in CDCl$_3$).

2. Production and Evaluation of Organic Electroluminescent Elements

<Confirmation of Purity>

All the materials used in the production of the organic electroluminescent elements were subjected to sublimation purification, and it was confirmed by high-performance liquid chromatography (Tosoh TSK gel ODS-100Z) that the purity (absorption intensity surface area ratio at 254 nm) was 99.9% or higher.

Working Example 1

Production of Organic Electroluminescent Elements by Vapor Deposition

A glass substrate (made by Geomatec Co., surface resistance of 10 ohms/square) having an ITO film measuring 2.5 cm$^2$ and 0.5 mm thick was put into a washing vessel and ultrasonically washed in 2-propanol, upon which it was subjected to treatment with UV-ozone for 30 minutes. The following organic compound layers were sequentially deposited onto this transparent anode (ITO film) by a vacuum vapor deposition method:

First layer: HAT-CN; film thickness of 10 nm
Second layer: NPD; film thickness of 30 nm
Third layer: H-1 and the light-emitting material listed in Table 1 (weight ratio of 93:7); film thickness of 30 nm
Fourth layer: BAlq; film thickness of 30 nm HAT-CN is the following structure:

[Fifty-Fifth Chemical Formula]

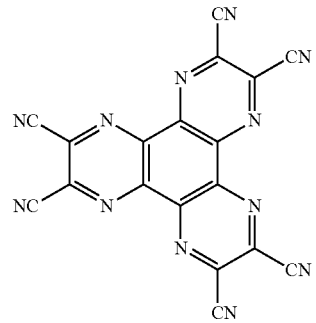

NPD is the following structure:

[Fifty-Sixth Chemical Formula]

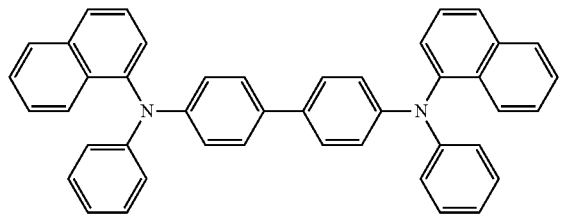

H-1 is the following structure:

[Fifty-Seventh Chemical Formula]

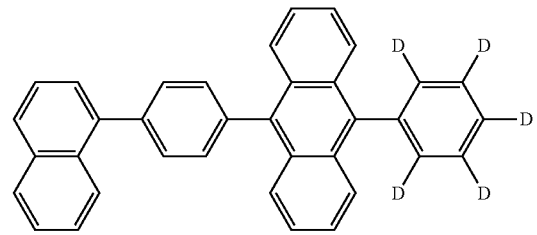

BAlq is bis-(2-methyl-8-quinolinolato)-4-(phenyl-phenolato)-aluminum(III) in the following structure:

[Fifty-Eighth Chemical Formula]

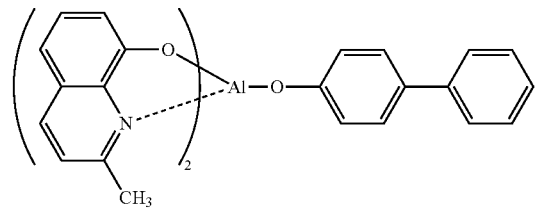

Over this, lithium fluoride (1 nm) and metallic aluminum (100 nm) were vapor-deposited in this order to form a cathode. Note that a patterned mask (a mask in which the emission region measured 2 mm×2 mm) was installed over the lithium fluoride layer, and metallic aluminum was vapor-deposited.

Without being allowed to come into contact with the air, this obtained laminate was placed in a glove box that had been replaced with nitrogen gas, and was sealed using a glass sealing jar and a UV-setting adhesive (XNR5516HV, made by Nagase Chiba), which gave organic electroluminescent elements 1 to 6 of the present invention and comparative elements 1 and 2. These elements were caused to emit light, which resulted in light emission originating in the light-emitting material for each of the elements.

The various organic electroluminescent elements thus obtained were tested as follows:

<Evaluation of Elements>

(a) External Quantum Efficiency

Using a source measurement unit 2400 made by Keithley, DC voltage was applied to each element to make it emit light, and the brightness thereof was measured using a brightness meter (BM-8 made by Topcon). The emission spectrum and the emission wavelength were measured using a spectral analyzer (PMA-11 made by Hamamatsu Photonics). Based on these results, the external quantum efficiency (η) when the brightness was close to 1000 cd/m² was calculated by brightness conversion method, and the relative external quantum efficiency was expressed in Table 1 below as a relative value when the external quantum efficiency of the organic electroluminescent element in which Ref-2 was used is 1.0. Larger numbers indicate higher efficiency and are therefore preferable.

(b) Chromaticity

The chromaticity (x, y) (in the CIE 1931 color space) was found from the emission spectrum when DC voltage was applied to make each organic electroluminescent element emit light so as to obtain a brightness of 1000 cd/m². Taking the most superior blue (0.14, 0.08) to be the reference point 0, the distance in chromaticity of each of the organic electroluminescent elements from the reference point 0 was calculated upon the CIE chromaticity coordinate plane and evaluated on the following basis. The results thereof are shown in Table 1 below.

○: Those <0.02
Δ: Those ≥0.02 and <0.035
x: Those ≥0.035

(c) Change in Chromaticity During Brightness Modulation

DC voltage was applied to make each organic electroluminescent element emit light continuously such that the brightness would be 1000 cd/m², and the chromaticity (x', y') at the point when the brightness decreased to 500 cd/m² was found from the emission spectrum. The change in chromaticity after drive deterioration was evaluated in the following three levels from the change Δy in the y value before and after drive deterioration (=|y'×Δy|):

○: Δy≤0.01
Δ: 0.01<Δy≤0.02
x: 0.02<Δy chromaticity during brightness modulation. In addition, it was also found that the relative external quantum efficiency was excellent.

Working Example 2

Preparation of Coating Solution for Forming Light-Emitting Layer

Toluene (94.75 wt %) was mixed with the light-emitting material 1 (0.25 wt %) and a host material ADN (5 wt %), which gave a light-emitting layer formation coating solution 1.

Other than changing the light-emitting material 1 in the light-emitting layer formation coating solution 1 to the light-emitting materials 3 and 6, light-emitting layer formation coating solutions 2 and 3 were prepared in the same manner as the light-emitting layer formation coating solution 1.

ADN represents 9,10-(di-2-naphthyl) anthracene with the following structure:

[Fifty-Ninth Chemical Formula]

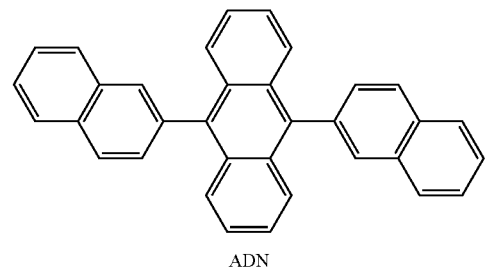

ADN

—Production of Organic Electroluminescent Element—

A transparent support substrate was produced by forming a film of ITO in a thickness of 150 nm by vapor deposition over a glass substrate measuring 25×25×0.7 mm. This transparent support substrate was etched and washed.

2 parts by weight of PTPDES-2 (made by Chemipro Kasei; Tg=205° C.) expressed by the following structural formula was dissolved in 98 parts by weight of commercial grade (electronics) cyclohexanone (made by Kanto Chemical), and [this product] was applied over the ITO glass substrate by spin coating (2000 rpm for 20 seconds) such that the thickness would be approximately 40 nm, upon

TABLE 1

|  | Light-emitting material | Relative external quantum efficiency | Chromaticity | Change in chromaticity during brightness modulation |
|---|---|---|---|---|
| Organic electroluminescent element 1 of the present invention | Compound 1 | 1.6 | Δ | ○ |
| Organic electroluminescent element 7 of the present invention | Compound 7 | 1.5 | ○ | ○ |
| Organic electroluminescent element 8 of the present invention | Compound 8 | 1.4 | Δ | ○ |
| Comparative element 1 | Compound Ref-1 | 0.6 | Δ | x |
| Comparative element 2 | Compound Ref-2 | 1.0 | Δ | x |

It was revealed from Table 1 above that the organic electroluminescent elements of the present invention emitted dark blue light and that there was little change in which [the coating] was dried for 30 minutes at 120° C. and annealed for 10 minutes at 160° C., thereby forming a hole injection layer.

[Sixtieth Chemical Formula]

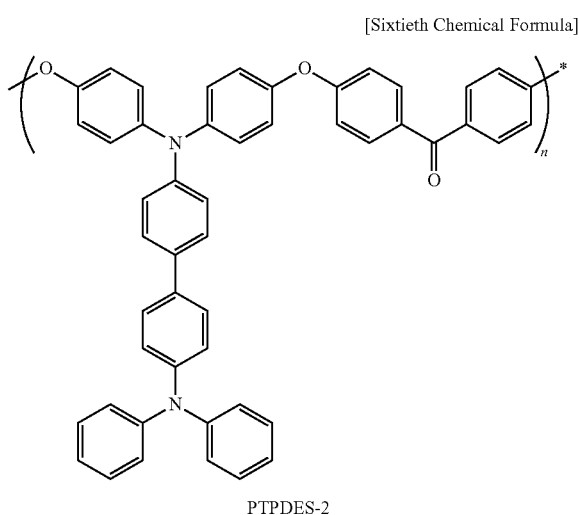

PTPDES-2

The aforementioned light-emitting layer formation coating solutions 1 to 6 were applied over this hole injection layer by spin coating (1300 rpm for 30 seconds) such that the thickness would be approximately 40 nm, thereby forming a light-emitting layer.

Then, over the light-emitting layer, BAlq (bis-(2-methyl-8-quinolinolato)-4-(phenyl-phenolato)-aluminum(III)) expressed by the structural formula below was formed as an electron transport layer by vacuum vapor deposition such that the thickness would be 40 nm.

Lithium fluoride (LiF) was formed over the electron transport layer as an electron injection layer by vacuum vapor deposition such that the thickness would be 1 nm, and metallic aluminum (70 nm) was additionally vapor-deposited, which gave a cathode.

The laminate thus produced was placed in a glove box that had been replaced with argon gas, and was sealed using a stainless steel sealing jar and a UV-setting adhesive (XNR5516HV, made by Nagase Chiba), thereby producing organic electroluminescent elements 2-1 to 2-3.

The organic electroluminescent elements 2-1 to 2-3 thus obtained all emitted dark blue light, and there was little change in chromaticity during brightness modulation.

Working Example 11

A glass substrate (made by Geomatec Co., surface resistance of 10 ohms/square) having an ITO film measuring 2.5 cm$^2$ and 0.5 mm thick was put into a washing vessel and ultrasonically washed in 2-propanol, upon which it was subjected to treatment with UV-ozone for 30 minutes. The following organic compound layers were sequentially deposited onto this transparent anode (ITO film) by a vacuum vapor deposition method. Note that the vapor deposition rate in the following working examples and comparative examples is 0.1 nm/second unless otherwise specified. The vapor deposition rate was measured using a crystal oscillator. The thickness of each of the following layers was also measured using a crystal oscillator:

First layer: HAT-CN; film thickness of 10 nm
Second layer: HT-2; film thickness of 35 nm
Third layer: H-1 and the light-emitting material listed in Table 2 (weight ratio of 93:7); film thickness of 30 nm
Fourth layer: ET-1; film thickness of 30 nm Over this, lithium fluoride (1 nm) and metallic aluminum (100 nm) were vapor-deposited in this order to form a cathode. A patterned mask (a mask in which the emission region measured 2 mm×2 mm) was installed over the lithium fluoride layer here, and metallic aluminum was vapor-deposited.

Without being allowed to come into contact with the air, the laminate thus obtained was placed in a glove box that had been replaced with nitrogen gas, and was sealed using a glass sealing jar and a UV-setting adhesive (XNR5516HV, made by Nagase Chiba), which gave organic electroluminescent elements 11 to 17 and comparative organic electroluminescent elements Ref-11 and Ref-12, in which the emission portion measured 2 mm square. Emission originating in the light-emitting material was observed for each of the elements. The various organic electroluminescent elements thus obtained were tested as follows:

(a) Chromaticity

The chromaticity (x, y) (in the CIE 1931 color space) was found from the emission spectrum when DC voltage was applied to make each organic electroluminescent element emit light so as to obtain a brightness of 1000 cd/m$^2$. Taking the most superior blue (0.14, 0.08) to be the reference point 0, the distance in chromaticity of each of the organic electroluminescent elements from the reference point 0 was calculated upon the CIE chromaticity coordinate plane and evaluated on the following basis. The results thereof are shown in Table 2 below:

○: $0.04 \leq y \leq 0.12$
Δ: $0.03 \leq y < 0.04$, $0.12 < y \leq 0.20$
x: $y < 0.03$, $0.20 < y$ (b) Change in Chromaticity During Brightness Modulation Taking the point W to be the chromaticity coordinate when DC voltage was applied such that the initial brightness of each organic electroluminescent element would be 50 cd/m$^2$, and the point S to be the chromaticity coordinate when DC voltage was applied such that the initial brightness would be 1000 cd/m$^2$, the chromaticity was found from the emission spectrum. The distance between the point W and the point S of each organic electroluminescent element was calculated upon the CIE chromaticity coordinate plane and evaluated on the following basis. The results thereof are shown in Table 2 below:

○: $\Delta y \leq 0.01$
Δ: $0.01 < \Delta y \leq 0.02$
x: $0.02 < \Delta y$

TABLE 2

| | Light-emitting material | Chromaticity | Change in chromaticity during brightness modulation |
|---|---|---|---|
| Organic electroluminescent element 11 of the present invention | Compound 11 | ○ | ○ |
| Organic electroluminescent element 12 of the present invention | Compound 12 | ○ | ○ |
| Organic electroluminescent element 13 of the present invention | Compound 13 | ○ | ○ |
| Organic electroluminescent element 14 of the present invention | Compound 14 | ○ | ○ |
| Organic electroluminescent element 15 of the present invention | Compound 15 | ○ | ○ |

TABLE 2-continued

| | Light-emitting material | Chromaticity | Change in chromaticity during brightness modulation |
|---|---|---|---|
| Organic electroluminescent element 16 of the present invention | Compound 16 | Δ | ○ |
| Organic electroluminescent element 17 of the present invention | Compound 17 | ○ | Δ |
| Comparative element 11 | Compound Ref-11 | x | Δ |
| Comparative element 12 | Compound Ref-12 | x | Δ |

Working Example 12

Other than changing the layer configuration as shown below, organic electroluminescent elements were produced in the same manner as in Working Example 11, and the same evaluations as in Working Example 11 were made. The results are shown in Table 3.

First layer: HT-1; film thickness of 50 nm
Second layer: HT-3; film thickness of 40 nm
Third layer: H-2 and the light-emitting material listed in Table 3 (weight ratio of 95:5); film thickness of 25 nm
Fourth layer: ET-5; film thickness of 5 nm
Fifth layer: ET-3; film thickness of 20 nm

TABLE 3

| | Light-emitting material | Chromaticity | Change in chromaticity during brightness modulation |
|---|---|---|---|
| Organic electroluminescent element 11 of the present invention | Compound 11 | ○ | ○ |
| Organic electroluminescent element 12 of the present invention | Compound 12 | ○ | ○ |
| Organic electroluminescent element 13 of the present invention | Compound 13 | ○ | ○ |
| Organic electroluminescent element 14 of the present invention | Compound 14 | ○ | ○ |
| Organic electroluminescent element 15 of the present invention | Compound 15 | ○ | ○ |
| Organic electroluminescent element 16 of the present invention | Compound 16 | Δ | ○ |
| Organic electroluminescent element 17 of the present invention | Compound 17 | ○ | Δ |
| Comparative element 11 | Compound Ref-11 | Δ | Δ |
| Comparative element 12 | Compound Ref-12 | x | Δ |

Working Example 13

Other than changing the layer configuration as shown below, organic electroluminescent elements were produced in the same manner as in Working Example 11, and the same evaluations as in Working Example 11 were made. The results are shown in Table 4.

First layer: HAT-CN; film thickness of 10 nm
Second layer: HT-3; film thickness of 35 nm
Third layer: H-1 and the light-emitting material listed in Table 4 (weight ratio of 95:5); film thickness of 30 nm
Fourth layer: ET-4; film thickness of 30 nm

TABLE 4

| | Light-emitting material | Chromaticity | Change in chromaticity during brightness modulation |
|---|---|---|---|
| Organic electroluminescent element 11 of the present invention | Compound 11 | ○ | ○ |
| Organic electroluminescent element 12 of the present invention | Compound 12 | ○ | ○ |
| Organic electroluminescent element 13 of the present invention | Compound 13 | ○ | ○ |
| Organic electroluminescent element 14 of the present invention | Compound 14 | ○ | ○ |
| Organic electroluminescent element 15 of the present invention | Compound 15 | ○ | ○ |
| Organic electroluminescent element 16 of the present invention | Compound 16 | Δ | ○ |
| Organic electroluminescent element 17 of the present invention | Compound 17 | ○ | Δ |
| Comparative element 11 | Compound Ref-11 | Δ | Δ |
| Comparative element 12 | Compound Ref-12 | x | Δ |

Working Example 14

Other than changing the layer configuration as shown below, organic electroluminescent elements were produced in the same manner as in Working Example 11, and the same evaluations as in Working Example 11 were made. The results are shown in Table 5.

First layer: HAT-CN; film thickness of 10 nm
Second layer: HT-1; film thickness of 35 nm
Third layer: H-3 and the light-emitting material listed in Table 5 (weight ratio of 93:7); film thickness of 30 nm
Fourth layer: ET-4; film thickness of 30 nm

TABLE 5

| | Light-emitting material | Chromaticity | Change in chromaticity during brightness modulation |
|---|---|---|---|
| Organic electroluminescent element 11 of the present invention | Compound 11 | ○ | ○ |
| Organic electroluminescent element 12 of the present invention | Compound 12 | ○ | ○ |
| Organic electroluminescent element 13 of the present invention | Compound 13 | ○ | ○ |
| Organic electroluminescent element 14 of the present invention | Compound 14 | ○ | ○ |
| Organic electroluminescent element 15 of the present invention | Compound 15 | ○ | ○ |

TABLE 5-continued

|  | Light-emitting material | Chromaticity | Change in chromaticity during brightness modulation |
|---|---|---|---|
| Organic electroluminescent element 16 of the present invention | Compound 16 | Δ | ○ |
| Organic electroluminescent element 17 of the present invention | Compound 17 | ○ | Δ |
| Comparative element 11 | Compound Ref-11 | Δ | Δ |
| Comparative element 12 | Compound Ref-12 | x | Δ |

Working Example 15

Other than changing the layer configuration as shown below, organic electroluminescent elements were produced in the same manner as in Working Example 11, and the same evaluations as in Working Example 11 were made. The results are shown in Table 6.

First layer: HT-1; film thickness of 10 nm

Second layer: HT-2; film thickness of 30 nm

Third layer: H-4 and the light-emitting material listed in Table 6 (weight ratio of 93:7); film thickness of 30 nm Fourth layer: ET-2; film thickness of 30 nm

TABLE 6

|  | Light-emitting material | Chromaticity | Change in chromaticity during brightness modulation |
|---|---|---|---|
| Organic electroluminescent element 11 of the present invention | Compound 11 | ○ | ○ |
| Organic electroluminescent element 12 of the present invention | Compound 12 | ○ | ○ |
| Organic electroluminescent element 13 of the present invention | Compound 13 | ○ | ○ |
| Organic electroluminescent element 14 of the present invention | Compound 14 | ○ | ○ |
| Organic electroluminescent element 15 of the present invention | Compound 15 | ○ | ○ |
| Organic electroluminescent element 16 of the present invention | Compound 16 | Δ | ○ |
| Organic electroluminescent element 17 of the present invention | Compound 17 | ○ | Δ |
| Comparative element 11 | Compound Ref-11 | Δ | Δ |
| Comparative element 12 | Compound Ref-12 | x | Δ |

It was revealed from Tables 2 to 6 above that the organic electroluminescent elements 11 to 17 of the present invention emitted dark blue light, and that there was little change in chromaticity during brightness modulation. Furthermore, it was found that the relative external quantum efficiency was also excellent.

DESCRIPTION OF SYMBOLS 2 substrate
3 anode
4 hole injection layer
5 hole transport layer
6 light-emitting layer
7 hole blocking layer
8 electron transport layer
9 cathode
10 organic electroluminescent element
11 organic layer
12 protective layer
14 adhesive layer
16 sealing container
20 light-emitting device
30 light-scattering member
31 transparent substrate
30A light incidence face
30B light emission face
32 microparticles
40 illumination device

The invention claimed is:

1. An organic electroluminescent element having
a substrate,
a pair of electrodes disposed on this substrate and including an anode and a cathode, and a single or a plurality of organic layers disposed between these electrodes, wherein
said organic layer(s) include a light-emitting layer, and this light-emitting layer contains a host material and at least one light-emitting material expressed by General Formula 1 below:

General Formula 1

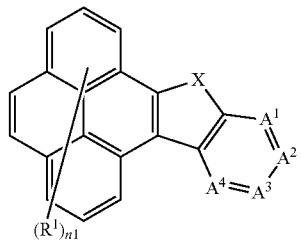

n1 represents an integer from 0 to 8; the $R^1$ groups each independently represents a substituent substituted for a hydrogen atom of the pyrene skeleton, with the proviso that if n1 is 2 or greater, adjacent $R^1$ groups are not linked to each other to form a saturated or unsaturated ring; X represents $CR^aR^b$, wherein $R^a$ and $R^b$ each independently represents a hydrogen atom or a substituent, and $R^a$ and $R^b$ may jointly form a five- or six-membered ring, $NR^c$, wherein $R^c$ represents a hydrogen atom or a substituent, O, S, or $SiR^dR^e$, wherein $R^d$ and $R^e$ each independently represents a hydrogen atom or a substituent, and $R^d$ and $R^e$ may jointly form a five- or six-membered ring; and $A^1$ to $A^4$ each independently represents either N or $CR^f$, wherein $R^f$ represents a hydrogen atom or a substituent, and two adjacent $R^f$ groups may jointly form a saturated or unsaturated ring, but no more than two rings may be formed jointly by two or more of the $R^f$ groups.

2. The organic electroluminescent element according to claim 1, wherein $R^a$, $R^b$, $R^d$, and $R^e$ each independently represent an alkyl group, an aryl group, or a heteroaryl group in General Formula 1 above.

3. The organic electroluminescent element according to claim 1, wherein $R^c$ represents a substituent in General Formula 1 above.

4. The organic electroluminescent element according to claim 1 wherein X represents $CR^{a'}R^{b'}$, wherein $R^{a'}$ and $R^{b'}$ each independently represents an alkyl group, an aryl group, or a heteroaryl group, and $R^{a'}$ and $R^{b'}$ may jointly form a five- or six-membered ring or wherein represents a substituent in General Formula 1 above.

5. The organic electroluminescent element according to claim 1 wherein $R^1$ has at least one N,N-diarylamino group or an aryl group substituted with an N,N-diarylamino group in General Formula 1 above.

6. The organic electroluminescent element according to claim 1 wherein the light-emitting material expressed by General Formula 1 above is expressed by General Formula 2 below:

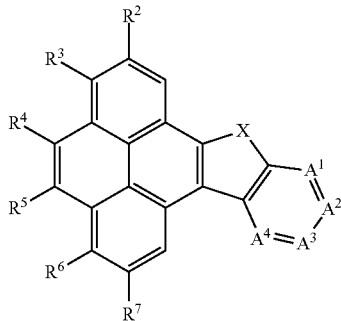

General Formula 2

$R^2$ to $R^7$ each independently represent a hydrogen atom or a substituent, with the proviso that adjacent $R^2$ to $R^7$ groups are not linked to each other to form a saturated or unsaturated ring; X represents $CR^aR^b$, wherein $R^a$ and $R^b$ each independently represent a hydrogen atom or a substituent, and $R^a$ and $R^b$ may jointly form a five- or six-membered ring, $NR^c$, wherein $R^c$ represents a hydrogen atom or a substituent, O, S, or $SiR^dR^e$, wherein $R^d$ and $R^e$ each independently represents a hydrogen atom or a substituent, and $R^d$ and $R^e$ may jointly form a five- or six-membered ring; and $A^1$ to $A^4$ each independently represents either N or $CR^f$, wherein $R^f$ represents a hydrogen atom or a substituent, and two adjacent $R^f$ groups may jointly form a saturated or unsaturated ring, but no more than two rings may be formed jointly by two or more of the $R^f$ groups.

7. The organic electroluminescent element according to claim 1 wherein the light-emitting material expressed by General Formula 1 above is expressed by General Formula 3 below:

General Formula 3

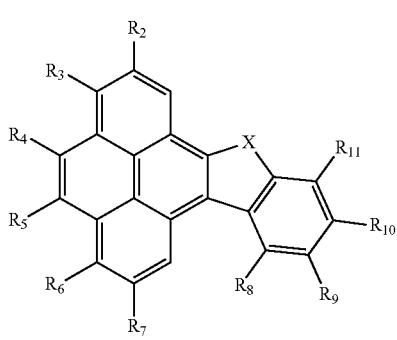

$R^2$ to $R^7$ each independently represents a hydrogen atom or a substituent, with the proviso that adjacent $R^2$ to $R^7$ groups are not linked to each other to form a saturated or unsaturated ring;
X represents $CR^aR^b$, wherein $R^a$ and $R^b$ each independently represents a hydrogen atom or a substituent, and $R^a$ and $R^b$ may jointly form a five- or six-membered ring, $NR^c$, wherein $R^c$ represents a hydrogen atom or a substituent, O, S, or $SiR^dR^e$, wherein $R^d$ and $R^e$ each independently represents a hydrogen atom or a substituent, and $R^d$ and $R^e$ may jointly form a five- or six-membered ring; and
$R^8$ to $R^{11}$ each independently represents a hydrogen atom or a substituent, and adjacent two of the $R^8$ to $R^{11}$ groups may jointly form a saturated or unsaturated ring, but no more than two rings may be formed jointly by two or more of the $R^8$ to $R^{11}$ groups.

8. The organic electroluminescent element according to claim 1 wherein the light-emitting material expressed by General Formula 1 above is expressed by General Formula 4 below:

General Formula 4

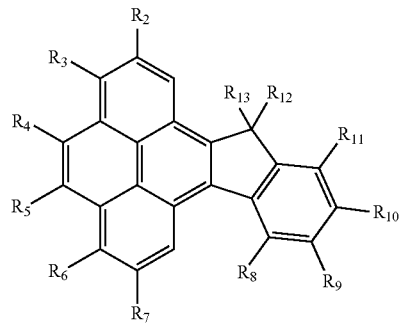

$R^2$ to $R^7$ each independently represents a hydrogen atom or a substituent, with the proviso that adjacent $R^2$ to $R^7$ groups are not linked to each other to form a saturated or unsaturated ring;
$R^8$ to $R^{11}$ each independently represents a hydrogen atom or a substituent, and adjacent two of the $R^8$ to $R^{11}$ groups may jointly form a saturated or unsaturated ring, but no more than two rings may be formed jointly by two or more of the $R^8$ to $R^{11}$ groups; and
$R^{12}$ and $R^{13}$ each independently represents a hydrogen atom or a substituent, and $R^{12}$ and $R^{13}$ may jointly form a five- or six-membered ring.

9. The organic electroluminescent element according to claim 8, wherein at least one of $R^2$ to $R^{11}$ represents a substituent in General Formula 4 above.

10. The organic electroluminescent element according to claim 8, wherein $R^5$ and/or $R^{10}$ represents a substituent in General Formula 4 above.

11. The organic electroluminescent element according to claim 1 wherein said host material contained in said light-emitting layer has a hydrocarbon condensed ring structure with a carbon number of 10 to 50.

12. The organic electroluminescent element according to claim 1 wherein said light-emitting layer is formed by a vacuum vapor deposition process.

13. The organic electroluminescent element according to claim 1 wherein said light-emitting layer is formed by a wet process.

14. A light-emitting device comprising the organic electroluminescent element according to claim 1.

15. A display device comprising the organic electroluminescent element according to claim 1.

16. An illumination device comprising the organic electroluminescent element according to claim 1.

17. A light-emitting material for an organic electroluminescent element expressed by General Formula 1 below:

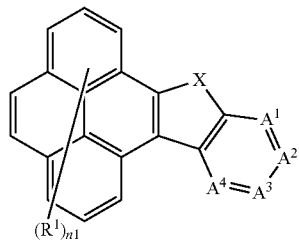

General Formula 1 n1 represents an integer from 0 to 8; the $R^1$ groups each independently represents a substituent substituted for a hydrogen atom of the pyrene skeleton; however, if n1 is 2 or greater, a case is excluded in which adjacent $R^1$ groups are linked to each other to form a saturated or unsaturated ring; X represents $CR^aR^b$, wherein $R^a$ and $R^b$ each independently represents a hydrogen atom or a substituent, and $R^a$ and $R^b$ may jointly form a five- or six-membered ring, $NR^c$, wherein $R^c$ represents a hydrogen atom or a substituent, O, S, or $SiR^dR^e$; $R^d$ and $R^e$ each independently a hydrogen atom or a substituent, and $R^d$ and $R^e$ may jointly form a five- or six-membered ring; and $A^1$ to $A^4$ each independently represents either N or $CR^f$, wherein $R^f$ represents a hydrogen atom or a substituent, and two adjacent $R^f$ groups may jointly form a saturated or unsaturated ring, but no more than two rings may be formed jointly by two or more of the $R^f$ groups, with the proviso that when X is $CH^2$, then at least one of $A^1$ to $A^4$ is $CR^f$ wherein $R^f$ represents a group containing a substituted aryl group or a group containing a di-substituted amino group.

18. The light emitting material according to claim 17, wherein the compound expressed by General Formula 1 is expressed by General Formula 2 below:

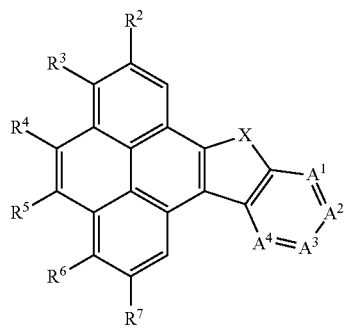

General Formula 2

$R^2$ to $R^7$ each independently represent a hydrogen atom or a substituent, with the proviso that adjacent $R^2$ to $R^7$ groups are not linked to each other to form a saturated or unsaturated ring; X represents $CR^aR^b$, wherein $R^a$ and $R^b$ each independently represent a hydrogen atom or a substituent, and $R^a$ and $R^b$ may jointly form a five- or six-membered ring, $NR^c$, wherein $R^c$ represents a hydrogen atom or a substituent, O, S, or $SiR^dR^e$, wherein $R^d$ and $R^e$ each independently represents a hydrogen atom or a substituent, and $R^d$ and $R^e$ may jointly form a five- or six-membered ring; and $A^1$ to $A^4$ each independently represents either N or $CR^f$, wherein $R^f$ represents a hydrogen atom or a substituent, and two adjacent $R^f$ groups may jointly form a saturated or unsaturated ring, but no more than two rings may be formed jointly by two or more of the $R^f$ groups.

19. The light emitting material according to claim 17, wherein the compound expressed by General Formula 1 above is expressed by General Formula 3 below:

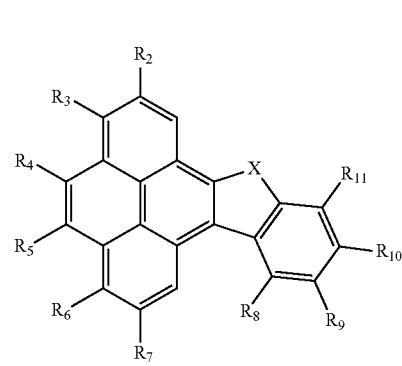

General Formula 3

$R^2$ to $R^7$ each independently represents a hydrogen atom or a substituent, with the proviso that adjacent $R^2$ to $R^7$ groups are not linked to each other to form a saturated or unsaturated ring;

X represents $CR^aR^b$, wherein $R^a$ and $R^b$ each independently represents a hydrogen atom or a substituent, and $R^a$ and $R^b$ may jointly form a five- or six-membered ring, $NR^c$, wherein $R^c$ represents a hydrogen atom or a substituent, O, S, or $SiR^dR^e$, wherein $R^d$ and $R^e$ each independently represents a hydrogen atom or a substituent, and $R^d$ and $R^e$ may jointly form a five- or six-membered ring; and $R^8$ to $R^{11}$ each independently represents a hydrogen atom or a substituent, and adjacent two of the $R^8$ to $R^{11}$ groups may jointly form a saturated or unsaturated ring, but no more than two rings may be formed jointly by two or more of the $R^8$ to $R^{11}$ groups.

20. The light emitting material according to claim 17, wherein the compound expressed by General Formula 1 above is expressed by General Formula 4 below:

General Formula 4

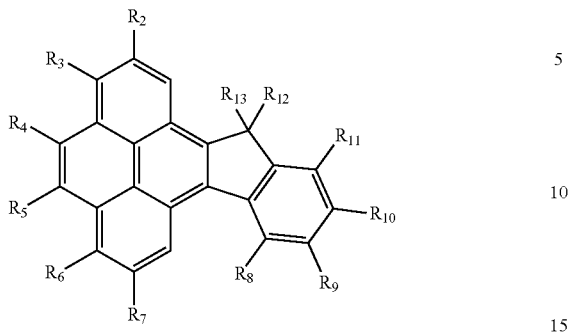

$R^2$ to $R^7$ each independently represents a hydrogen atom or a substituent, with the proviso that adjacent $R^2$ to $R^7$ groups are not linked to each other to form a saturated or unsaturated ring;

$R^8$ to $R^{11}$ each independently represents a hydrogen atom or a substituent, and adjacent two of the $R^8$ to $R^{11}$ groups may jointly form a saturated or unsaturated ring, but no more than two rings may be formed jointly by two or more of the $R^8$ to $R^{11}$ groups; and $R^{12}$ and $R^{13}$ each independently represents a hydrogen atom or a substituent, and $R^{12}$ and $R^{13}$ may jointly form a five- or six-membered ring.

* * * * *